(12) United States Patent
Boer et al.

(10) Patent No.: US 11,293,043 B2
(45) Date of Patent: Apr. 5, 2022

US011293043B2

(54) STEVIOL GLYCOSIDE TRANSPORT

(71) Applicant: DSM IP ASSETS B.V., Heerlen (NL)

(72) Inventors: Viktor Marius Boer, Echt (NL); Priscilla Zwartjens, Echt (NL); Eric Van Den Berg, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/845,736

(22) Filed: Apr. 10, 2020

(65) Prior Publication Data

US 2020/0283816 A1 Sep. 10, 2020

Related U.S. Application Data

(62) Division of application No. 15/751,526, filed as application No. PCT/EP2016/069357 on Aug. 15, 2016, now abandoned.

(60) Provisional application No. 62/204,704, filed on Aug. 13, 2015.

(51) Int. Cl.
| | |
|---|---|
| C12N 1/20 | (2006.01) |
| C12P 19/56 | (2006.01) |
| C07K 14/39 | (2006.01) |
| C07H 15/24 | (2006.01) |
| C12N 9/10 | (2006.01) |

(52) U.S. Cl.
CPC ............... *C12P 19/56* (2013.01); *C07H 15/24* (2013.01); *C07K 14/39* (2013.01); *C12N 9/1051* (2013.01); *C12Y 204/01017* (2013.01)

(58) Field of Classification Search
CPC ......... C07K 14/39; C12N 9/0042; C12N 1/20
See application file for complete search history.

(56) References Cited

U.S. PATENT DOCUMENTS

| | | |
|---|---|---|
| 2015/0031868 A1 | 1/2015 | Lehmann et al. |
| 2016/0153017 A1 | 6/2016 | Van Der Hoeven et al. |

FOREIGN PATENT DOCUMENTS

| | | |
|---|---|---|
| WO | 2013110673 A1 | 8/2013 |
| WO | 2014122328 A1 | 8/2014 |
| WO | 2015/007748 A1 | 1/2015 |

OTHER PUBLICATIONS

H.H. Guo et al. "Protein tolerance to random amino acid change", PNAS 101(25):9205-9210 (Year: 2004).*
International Search Report issued in counterpart International Application No. PCT/EP2016/069357, dated Nov. 18, 2016.
Xiao et al., "Exploiting Issatchenkia orientalis SD108 for Succinic Acid Production" Database, UniProt: AOA099NW03. (Jan. 7, 2016) p. 1.
Xiao et al., Exploiting Issatchenkia orientalis SD108 for Succinic Acid Production Database, UniProt: AOA099P343. (Jan. 7, 2016) p. 1.
GenBank Accession No. KGK39403 (Year: 2014).
GenBank: KGK36146.1, "hypothetical protein JL09-g4704, partial [Pichia kudriavzevii]", 2014.
GenBank: KGK36149.1, "hypothetical protein JL09_g4702, partial [Pichia kudriavzevii]", 2014.

* cited by examiner

*Primary Examiner* — Tekchand Saidha
(74) *Attorney, Agent, or Firm* — McBee Moore & Vanik IP, LLC; Susan McBee; Chester Moore

(57) ABSTRACT

A recombinant host capable of producing a steviol glycoside which overexpresses a polypeptide which mediates steviol glycoside transport and which polypeptide comprises the amino acid sequence set forth in SEQ ID NO: 35 or SEQ ID NO: 38 or an amino acid sequence having at least about 50% sequence identity to either thereto. A recombinant host capable of producing a steviol glycoside which has been modified, preferably in its genome, to result in a deficiency in the production of a polypeptide which mediates steviol glycoside transport and which polypeptide comprises the amino acid sequence set forth in SEQ ID NO: 35 or SEQ ID NO: 38 or an amino acid sequence having at least about 50% sequence identity to either thereto.

9 Claims, 14 Drawing Sheets

Specification includes a Sequence Listing.

```
                        SEQUENCE LISTING

<160> NUMBER OF SEQ ID NOS: 38

<210> SEQ ID NO 1
<211> LENGTH: 600
<212> TYPE: DNA
<213> ORGANISM: Artificial sequence
<220> FEATURE:
<223> OTHER INFORMATION: ScEno2 promoter

<400> SEQUENCE: 1
gtgtcgacgc tgcgggtata gaaagggttc tttactctat agtacctcct cgctcagcat      60
ctgcttcttc ccaaagatga acgcggcgtt atgtcactaa cgacgtgcac caacttgcgg     120
aaagtggaat cccgttccaa aactggcatc cactaattga tacatctaca caccgcacgc     180
cttttttctg aagcccactt tcgtggactt tgccatatgc aaaattcatg aagtgtgata     240
ccaagtcagc atacacctca ctagggtagt ttctttggtt gtattgatca tttggttcat     300
cgtggttcat taatttttt tctccattgc tttctggctt tgatcttact atcatttgga     360
tttttgtcga aggttgtaga attgtatgtg acaagtggca ccaagcatat ataaaaaaaa     420
aaagcattat cttcctacca gagttgattg ttaaaaacgt atttatagca aacgcaattg     480
taattaattc ttatttgta tcttttcttc ccttgtctca atctttatt tttattttat      540 ttttcttttc ttagtttctt tcataacacc aagcaactaa tactataaca tacaataata     600

<210> SEQ ID NO 2
<211> LENGTH: 1056
<212> TYPE: DNA
<213> ORGANISM: Saccharomyces cerevisiae

<400> SEQUENCE: 2
atggcttctg aaaaggaaat cagaagagaa cgtttcttga atgttttccc aaaattggtt      60
gaagaattga acgcttctct attagcttac ggtatgccaa aggaagcttg tgactggtac     120
gctcactctt tgaactacaa caccccaggt ggtaagttga cagaggtct atccgttgtt     180 gacacctacg ccatttttgtc caacaagacc gtcgaacaat aggtcaaga agaatacgaa     240 aaggttgcca tcttaggttg gtgtatcgaa ttgttgcaag cttacttctt ggttgctgat     300
gacatgatga caaatctat caccagaaga ggtcaaccat gttggtacaa ggttccagaa     360
gtcggtgaaa ttgccatcaa cgatgctttc atgttggaag ctgccatcta caagttgttg     420
```

```
aagtctcact tcagaaacga aaagtactac attgacatca ctgaattatt ccacgaagtt      480
actttccaaa ccgaattggg tcaattgatg gacttgatta ccgctccaga agataaggtc      540
gatttgtcca aatttttcctt gaagaaacac tctttcattg tcactttcaa gactgcttac    600
tactcctttt acttgcctgt tgctttggcc atgtatgtcg ctggtatcac cgatgaaaag     660
gacttgaagc aagctcgtga tgtcttgatt ccattaggtg aatacttcca aatccaagat    720
gactacttgg actgtttcgg tactccagaa caaatcggta agattggtac tgatatccaa    780
gacaacaagt gttcctgggt tatcaacaag gctttggaat tggcttctgc tgaacaaaga    840
aagactttgg acgaaaacta cggtaagaag gactctgttg ctgaagctaa gtgtaagaag    900
atcttcaacg atttgaaaat tgaacaatta taccatgaat acgaagaatc tattgccaag    960
gacttgaaag ccaagatctc tcaagtcgac gaatccagag gtttcaaggc tgatgtcttg    1020 actgcttct tgaacaaggt ctacaagaga tcaaaa                                1056

<210> SEQ ID NO 3
<211> LENGTH: 301
<212> TYPE: DNA
<213> ORGANISM: Artificial sequence
<220> FEATURE:
<223> OTHER INFORMATION: Adh1 terminator

<400> SEQUENCE: 3
agcgaatttc ttatgattta tgattttat tattaaataa gttataaaaa aaataagtgt      60
atacaaattt taaagtgact cttaggtttt aaaacgaaaa ttcttattct tgagtaactc    120
tttcctgtag gtcaggttgc tttctcaggt atagcatgag gtcgctctta ttgaccacac    180
ctctaccggc atgccgagca atgcctgca atcgctccc catttcaccc aattgtagat     240
atgctaactc cagcaatgag ttgatgaatc tcggtgtgta ttttatgtcc tcagaggaca    300
a                                                                    301

<210> SEQ ID NO 4
<211> LENGTH: 600
<212> TYPE: DNA
<213> ORGANISM: Artificial sequence
<220> FEATURE:
<223> OTHER INFORMATION: Sc Fba1 promoter

<400> SEQUENCE: 4
ctacttggct tcacatacgt tgcatacgtc gatatagata ataatgataa tgacagcagg      60
attatcgtaa tacgtaatag ttgaaaatct caaaaatgtg tgggtcatta cgtaaataat    120
gataggaatg ggattcttct attttttcctt tttccattct agcagccgtc gggaaaacgt    180
ggcatcctct ctttcgggct caattggagt cacgctgccg tgagcatcct ctctttccat    240
atctaacaac tgagcacgta accaatggaa aagcatgagc ttagcgttgc tccaaaaaag    300
tattggatgg ttaataccat tgtctgttc tcttctgact tgactcctc aaaaaaaaaa      360 aatctacaat caacagatcg cttcaattac gccctcacaa aaacttttt ccttcttctt     420 cgcccacgtt aaattttatc cctcatgttg tctaacggat ttctgcactt gatttattat    480
aaaaagacaa agacataata cttctctatc aatttcagtt attgttcttc cttgcgttat    540
tcttctgttc ttctttttct tttgtcatat ataaccataa ccaagtaata catattcaaa    600

<210> SEQ ID NO 5
<211> LENGTH: 1575
<212> TYPE: DNA
```

<213> ORGANISM: Saccharomyces cerevisiae

<400> SEQUENCE: 5

| | | |
|---|---|---|
| atggaccaat tggtcaagac tgaagtcacc aagaaatctt tcactgctcc agtccaaaag | 60 |
| gcttccactc cagttttgac caacaagacc gtcatctccg gttccaaggt taaatctttg | 120 |
| tcctctgctc aatcttcctc tctggtcca tcttcttctt ctgaagaaga tgattccaga | 180 |
| gatatcgaat ctttggacaa gaaaatcaga ccattggaag aattggaagc tctattgtcc | 240 |
| tctggtaaca ctaagcaatt aaagaacaag gaagttgctg ctttggttat ccacggtaaa | 300 |
| ttgccattgt acgctttgga aaagaaatta ggtgacacca ccagagctgt tgctgtcaga | 360 |
| agaaaggctt tgtccatttt ggctgaagct ccagtcttgg cttccgacag attaccatac | 420 |
| aagaactacg actacgaccg tgtctttggt gcttgttgtg aaaatgtcat tggttacatg | 480 |
| ccattaccag ttggtgtcat tggtccattg gttatcgacg gtacttctta ccacatccca | 540 |
| atggctacca ctgaaggttg tttggttgct ctgccatga ggttgtaa ggccatcaac | 600 |
| gctggtggtg gtgctaccac cgttttgact aaggatggta tgaccagagg tcctgttgtc | 660 |
| agattcccaa ctttgaagag atctggtgct tgtaagatct ggttggattc tgaagaaggt | 720 |
| caaaacgcca tcaagaaggc tttcaactcc acttccagat cgctagatt gcaacacatt | 780 |
| caaacttgtt tagctggtga cttgttgttc atgagattca gaaccaccac tggtgacgct | 840 |
| atgggtatga acatgatctc caagggtgtt gaatactctt tgaagcaaat ggttgaagaa | 900 |
| tacggttggg aagatatgga agttgtctct gtttctggta actactgtac cgacaagaag | 960 |
| ccagctgcca tcaactggat cgaaggtcgt ggtaagtccg ttgttgctga agctaccatt | 1020 |
| ccaggtgacg ttgtcagaaa ggttttgaaa tctgatgttt ctgctttagt cgaattgaac | 1080 |
| attgccaaga acttggtcgg ttctgccatg gctggttccg tcggtggttt caacgctcat | 1140 |
| gccgctaact tggtcactgc tgtttttcttg gctttaggtc aagatccagc tcaaaatgtc | 1200 |
| gaatcctcta actgtatcac tttgatgaag gaagttgacg tgatttgag aatttctgtt | 1260 |
| tccatgccat ccattgaagt cggtactatc ggtggtggta ctgtcttgga accacaaggt | 1320 |
| gccatgttgg acttgttggg tgttcgtggt ccacacgcta ccgctccagg tactaacgcc | 1380 |
| agacaattgg ccagaattgt tgcctgtgcc gtcttggctg gtgaattgtc tctatgtgcc | 1440 |
| gctttggctg ctggtcactt ggttcaatct cacatgaccc acaacagaaa gcctgctgaa | 1500 |
| ccaaccaaac caaacaactt ggatgctact gacattaaca gattaaagga cggttctgtc | 1560 |
| acctgtatca agtct | 1575 |

<210> SEQ ID NO 6
<211> LENGTH: 301
<212> TYPE: DNA
<213> ORGANISM: Artificial sequence
<220> FEATURE:
<223> OTHER INFORMATION: Adh2 terminator

<400> SEQUENCE: 6

| | | |
|---|---|---|
| agcggatctc ttatgtcttt acgatttata gttttcatta tcaagtatgc ctatattagt | 60 |
| atatagcatc tttagatgac agtgttcgaa gtttcacgaa taaagataa tattctactt | 120 |
| tttgctccca ccgcgtttgc tagcacgagt gaacaccatc cctcgcctgt gagttgtacc | 180 |
| cattcctcta aactgtagac atggtagctt cagcagtgtt cgttatgtac ggcatcctcc | 240 |
| aacaaacagt cggttatagt ttgtcctgct ccctctgaatc gtgtccctcg atatttctca | 300 |
| t | 301 |

<210> SEQ ID NO 7
<211> LENGTH: 600
<212> TYPE: DNA
<213> ORGANISM: Artificial sequence
<220> FEATURE:
<223> OTHER INFORMATION: Sc Tef1 promoter

<400> SEQUENCE: 7

```
ttggctgata atagcgtata aacaatgcat actttgtacg ttcaaaatac aatgcagtag      60
atatatttat gcatattaca tataatacat atcacatagg aagcaacagg cgcgttggac     120
ttttaatttt cgaggaccgc gaatccttac atcacaccca atcccccaca agtgatcccc     180
cacacaccat agcttcaaaa tgtttctact cctttttttac tcttccagat tttctcggac    240
tccgcgcatc gccgtaccac ttcaaaacac ccaagcacag catactaaat ttcccctctt     300
tcttcctcta gggtgtcgtt aattacccgt actaaaggtt tggaaaagaa aaagacacc      360
gcctcgtttc ttttcttcg tcgaaaaagg caataaaaat ttttatcacg tttcttttc       420
ttgaaaattt ttttttttga ttttttctc tttcgatgac ctcccattga tatttaagtt     480
aataaacggt cttcaatttc tcaagtttca gtttcatttt tcttgttcta ttacaacttt    540
ttttacttct tgctcattag aaagaaagca tagcaatcta atctaagttt taattacaaa   600
```

<210> SEQ ID NO 8
<211> LENGTH: 1005
<212> TYPE: DNA
<213> ORGANISM: Saccharomyces cerevisiae

<400> SEQUENCE: 8

```
atggaagcta agattgacga attgatcaac aacgaccctg tctggtcctc tcaaaacgaa     60
tctttgatct ccaagccata caaccacatc ttgttgaagc aggtaagaa cttcagatta    120
aacttgattg ttcaaatcaa cagagttatg aacttgccaa aggaccaatt ggccattgtt   180
tcccaaattg tcgaattgtt gcacaactcc tctctattga tcgatgacat tgaagataat  240
gctccattaa gaagaggtca aaccacttct catttgattt tcggtgtccc atccaccatc    300
aacactgcta actacatgta cttcagagcc atgcaattgg tttctcaatt gaccaccaag   360
gaaccattat accacaactt gatcactatc tttaacgaag aattgattaa cttgcaccgt   420
ggtcaaggtt tggacatcta ctggagagat ttcttgccag aaattattcc aactcaagaa    480
atgtacttga acatggtcat gaacaagact ggtggtttat tcagattgac tttacgtttg    540
atggaagctt tgtctccatc ttcccaccac ggtcactctt tggttccatt catcaatcta    600
ttaggtatca tctaccaaat cagagatgat tacttgaact tgaaggactt ccaaatgtcc   660
tctgaaaagg gttcgctga agatatcact gaaggtaaat tgtctttccc aattgtccac    720
gccttgaact ttaccaagac caagggtcaa actgaacaac acaacgaaat tttgagaatc   780
ttattgttga gaacttctga caaggacatc aagttgaaat tgatccaaat cttggaattc    840
gataccaact ctttggctta caccaagaac ttcatcaacc aattggttaa catgatcaag   900
aatgacaacg aaaacaaata cttgccagac ttggcttccc actccgatac cgctaccaac   960
ttgcacgacg aattgttgta cattattgac catttgtctg agtta                   1005
```

<210> SEQ ID NO 9
<211> LENGTH: 301
<212> TYPE: DNA
<213> ORGANISM: Artificial sequence
<220> FEATURE:

<223> OTHER INFORMATION: Sc Gmp1 terminator

<400> SEQUENCE: 9

```
agtctgaaga atgaatgatt tgatgatttc ttttcccctc cattttctt actgaatata    60
tcaatgatat agacttgtat agtttattat ttcaaattaa gtagctatat atagtcaaga  120
taacgtttgt ttgacacgat tacattattc gtcgacatct tttttcagcc tgtcgtggta  180
gcaatttgag gagtattatt aattgaatag gttcattttg cgctcgcata aacagttttc  240
gtcagggaca gtatgttgga atgagtggta attaatggtg acatgacatg ttatagcaat  300
a                                                                  301
```

<210> SEQ ID NO 10
<211> LENGTH: 600
<212> TYPE: DNA
<213> ORGANISM: Artificial sequence
<220> FEATURE:
<223> OTHER INFORMATION: Sc Pgk1 promoter

<400> SEQUENCE: 10

```
gggccagaaa aaggaagtgt ttccctcctt cttgaattga tgttaccctc ataaagcacg    60
tggcctctta tcgagaaaga aattaccgtc gctcgtgatt tgtttgcaaa aagaacaaaa  120
ctgaaaaaac ccagacacgc tcgacttcct gtcttcctat tgattgcagc ttccaatttc  180
gtcacacaac aaggtcctag cgacggctca caggttttgt aacaagcaat cgaaggttct  240
ggaatggcgg gaaagggttt agtaccacat gctatgatgc ccactgtgat ctccagagca  300
aagttcgttc gatcgtactg ttactctctc tctttcaaac agaattgtcc gaatcgtgtg  360
acaacaacag cctgttctca cacactcttt tcttctaacc aaggggtgg tttagtttag  420
tagaacctcg tgaaacttac atttacatat atataaactt gcataaattg gtcaatgcaa  480
gaaatacata tttggtcttt tctaattcgt agttttcaa gttcttagat gctttctttt  540
tctctttttt acagatcatc aaggaagtaa ttatctactt tttacaacaa atataaaaca  600
```

<210> SEQ ID NO 11
<211> LENGTH: 1422
<212> TYPE: DNA
<213> ORGANISM: Artificial sequence
<220> FEATURE:
<223> OTHER INFORMATION: UGT2_1a CpO for S. cerevisiae

<400> SEQUENCE: 11

```
atggctacat ctgattctat tgttgatgac aggaagcagt tgcatgtggc tactttccct    60
tggcttgctt tcggtcatat actgccttac ctacaactat caaaactgat agctgaaaaa  120
ggacataaag tgtcattcct ttcaacaact agaaacattc aaagattatc ttcccacata  180
tcaccattga ttaacgtcgt tcaattgaca cttccaagag tacaggaatt accagaagat  240
gctgaagcta caacagatgt gcatcctgaa gatatccctt acttgaaaaa ggcatccgat  300
ggattacagc ctgaggtcac tagattcctt gagcaacaca gtccagattg gatcatatac  360
gactacactc actattggtt gccttcaatt gcagcatcac taggcatttc tagggcacat  420
ttcagtgtaa ccacaccttg ggccattgct tacatgggtc catccgctga tgctatgatt  480
aacggcagtg atggtagaac taccgttgaa gatttgacaa ccccaccaaa gtggtttcca  540
tttccaacta aagtctgttg gagaaaaca gacttagcaa gactggttcc atacaaggca  600
ccaggaatct cagacggcta tagaatgggt ttagtcctta aagggtctga ctgcctattg  660
tctaagtgtt accatgagtt tgggacacaa tggctaccac ttttggaaac attacaccaa  720
```

```
gttcctgtcg taccagttgg tctattacct ccagaaatcc ctggtgatga aaggacgag      780 acttgggttt caatcaaaaa gtggttagac gggaagcaaa aaggctcagt ggtatatgtg     840
gcactgggtt ccgaagtttt agtatctcaa acagaagttg tggaacttgc cttaggtttg     900
gaactatctg gattgccatt tgtctgggcc tacagaaaac caaaaggccc tgcaaagtcc     960
gattcagttg aattgccaga cggctttgtc gagagaacta gagatagagg ttggtatgg     1020 acttcatggg ctccacaatt gagaatcctg agtcacgaat ctgtgtgcgg tttcctaaca    1080
cattgtggtt ctggttctat agttgaagga ctgatgtttg gtcatccact tatcatgttg    1140
ccaatctttg gtgaccagcc tttgaatgca cgtctgttag aagataaaca agttggaatt    1200
gaaatcccac gtaatgagga agatggatgt ttaaccaagg agtctgtggc cagatcatta    1260
cgttccgttg tcgttgaaaa ggaaggcgaa atctacaagg ccaatgcccg tgaactttca    1320
aagatctaca atgacacaaa gtagagaag gaatatgttt ctcaatttgt agattaccta    1380
gagaaaaacg ctagagccgt agctattgat catgaatcct aa                       1422

<210> SEQ ID NO 12
<211> LENGTH: 1001
<212> TYPE: DNA
<213> ORGANISM: Artificial sequence
<220> FEATURE:
<223> OTHER INFORMATION: Kl prom 12 promoter

<400> SEQUENCE: 12
cgtaaaaact aaaacgagcc cccaccaaag aacaaaaaag aaggtgctgg gcccccactt      60
tcttcccttg cacgtgatag gaagatggct acagaaacaa gaagatggaa atcgaaggaa     120
agagggagac tggaagctgt aaaaactgaa atgaaaaaaa aaaaaaaaaa aaaaaaacaa     180
gaagctgaaa atggaagact gaaatttgaa aaatggtaaa aaaaaaaaag aaacacgaag    240
ctaaaaacct ggattccatt ttgagaagaa gcaagaaagg taagtatggt aacgaccgta    300
caggcaagcg cgaaggcaaa tggaaaagct ggagtccgga agataatcat ttcatcttct    360
tttgttagaa cagaacagtg gatgtccctc atctcggtaa cgtattgtcc atgccctaga    420
actctctgtc cctaaaaaga ggacaaaaac ccaatggttt ccccagcttc cagtggagcc    480
accgatccca ctggaaacca ctggacagga agagaaaatc acggacttcc tctattgaag    540
gataattcaa cactttcacc agatcccaaa tgtcccgccc ctattcccgt gttccatcac    600
gtaccataac ttaccatttc atcacgttct ctatggcaca ctggtactgc ttcgactgct    660
ttgcttcatc ttctctatgg gccaatgagc taatgagcac aatgtgctgc gaaataaagg    720
gatatctaat ttatattatt acattataat atgtactagt gtggttattg gtaattgtac    780
ttaattttga tatataaagg gtggatcttt ttcattttga atcagaattg gaattgcaac    840
ttgtctcttg tcactattac ttaatagtaa ttatatttct tattaacctt tttttaagt     900 caaaacacca aggacaagaa ctactcttca aggtatttc aagttatcat acgtgtcaca    960
cacgcttcac agtttcaagt aaaaaaaaag aatattacac a                       1001

<210> SEQ ID NO 13
<211> LENGTH: 2229
<212> TYPE: DNA
<213> ORGANISM: Stevia rebaudiana

<400> SEQUENCE: 13
atgtgtaaag ctgtttccaa ggaatactct gacttgttgc aaaaggatga agcctccttc      60
```

```
accaaatggg atgatgacaa agttaaggac catttagaca ctaacaagaa cttgtaccca    120
aacgatgaaa tcaaggaatt cgtcgaatct gtcaaagcta tgttcggttc catgaatgat    180
ggtgaaatca acgtttccgc ttacgacacc gcttgggttg ctttggttca agacgttgat    240
ggttccggtt ctccacaatt cccatcttct ttggaatgga ttgccaacaa ccaattgtct    300
gatggttctt ggggtgacca tttgttattc tctgctcacg acagaattat taacacttta    360
gcttgtgtca ttgctttgac ttcctggaat gtccatccat ccaagtgtga aaagggtttg    420
aacttcttga gagaaaacat ctgtaagttg gaagatgaaa atgctgaaca catgccaatt    480
ggtttcgaag ttaccttccc atctttgatt gatatcgcca agaagttgaa catcgaagtc    540
ccagaagaca ccccagcttt gaaggaaatc tacgccagaa gagatatcaa gttgaccaaa    600
atcccaatgg aagttttgca aaggttcca ccaccttgt tgcactcttt ggaaggtatg     660
ccagacttgg aatgggaaaa gttgttaaag ttgcaatgta aggacggttc tttcttgttc    720
tctccatctt ctaccgcctt tgctttgatg caaactaagg acgaaaagtg tctacaatac    780
ttaactaata tcgttaccaa attcaacggt ggtgtcccaa acgtttaccc tgttgacttg    840
tttgaacaca tctgggttgt tgacagattg caacgtttgg gtattgctcg ttatttcaag    900
tctgaaatca aggactgtgt tgaatacatc aacaagtact ggactaagaa cggtatctgt    960
tgggctcgta acaccacgt tcaagatatc gacgacactg ctatgggttt cagagtcttg   1020
agagctcatg gttacgatgt cacccccagat gtcttcagac aattcgaaaa ggatggtaag   1080
ttcgtttgtt ttgccggtca atccactcaa gccgtcactg gtatgttcaa cgtctacaga   1140
gcttctcaaa tgttgttccc aggtgaaaga atcctagaag acgctaagaa gttctcctac   1200
aactacttga agaaaagca atctactaac gaattgttgg acaaatggat cattgccaaa   1260
gacttaccag gtgaagtcgg ttacgctttg gatattccat ggtacgcttc tctaccaaga   1320
ttagaaacca gatactactt ggaacaatac ggtggtgaag acgatgtctg gatcggtaag   1380
accttgtaca gaatgggtta cgtttccaac aacacttact tggaaatggc caaattggac   1440
tacaacaact acgtcgccgt cttacaattg gaatggtaca ccattcaaca atggtacgtt   1500
gacattggta ttgaaaagtt tgaatccgac aacatcaagt ccgtcttggt ttcctactac   1560
ttggctgctg cttccatctt tgaaccagaa agatccaagg aaagaattgc ttgggctaag   1620
accaccatct tggttgacaa gatcacttct atttttcgact cttcccaatc ttccaaggaa   1680
gatatcaccg ctttcattga caaattcaga acaagtctt cttccaagaa gcactccatt   1740
aacggtgaac catggcacga gttatggtt gctttgaaga agactttgca cggttttgct   1800
ttggatgctt tgatgactca ctctcaagat attcaccctc aattacacca agcttgggaa   1860
atgtggttaa ccaagttgca agatggtgtc gatgtcactg ctgaattgat ggttcaaatg   1920
atcaacatga ctgccggtag atgggtttct aaggaattgt tgactcaccc tcaataccaa   1980
cgtttgtcca ccgtcaccaa ctctgtctgt cacgacatca ctaagttgca aacttcaaa   2040
gaaaactcca ctactgtcga ttctaaggtt caagaattgg ttcaattagt tttctctgac   2100
accccagatg acttggacca agacatgaag caaactttct tgactgtcat gaagaccttc   2160
tactacaagg cttggtgtga cccaaacacc atcaacgacc atatttctaa ggtcttcgaa   2220
attgttatc                                                           2229
```

<210> SEQ ID NO 14
<211> LENGTH: 2271
<212> TYPE: DNA
<213> ORGANISM: Stevia rebaudiana

<400> SEQUENCE: 14

```
atgacttctc acggtggtca aaccaaccca accaacttga ttattgacac caccaaggaa      60
agaatccaaa agcaattcaa gaatgttgaa atctccgttt cctcctacga cactgcttgg     120
gttgccatgg ttccatctcc aaactcccca aagtctccat gtttcccaga atgtttgaac     180
tggttaatca acaaccaatt gaacgatggt tcctggggtt tagtcaatca cacccacaac     240
cacaatcacc cattgttgaa ggactctcta tcctccactt tggcttgtat cgttgctttg     300
aagagatgga acgttggtga agaccaaatc aacaagggtt tgtcctttat tgaatccaac     360
ttggcttctg ctactgaaaa gtcccaacca tctcctatcg ttttgacat catttttccca     420
ggtttattgg aatacgctaa gaacttggac atcaacttat tatctaagca aaccgatttc     480
tccttgatgt tgcacaagag agaattggaa caaaagagat gtcactccaa cgaaatggac     540
ggttacttgg cttacatttc tgaaggtttg ggtaacttgt acgactggaa catggtcaag     600
aaataccaaa tgaagaacgg ttccgttttc aactctccat ctgctaccgc tgctgctttc     660
atcaaccatc aaaacccagg ttgtttgaac tacttgaact ctttgttgga caaattcggt     720
aacgctgttc caactgtcta cccacacgat ttgtttatca gattatccat ggttgacacc     780
attgaacgtt tgggtatttc tcatcacttc agagtcgaaa tcaagaacgt tttggatgaa     840
acttacagat gttgggttga aagagatgaa caaatcttca tggatgtcgt cacttgtgcc     900
ttggccttca gattattgag aattaacggt tacgaagttt ctccagaccc attggctgaa     960
atcactaacg aattggcttt gaaggacgaa tacgccgctt tggaaactta ccatgcctct    1020
cacatcttat accaagaaga cttgtcctct ggtaagcaaa tcttgaagtc tgctgacttc    1080
ttgaaggaaa ttatctctac tgattctaac agattgtcca agttgattca caggaagtt     1140
gaaaacgcct tgaaattccc aatcaacact ggtttggaaa gaattaacac cagaagaaac    1200
atccaattat acaacgttga caacactaga atcttgaaga ctacttatca ctcttccaac    1260
atctccaaca ctgactactt gagattggct gtcgaagatt tctacacctg tcaatctatt    1320
tacagagaag aattgaaggg tttggaaaga tgggttgtcg aaaacaaatt ggaccaattg    1380
aaatttgcta gacaaaagac cgcctactgt tacttctccg ttgctgccac tttgtcctct    1440
ccagaattat ctgacgccag aatctcctgg gctaagaatg gtatcttgac caccgttgtc    1500
gatgacttct cgatattgg tggtaccatt gacgaattga ccaacttgat tcaatgtgtt    1560
gaaaagtgga acgtcgatgt cgataaggac tgttgttctg aacacgtcag aatcttattc    1620
ttggctttga aagatgctat ctgttggatc ggtgacgaag cttttcaaatg gcaagctcgt    1680
gacgttacct ctcacgtcat ccaaacctgg ttggaattga tgaactctat gttgagagaa    1740
gccatctgga cccgtgatgc ttacgtccca actttgaacg aatacatgga aaatgcttac    1800
gtttctttcg ctttgggtcc aattgtcaag cctgctattt acttcgttgg tccaaagttg    1860
tccgaagaaa ttgttgaatc ttctgaatac acaacttgt tcaaattgat gtctactcaa    1920
ggtcgtttgt tgaacgatat ccactctttc aagcgtgaat tcaaggaagg taagttgaat    1980
gctgttgctt tgcatttgtc taacggtgaa tctggtaagg tcgaagaaga agttgtcgaa    2040
gaaatgatga tgatgatcaa gaacaagaga aggaattga tgaagttgat ctttgaagaa    2100
aacggttcta ttgtcccaag agcttgtaag gatgctttct ggaacatgtg tcacgtcttg    2160
aacttcttct acgctaacga tgacggtttc actggtaaca ccatcttaga caccgtcaag    2220
gacatcattt acaacccatt agtcttggtt aacgaaaacg aagaacaaag a             2271
```

<210> SEQ ID NO 15
<211> LENGTH: 301
<212> TYPE: DNA
<213> ORGANISM: Artificial sequence
<220> FEATURE:
<223> OTHER INFORMATION: Sc Tal1 terminator

<400> SEQUENCE: 15

| aggaagtatc tcggaaatat taatttaggc catgtcctta tgcacgtttc ttttgatact | 60 |
| tacgggtaca tgtacacaag tatatctata tatataaatt aatgaaaatc ccctatttat | 120 |
| atatatgact ttaacgagac agaacagttt tttattttt atcctatttg atgaatgata | 180 |
| cagtttctta ttcacgtgtt atacccacac caaatccaat agcaataccg ccatcacaa | 240 |
| tcactgtttc ggcagcccct aagatcagac aaaacatccg gaaccacctt aaatcaacgt | 300 |
| c | 301 |

<210> SEQ ID NO 16
<211> LENGTH: 1539
<212> TYPE: DNA
<213> ORGANISM: Artificial sequence
<220> FEATURE:
<223> OTHER INFORMATION: KO_2_ Lactuca_sativa_Sc_CpO

<400> SEQUENCE: 16

| atggatggtg tcattgacat gcaaaccatt ccattgagaa ccgccattgc cattggtggt | 60 |
| actgctgttg ctttggttgt tgctctatac ttctggttct tgagatctta cgcttctcca | 120 |
| tctcaccact ctaaccattt gccacctgtt ccagaagttc caggtgtccc agtcttgggt | 180 |
| aacttgttgc aattgaaaga aaagaagcca tacatgactt tcaccaaatg ggctgaaatg | 240 |
| tacggtccaa tctactctat cagaactggt gctacctcca tggttgttgt ttcctctaac | 300 |
| gaaattgcca aggaagttgt tgtcactaga ttcccatcca tctccaccag aaagttgtct | 360 |
| tacgctttga aggtcttgac tgaagataag tccatggttg ctatgtctga ttaccatgac | 420 |
| taccacaaga ccgtcaaaag acacattttg actgctgtct taggtccaaa cgcccaaaag | 480 |
| aagttccgtg ctcacagaga caccatgatg aaaacgtttt ccaatgaatt gcatgccttc | 540 |
| tttgaaaaga acccaaacca agaagtcaac ttgagaaaga tcttccaatc tcaattgttc | 600 |
| ggtttggcca tgaagcaagc tttgggtaag gatgtcgaat ctatctacgt caaggacttg | 660 |
| gaaactacca tgaagagaga agaaatcttt gaagtcttgg ttgttgaccc aatgatgggt | 720 |
| gccattgaag tcgattggag agacttcttc ccatacttga atgggttcc aaacaaatct | 780 |
| ttcgaaaaca tcattcacag aatgtacacc cgtcgtgaag ctgtcatgaa ggctttgatc | 840 |
| caagaacaca gaagagaat tgcttctggt gaaaacttaa actcctacat tgactacttg | 900 |
| ttgtctgaag ctcaaacttt gactgacaag caattgttga tgtccctatg ggaaccaatc | 960 |
| attgaatctt ccgacaccac catggtcacc actgaatggg ctatgtacga attggctaag | 1020 |
| aatccaaaca tgcaagacag attgtacgaa gaaatccaat ctgtttgtgg ttccgaaaag | 1080 |
| atcactgaag aaaacttgtc tcaattacca tacttgtacg ctgttttcca gaaactttg | 1140 |
| agaaagcact gtccagttcc aatcatgcca ttgagatacg tccacgaaaa caccgttttg | 1200 |
| ggtggttacc acgttccagc tggtactgaa gttgctatca acatctatgg ttgtaacatg | 1260 |
| gacaagaagg tctgggaaaa cccagaagaa tggaacccag aaagattctt atccgaaaag | 1320 |
| gaatccatgg acttgtacaa gaccatggcc ttcggtggtg gtaagagagt ttgtgctggt | 1380 |
| tctttgcaag ctatggtcat ctcttgtatc ggtattggta gattagtcca agattttgaa | 1440 |

```
tggaaattga aagatgacgc tgaagaagat gtcaacactt taggtttaac cactcaaaag    1500
ttgcacccat tattggcttt gatcaaccct cgaaagtaa                          1539

<210> SEQ ID NO 17
<211> LENGTH: 301
<212> TYPE: DNA
<213> ORGANISM: Artificial sequence
<220> FEATURE:
<223> OTHER INFORMATION: Sc Tpi1 terminator

<400> SEQUENCE: 17
agattaatat aattatataa aaatattatc ttcttttctt tatatctagt gttatgtaaa     60
ataaattgat gactacggaa agcttttta tattgtttct ttttcattct gagccactta    120
aatttcgtga atgttcttgt aagggacggt agatttacaa gtgatacaac aaaaagcaag    180 gcgcttttc taataaaaag aagaaaagca tttaacaatt gaacacctct atatcaacga    240
agaatattac tttgtctcta aatccttgta aaatgtgtac gatctctata tgggttactc    300
a                                                                    301

<210> SEQ ID NO 18
<211> LENGTH: 403
<212> TYPE: DNA
<213> ORGANISM: Artificial sequence
<220> FEATURE:
<223> OTHER INFORMATION: Ag lox_TEF1 promoter

<400> SEQUENCE: 18
taccgttcgt ataatgtatg ctatacgaag ttatgtcccc gccgggtcac ccggccagcg     60
acatggaggc ccagaatacc ctccttgaca gtcttgacgt gcgcagctca ggggcatgat    120
gtgactgtcg cccgtacatt tagcccatac atccccatgt ataatcattt gcatccatac    180
attttgatgg ccgcacggcg cgaagcaaaa attacggctc ctcgctgcag acctgcgagc    240
agggaaacgc tccccctcaca gacgcgttga attgtcccca cgccgcgccc ctgtagagaa    300
atataaaagg ttaggatttg ccactgaggt tcttctttca tatacttcct tttaaaatct    360
tgctaggata cagttctcac atcacatccg aacataaaca aca                      403

<210> SEQ ID NO 19
<211> LENGTH: 810
<212> TYPE: DNA
<213> ORGANISM: Artificial sequence
<220> FEATURE:
<223> OTHER INFORMATION: KANMX

<400> SEQUENCE: 19
atgggtaagg aaaagactca cgtttcgagg ccgcgattaa attccaacat ggatgctgat     60
ttatatgggt ataaatgggc tcgcgataat gtcgggcaat caggtgcgac aatctatcga    120
ttgtatggga agcccgatgc gccagagttg tttctgaaac atggcaaagg tagcgttgcc    180
aatgatgtta cagatgagat ggtcagacta aactggctga cggaatttat gcctcttccg    240
accatcaagc attttatccg tactcctgat gatgcatggt tactcaccac tgcgatcccc    300
ggcaaaacag cattccaggt attagaagaa tatcctgatt caggtgaaaa tattgttgat    360
gcgctggcag tgttcctgcg ccggttgcat tcgattcctg tttgtaattg tccttttaac    420
agcgatcgcg tatttcgttt ggctcaggcg caatcacgaa tgaataacgg tttggttgat    480
gcgagtgatt ttgatgacga gcgtaatggc tggcctgttg aacaagtctg gaaagaaatg    540
```

```
cataagcttt tgccattctc accggattca gtcgtcactc atggtgattt ctcacttgat    600
aaccttattt ttgacgaggg gaaattaata ggttgtattg atgttggacg agtcggaatc    660
gcagaccgat accaggatct tgccatccta tggaactgcc tcggtgagtt ttctccttca    720
ttacagaaac ggcttttca aaaatatggt attgataatc ctgatatgaa taaattgcag    780
tttcatttga tgctcgatga gttttctaa                                     810

<210> SEQ ID NO 20
<211> LENGTH: 285
<212> TYPE: DNA
<213> ORGANISM: Artificial sequence
<220> FEATURE:
<223> OTHER INFORMATION: Ag Tef1_lox terminator

<400> SEQUENCE: 20
atcagtactg acaataaaaa gattcttgtt ttcaagaact tgtcatttgt atagtttttt     60
tatattgtag ttgttctatt ttaatcaaat gttagcgtga tttatatttt ttttcgcctc    120
gacatcatct gcccagatgc gaagttaagt gcgcagaaag taatatcatg cgtcaatcgt    180
atgtgaatgc tggtcgctat actgctgtcg attcgatact aacgccgcca tccagtgtcg    240
aaaacgagct cataacttcg tataatgtat gctatacgaa cggta                   285

<210> SEQ ID NO 21
<211> LENGTH: 1575
<212> TYPE: DNA
<213> ORGANISM: Arabidopsis thaliana

<400> SEQUENCE: 21
atggaatctt tagtcgttca caccgtcaat gccatctggt gtattgtcat tgttggtatt     60
ttctctgttg gttaccacgt ttacggtcgt gccgttgttg aacaatggag aatgagaaga    120
tctttgaaat tgcaaggtgt caagggtcca ccaccatcca ttttcaacgg taatgtctct    180
gaaatgcaaa gaatccaatc tgaagctaag cactgttccg gtgacaacat catttctcac    240
gattactcct cctctttgtt ccctcacttt gaccactgga gaaagcaata cggtagaatc    300
tacacctact ccactggttt gaaacaacat ttgtacatca accatccaga aatggtcaag    360
gaattatctc aaaccaacac tttgaactta ggtcgtatca ctcacatcac caagagattg    420
aacccaatct taggtaacgg tatcatcact ccaacggtc cacactgggc tcatcaaaga    480
agaattattg cttacgaatt cacccacgac aaaatcaagg gtatggtcgg tttgatggtc    540
gaatctgcca tgccaatgtt gaacaaatgg aagaaatgg ttaagagagg tggtgaaatg    600
ggttgtgaca tccgtgttga cgaagatttg aaggatgttt ctgctgatgt cattgctaag    660
gcttgtttcg gttcctcttt ctccaagggg aaggctatct ctccatgat cagagacttg    720 ttgactgcca tcactaagag atctgttttg ttcagattca acggtttcac cgacatggtt    780
ttcggttcca gaagcatgg tgatgtcgat atcgatgctt tggaaatgga attggaatct    840
tctatctggg aaaccgttaa ggaaagagaa attgaatgta aggacactca caagaaggat    900
ttgatgcaat taatcttgga aggtgccatg agatcttgtg acggtaactt gtgggacaag    960
tctgcttaca aagatttgt tgtcgacaac tgtaaatcca tctactttgc cggtcacgac   1020
tctactgctg tctccgtttc ctggtgtttg atgttgctag ctttgaaccc atcctggcaa   1080
gtcaagatca gagatgaaat cttatcttct tgtaagaacg gtattccaga tgctgaatcc   1140 attccaaaact tgaagaccgt taccatggtc attcaagaaa ctatgagatt gtacccacca   1200
gctccaattg tcggtagaga agcttccaag gacatcagat taggtgactt ggttgttcca   1260
```

```
aagggtgttt gtatctggac tttgattcca gctttgcacc gtgacccaga aatctggggt    1320
ccagatgcta acgacttcaa gccagaaaga ttctctgaag gtatttccaa ggcttgtaaa    1380
tacccacaat cttacatccc attcggtttg gtccaagaa cctgtgtcgg taagaacttc     1440
ggtatgatgg aagtcaaagt tttggtttct tgattgttt ccaagttctc tttcaccttg     1500
tctccaactt accaacactc tccatctcac aagttgttgg ttgaacctca acacggtgtt    1560
gtcattagag tcgtt                                                     1575

<210> SEQ ID NO 22
<211> LENGTH: 1000
<212> TYPE: DNA
<213> ORGANISM: Artificial sequence
<220> FEATURE:
<223> OTHER INFORMATION: Kl prom 6 promoter

<400> SEQUENCE: 22 caaaggggggg gcagggacag ggatacgaca agggctgggg aaaaaaaaaa agatagatac    60
gattggccgg gtaagcctgg ggaaatgtag caagtgcggg taagttaaaa ggtaaccacg    120
tgactccgga agagtcacgt ggttacggac tttttttctct agatctcagc tttttatcgg    180
tcttaccctg ccctcctgcc cctgcccct tcccttgcc ccaaaaagaa aggaaatctg      240
ttggatttcg ctcaggccat ccctttcgtt aatatcggtt atcgctttac acactgcaca   300
tccttctgtc caaaggaat ccagaagttt agcttttcct tcctttccca cagacattag    360
cctaggccct ctctcatcat ttgcatgcct cagccaatgt accaagaata acgcaacgag   420
gttgggaaat tttaacccaa caatcgatgc agatgtgaca agagattaga cacgttccag   480
ataccagatt acacagcttg tgctagcaga gtgacatatg gtggtgttgt gtctcgttta   540
gtacctgtaa tcgagagtgt tcaaatcagt cgatttgaac accttactg ccactgaata   600 ttgattgaat accgtttatt gaaggtttta tgagtgatct tctttcggtc caggacaatt   660
tgttgagctt tttctatgta gagttccgtc ccttttttt tttttttgc tttctcgcac     720 ttactagcac tatttttttt tcacacacta aaacacttta ttttaatcta tatatatata   780
tatatatata tgtaggaatg gaatcacaga catttgatac tcatcctcat ccttattaat   840
tcttgtttta atttgtttga cttagccaaa ccaccaatct caacccatcg tatttcaggt   900
attgtgtgtc tagtgtgtct ctggtatacg gaaataagtg ccagaagtaa ggaagaaaca    960
aagaacaagt gtctgaatac tactagcctc tcttttcata                          1000

<210> SEQ ID NO 23
<211> LENGTH: 2133
<212> TYPE: DNA
<213> ORGANISM: Arabidopsis thaliana

<400> SEQUENCE: 23
atgtcctctt cttcttcttc ttctacttcc atgattgatt tgatggctgc catcatcaag    60
ggtgaaccag tcattgtctc tgacccagcc aacgcttctg cttacgaatc cgttgctgct   120
gaattgtcct ccatgttgat tgaaaacaga caattcgcta tgattgtcac tacttccatt   180
gctgtcttga ttggttgtat cgtcatgttg gtctggagaa gatccggttc cggtaactcc   240
aagagagttg aaccattgaa gccattagtc atcaagccaa gaagaagaa aattgatgac   300 ggtagaaaga aggtcaccat cttctttggt actcaaaccg gtactgctga aggttttgct   360
aaggctttgg gtgaagaagc caaagctaga tacgaaaaga ccagattcaa gatcgttgac   420
```

```
ttggacgact acgctgctga tgacgacgaa tacgaagaaa agttgaagaa ggaagatgtt       480
gccttcttct tcttggctac ttacggtgat ggtgaaccaa ctgacaatgc tgccagattc       540
tacaaatggt tcaccgaagg taacgacaga ggtgaatggt taaagaactt gaaatacggt       600
gttttcggtc taggtaacag acaatacgaa cacttcaaca aggttgccaa ggttgtcgat       660
gacatcttgg ttgaacaagg tgctcaaaga ttagtccaag tcggtttggg tgatgatgac       720
caatgtatcg aagatgactt cactgcttgg agagaagctt gtggccaga attggacacc        780 atcttaagag aagaaggtga taccgctgtt gccacccat acactgctgc tgttttggaa        840
tacagagttt ctatccacga ctctgaagat gccaagttca cgacatcaa catggctaac        900 ggtaacggtt acactgtttt cgacgctcaa cacccataca aggccaatgt tgctgtcaag       960
agagaattgc acactccaga atctgatcgt tcttgtatcc acttggaatt tgacattgct       1020
ggttctggtt tgacctacga aaccggtgac cacgtcggtg tcttatgtga caacttgtct       1080
gaaactgtcg atgaagcttt gagattattg gacatgtctc cagacactta tttctccttg       1140
catgctgaaa aggaagatgg tactccaatt tcttcttcct tgcctcctcc attcccacca       1200
tgtaacttga aaccgctttt aaccagatac gcttgtttgc tatcctctcc aaagaagtcc       1260
gctttggttg ctttggctgc tcacgcttct gacccaactg aagctgaaag attgaaacat       1320
ttggcttccc cagctggtaa ggatgaatac tccaaatggg ttgttgaatc tcaaagatct       1380
ttgttggaag tcatgctgaa attcccatct gccaagccac cattgggtgt tttcttcgcc       1440
ggtgttgctc caagattgca accaagattt tactccatct cttcttctcc aaagattgct       1500
gaaaccagaa ttcacgttac ctgtgccttg gtctacgaaa agatgccaac cggtagaatt       1560
cacaagggtg tttgttccac ctggatgaag aacgctgttc catacgaaaa gtctgaaaac       1620
tgttcttctg ctccaatctt cgtccgtcaa tccaacttca gttgccatc tgactccaag       1680 gtcccaatca tcatgatcgg tccaggtact ggtttagctc cattcagagg tttcttgcaa       1740
gaaagattgg ccttagttga atctggtgtc gaattgggtc cttctgtttt gttcttcggt       1800
tgtagaaacc gtcgtatgga cttcatctac gaagaagaat tgcaaagatt tgtcgaatct       1860
ggtgctttgg ctgaattgtc cgttgctttc tctcgtgaag gtccaaccaa agaatacgtt       1920
caacacaaga tgatggacaa agcctccgac atctggaaca tgatctccca aggtgcttac       1980
ttgtacgttt gtggtgatgc taaaggtatg gccagagatg tccacagatc tttacatacc       2040
attgcccaag aacaaggttc catggactcc accaaggctg aaggtttcgt taagaacttg       2100
caaacttctg gtcgttactt gagagatgtt tgg                                    2133
```

<210> SEQ ID NO 24
<211> LENGTH: 301
<212> TYPE: DNA
<213> ORGANISM: Artificial sequence
<220> FEATURE:
<223> OTHER INFORMATION: Sc Pdc1 terminator

<400> SEQUENCE: 24

```
agcgatttaa tctctaatta ttagttaaag ttttataagc attttatgt aacgaaaaat        60 aaattggttc atattattac tgcactgtca cttaccatgg aaagaccaga caagaagttg       120
ccgacagtct gttgaattgg cctggttagg cttaagtctg ggtccgcttc tttacaaatt       180
tggagaattt ctcttaaacg atatgtatat tctttcgtt ggaaaagatg tcttccaaaa        240 aaaaaccga tgaattagtg gaaccaagga aaaaaaaga ggtatccttg attaaggaac         300
a                                                                      301
```

<210> SEQ ID NO 25
<211> LENGTH: 1000
<212> TYPE: DNA
<213> ORGANISM: Artificial sequence
<220> FEATURE:
<223> OTHER INFORMATION: K1 prom 3 promoter

<400> SEQUENCE: 25

| | | |
|---|---|---|
| gagcctgtcc aagcaaatgc cttctcataa atggtgccaa agacccgcaa gcccaaagca | 60 |
| attaccccc aaaaagaaat gatatagtgc aagatacgta tatgaccatg acttgactag | 120 |
| gtgaaacagt gcagaaacag ccgcacaaaa gcagccctaa ccctcagagt cgattttact | 180 |
| cttttcaggta ataaagcctc gacatcaatt ttagacagaa gccaggctgg cctcgagatt | 240 |
| atagccatag gcaagcaaga ggagagaagg ggaggccccc catgggggc ctccccccg | 300 |
| ctgtcaaggt ttggcagaac ctagcttcat taggccacta gcccagccta aaacgtcaac | 360 |
| gggcaggagg aacactccca caagacggcg tagtattctc gattcataac cattttctca | 420 |
| atcgaattac acagaacaca ccgtacaaac ctctctatca taactactta atagtcacac | 480 |
| acgtactcgt ctaaatacac atcatcgtcc tacaagttca tcaaagtgtt ggacagacaa | 540 |
| ctataccagc atggatctct tgtatcggtt cttttctccc gctctctcgc aataacaatg | 600 |
| aacactgggt caatcatagc ctacacaggt gaacagagta gcgtttatac agggtttata | 660 |
| cggtgattcc tacggcaaaa attttcatt tctaaaaaaa aaagaaaaa ttttctttc | 720 |
| caacgctaga aggaaaagaa aaatctaatt aaattgattt ggtgattttc tgagagttcc | 780 |
| cttttttcata tatcgaattt tgaatataaa aggagatcga aaaattttt ctattcaatc | 840 |
| tgttttctgg ttttatttga tagttttttt gtgtattatt attatggatt agtactggtt | 900 |
| tatatggggtt tttctgtata acttcttttt attttagttt gtttaatctt attttgagtt | 960 |
| acattatagt tccctaactg caagagaagt aacattaaaa | 1000 |

<210> SEQ ID NO 26
<211> LENGTH: 1443
<212> TYPE: DNA
<213> ORGANISM: Stevia rebaudiana

<400> SEQUENCE: 26

| | | |
|---|---|---|
| atggacgcta tggccaccac tgaaaagaag cctcacgtta tctttattcc attcccagct | 60 |
| caatctcata tcaaggctat gttgaaattg gctcaattat tgcaccacaa gggtttgcaa | 120 |
| atcacttttg tcaacaccga cttcattcac aaccaattct tggaatcttc tggtcctcac | 180 |
| tgtttggacg gtgctccagg tttcagattc gaaaccattc cagatggtgt tcccactct | 240 |
| ccagaagcct ccatcccaat cagagaatcc ttgttgagat ctattgaaac caacttcttg | 300 |
| gaccgtttca tcgatttggt taccaaattg ccagacccac caacctgtat catttctgac | 360 |
| ggtttcttgt ccgttttcac catcgatgct gccaagaaat tgggtattcc agtcatgatg | 420 |
| tactggactt tggctgcttg tggtttcatg ggtttctacc atattcactc tttgattgaa | 480 |
| aagggtttcg ctccattaaa ggatgcttct tacttgacca acggttactt ggacaccgtc | 540 |
| attgactggg ttccaggtat ggaaggtatc agattgaaag atttcccatt ggactggtct | 600 |
| actgacttga tgacaaggt cttgatgttc actactgaag ctccacaaag atctcataag | 660 |
| gtttctcacc acatcttcca cactttcgat gaattagaac catctatcat caagactcta | 720 |
| tccttgagat acaaccatat ctacaccatt ggtccattac aattgttgtt ggaccaaatc | 780 |

```
ccagaagaaa agaagcaaac cggtatcact tctttgcacg gttactcttt agtcaaggaa      840
gaaccagaat gtttccaatg gttacaatcc aaggaaccaa actctgttgt ctacgttaac      900
tttggttcca ccactgttat gtccttggaa gatatgactg aatttggttg gggtttggct      960
aactctaacc actacttctt atggatcatc agatctaact tggtcattgg tgaaaacgcc     1020
gttttgcctc cagaattgga agaacacatc aagaagagag gtttcattgc ttcctggtgt     1080
tctcaagaaa aggtcttgaa gcacccatct gttggtggtt tcttgaccca ctgtggttgg     1140
ggttccacca ttgaatccct atctgctggt gttccaatga tctgttggcc atactcctgg     1200
gaccaattga ctaactgtcg ttacatctgt aaggaatggg aagttggttt ggaaatgggt     1260
actaaggtca agagagatga agtcaagaga ttagtccaag aattgatggg tgaaggtggt     1320
cacaagatga gaaacaaagc caaggactgg aaggaaaagg ccagaattgc tattgctcca     1380
aacggttctt cctccttgaa catcgataaa atggttaagg aaatcactgt cttggctcga     1440
aac                                                                  1443

<210> SEQ ID NO 27
<211> LENGTH: 301
<212> TYPE: DNA
<213> ORGANISM: Artificial sequence
<220> FEATURE:
<223> OTHER INFORMATION: Sc TDH1 terminator

<400> SEQUENCE: 27
aataaagcaa tcttgatgag gataatgatt ttttttgaa tatacataaa tactaccgtt       60
tttctgctag attttgtgaa gacgtaaata agtacatatt acttttttaag ccaagacaag     120 attaagcatt aactttaccc ttttctcttc taagtttcaa tactagttat cactgtttaa     180
aagttatggc gagaacgtcg gcggttaaaa tatattaccc tgaacgtggt gaattgaagt     240
tctaggatgg tttaaagatt tttcctttttt gggaaataag taaacaatat attgctgcct     300
t                                                                    301

<210> SEQ ID NO 28
<211> LENGTH: 1000
<212> TYPE: DNA
<213> ORGANISM: Artificial sequence
<220> FEATURE:
<223> OTHER INFORMATION: Kl prom 2 promoter

<400> SEQUENCE: 28
gagcctgtcc aagcaaatgc cttctcataa atggtgccaa agaccgcaa gcccaaagca       60 attacccccc aaaaagaaat gatatagtgc aagatacgta tatgaccatg acttgactag     120
gtgaaacagt gcagaaacag ccgcacaaaa gcagccctaa ccctcagagt cgatttttact    180 cttttcaggta ataaagcctc gacatcaatt ttagacagaa gccaggctgg cctcgagatt    240
atagccatag gcaagcaaga ggagagaagg ggaggccccc catgggggc ctcccccccg      300 ctgtcaaggt ttggcagaac ctagcttcat taggccacta gcccagccta aaacgtcaac    360
gggcaggagg aacactccca caagacggcg tagtattctc gattcataac catttttctca   420 atcgaattac acagaacaca ccgtacaaac ctctctatca taactactta atagtcacac    480
acgtactcgt ctaaatacac atcatcgtcc tacaagttca tcaaagtgtt ggacagacaa    540
ctataccagc atggatctct tgtatcggtt cttttctccc gctctctcgc aataacaatg    600
aacactgggt caatcatagc ctacacaggt gaacagagta gcgttatac agggtttata   660 cggtgattcc tacggcaaaa attttcatt tctaaaaaaa aaagaaaaa ttttctttc       720
```

| | |
|---|---|
| caacgctaga aggaaaagaa aaatctaatt aaattgattt ggtgattttc tgagagttcc | 780 |
| cttttcata tatcgaattt tgaatataaa aggagatcga aaaattttt ctattcaatc | 840 |
| tgttttctgg ttttatttga tagtttttt gtgtattatt attatggatt agtactggtt | 900 |
| tatatgggtt tttctgtata acttctttt attttagttt gtttaatctt attttgagtt | 960 |
| acattatagt tccctaactg caagagaagt aacattaaaa | 1000 |

<210> SEQ ID NO 29
<211> LENGTH: 1380
<212> TYPE: DNA
<213> ORGANISM: Stevia rebaudiana

<400> SEQUENCE: 29

| | |
|---|---|
| atggctgaac aacaaaagat caagaaatct ccacacgtct tgttgattcc attcccattg | 60 |
| caaggtcaca tcaacccatt catccaattc ggtaagagat tgatttccaa gggtgtcaag | 120 |
| accactttag tcaccactat tcacacttta aactccactt taaaccactc taacactact | 180 |
| accacctcta ttgaaatcca agccatttct gacggttgtg acgaaggtgg tttcatgtct | 240 |
| gctggtgaat cttacttgga aactttcaag caagtcggtt ccaagtcttt ggctgatttg | 300 |
| atcaagaaat tgcaatccga aggtactacc atcgatgcta tcatctacga ctccatgact | 360 |
| gaatgggttt tggatgttgc cattgaattt ggtattgacg tgggttcttt cttcacccaa | 420 |
| gcctgtgttg ttaactcttt gtactaccac gtccacaagg gtttgatctc tctaccatta | 480 |
| ggtgaaaccg tttccgtccc aggttttcca gtcttgcaaa gatgggaaac tccattgatc | 540 |
| ttacaaaacc atgaacaaat ccaatctcca tggtcccaaa tgttgtttgg tcaattcgct | 600 |
| aacattgacc aagctagatg ggttttcacc aactctttct acaagttgga agaagaagtc | 660 |
| attgaatgga ccagaaagat ctggaacttg aaggttatcg gtccaactct accatccatg | 720 |
| tacttggaca gagattgga tgacgacaag gacaacggtt caacttgta caaggctaac | 780 |
| catcacgaat gtatgaactg gttggatgac aagccaaagg aatctgttgt ttacgttgct | 840 |
| ttcggttctt tggtcaagca tggtccagaa caagttgaag aaatcaccag gctttgatt | 900 |
| gactccgatg ttaacttctt atgggttatc aagcacaagg aagaaggtaa attgccagaa | 960 |
| aacttgtctg aagttatcaa gaccggtaag ggtttgattg ttgcttggtg taagcaattg | 1020 |
| gatgttttgg ctcacgaatc cgtcggttgt ttcgtcactc actgtggttt caactctact | 1080 |
| ttggaagcta tctccttggg tgttccagtt gttgccatgc ctcaattctc tgaccaaacc | 1140 |
| accaacgcca aattgttgga tgaaatcttg ggtgtcggtt ccgtgtcaa ggctgatgaa | 1200 |
| aacggtattg ttagaagagg taacttagct tcctgtatca agatgatcat ggaagaagaa | 1260 |
| cgtggtgtca ttatcagaaa gaatgctgtc aaatggaagg acttggctaa ggttgctgtc | 1320 |
| cacgaaggtg gttcctctga caatgacatt gttgaatttg tctctgaatt gatcaaagcg | 1380 |

<210> SEQ ID NO 30
<211> LENGTH: 1374
<212> TYPE: DNA
<213> ORGANISM: Stevia rebaudiana

<400> SEQUENCE: 30

| | |
|---|---|
| atggaaaaca agactgaaac cactgttaga agaagaagaa gaatcatctt attcccagtt | 60 |
| ccattccaag gtcacattaa cccaatcttg caattggcta acgtcttata ctccaagggt | 120 |
| ttctccatca ccatcttcca caccaacttc aacaaaccta aaacttccaa ctacccacac | 180 |

```
ttcaccttca gatttatctt ggacaacgac ccacaagatg aaagaatttc taacttgcca      240
acccatggtc cattggccgg tatgagaatt ccaatcatca acgaacacgg tgctgacgaa      300
ttgagaagag aattggaatt gttgatgttg gcttctgaag aagatgaaga agtctcttgt      360
ttgatcactg atgctttatg gtactttgct caatctgttg ctgactcttt gaacttgaga      420
agattagtct tgatgacctc ttcttttgttc aacttccacg ctcacgtttc tctaccacaa     480
tttgatgaat tgggttactt ggacccagat gacaagacca gattggaaga acaagcctcc     540
ggtttcccaa tgttgaaggt caaggatatc aagtctgcct actccaactg gcaaatcttg     600
aaggaaattt tgggtaagat gatcaagcaa accaaggctt cttctggtgt catctggaac     660
tccttcaagg aattggaaga atctgaattg gaaaccgtca tcagagaaat tccagctcca     720
tctttcttga ttccattacc aaagcatttg actgcttcct cctcttctct attggaccac     780
gacagaactg ttttccaatg gttggaccaa caaccaccat cttccgtctt atacgtttcc     840
tttggttcca cttctgaagt tgacgaaaag gacttcttgg aaaattgctcg tggtttggtt     900 gactccaagc aatctttctt atgggttgtc agaccaggtt tcgtcaaggg ttccacctgg     960
gttgaacctt tgccagacgg tttcttgggt gaaagaggta gaattgtcaa atgggttcca    1020
caacaagaag ttttggctca cggtgccatt ggtgctttct ggactcactc tggttggaac    1080
tctactttgg aatccgtttg tgaaggtgtt ccaatgattt tctctgactt cggtttggac    1140
caaccattga atgctcgtta catgtccgat gttttgaagg ttggtgtcta cttggaaaac    1200
ggttgggaac gtggtgaaat tgctaacgcc atcagaagag tcatggtcga tgaagaaggt    1260
gaatacatca gacaaaatgc tcgtgtcttg aaacaaaagg ctgatgtttc tttgatgaag    1320
ggtggttctt cttacgaatc tttggaatct ttggtttcct acatctccag tctc          1374
```

<210> SEQ ID NO 31
<211> LENGTH: 602
<212> TYPE: DNA
<213> ORGANISM: Artificial sequence
<220> FEATURE:
<223> OTHER INFORMATION: Sc Eno1 terminator

<400> SEQUENCE: 31

```
aagcttttga ttaagccttc tagtccaaaa acacgttttt tttgtcattt atttcatttt       60
cttagaatag tttagtttat tcatttttata gtcacgaatg ttttatgatt ctatataggg      120
ttgcaaacaa gcattttttca ttttatgtta aaacaatttc aggtttacct tttattctgc     180
ttgtggtgac gcgtgtatcc gcccgctctt tggtcaccc atgtatttaa ttgcataaat      240
aattcttaaa agtggagcta gtctatttct atttacatac ctctcatttc tcatttcctc     300
caagcttttg attaagcctt ctagtccaaa aacacgtttt tttgtcatt tatttcattt      360 tcttagaata gtttagttta ttcatttttat agtcacgaat gttttatgat tctatatagg    420
gttgcaaaca agcattttttc attttatgtt aaaacaattt caggtttacc ttttattctg    480
cttgtggtga cgcgtgtatc cgcccgctct tttggtcacc catgtattta attgcataaa     540
taattcttaa agtggagct agtctatttc tatttacata cctctcatt ctcatttcct       600 cc                                                                    602
```

<210> SEQ ID NO 32
<211> LENGTH: 600
<212> TYPE: DNA
<213> ORGANISM: Artificial sequence
<220> FEATURE:
<223> OTHER INFORMATION: Sc_TDH3.pro

<400> SEQUENCE: 32

```
ttagtcaaaa aattagcctt ttaattctgc tgtaacccgt acatgcccaa aataggggc        60
gggttacaca gaatatataa catcgtaggt gtctgggtga acagtttatt cctggcatcc      120
actaaatata atggagcccg cttttaagc tggcatccag aaaaaaaaag aatcccagca      180
ccaaaatatt gttttcttca ccaaccatca gttcataggt ccattctctt agcgcaacta      240
cagagaacag gggcacaaac aggcaaaaaa cgggcacaac ctcaatggag tgatgcaacc      300
tgcctggagt aaatgatgac acaaggcaat tgacccacgc atgtatctat ctcattttct      360
tacaccttct attaccttct gctctctctg atttggaaaa agctgaaaaa aaaggttgaa      420
accagttccc tgaaattatt ccctacttg actaataagt atataaagac ggtaggtatt      480
gattgtaatt ctgtaaatct atttcttaaa cttcttaaat tctacttta tagttagtct      540
tttttttagt tttaaaacac caagaactta gtttcgaata aacacacata aacaaacaaa      600
```

<210> SEQ ID NO 33
<211> LENGTH: 4248
<212> TYPE: DNA
<213> ORGANISM: Artificial sequence
<220> FEATURE:
<223> OTHER INFORMATION: ALNQ_007_38000 CpO for S. cerevisiae

<400> SEQUENCE: 33

```
atgtctgctt tgaacaccga tgctttggaa tctcaaccag acttcaagtt ccaaagacaa        60
aagagattga tgtctccatt tatgtctaag aaggttccac caatcccaac caaagaagaa      120
agaaagccat acggtgaata ccacaccaac atcttattca gaattatgtt ctggtggttg      180
aaccctatct tgaacgtcgg ttacaagaga cttgactg aacaagactt gttctatttg      240
gacaactccc aaaccatgga cactttatac gaaactttca atcccactt gaagaccact      300
atcgaaaagt ccatgaagaa gtacttgcaa gaaaaatact ctaaggaagg taagacctac      360
gacccatctt ccattccaac tgctgaagat ttgaaggact tccaaattcc aatctacgct      420
atccattgt gtttattcaa gactttgtac tggcaatact cttgggtaa tttgtacaag      480
gtcttgtctg actgtactc tgctactacc ccattgttgc aaaagaagtt aatcaacttc      540
gttcaaatga agtctttcac cgcttttggg tctaccggta agggcgttgg ttacgccatc      600
ggtgtgtgtt tgatgatctt cttccaagcc attaccgtca accatgcttt ccacaacttg      660
caaatttgtg gtgccaaatc caaggctatt ttgactagaa tgttgttgga caagtctatg      720
tctgttgatg ctagaggtaa ccacttcttc ccagcctcca aggtccaatc tatgatctct      780
accgatttga acagagtcga tttggccatc ggttcttcc cattcgcttt gacttgtgtt      840
tttccaattg ctatctgtat cggttttgtta atctggaacg ttggtgtctc cgccttggtt      900
ggtattgcca tcttcgttgc taacgttggt ttgttggctg tttccatccc aagattgatg      960
agattcagaa tcaaagctat ggttttacc gacaagcgtg tcactttgat gaaggaattg     1020
ttgaagaact tcaagatgat caagttctac tcttgggaaa actcttacgc tagaagaatc     1080
caagatgctc gttcaagga aatgaagttg atcttgtcat acaatctttt aagaaacatt     1140
gtcatgtccg tttctttcgc catgccaact ttggcttcta tggctacttt ctgtaccgct     1200
ttcgatatca cttctggtaa gaacgctgct tccttgttct cctctttgtc tttattccaa     1260
gttttatcca tgcaattcat gttggctcca gttgccttaa acaccgctgc tgacatgatg     1320
gtttctatga agaaattcaa ccagttcttg gctcacgctg atttggatcc tgaacaatac     1380
```

```
agaatcgaag aattccacga tgataagttg gccgttaagg ttgacaacgc caccttcgaa   1440
tgggacacct tcgatgatga caaggtcgaa gacccagctt tagaatttga aaaacaagat   1500
aatgactcct tggaaaaagt ttcctcccac aacaccgttg actacgactc tactgaaaag   1560
atcagaaacg acacttcttc tatcgattcc accaagattt tggaaaagac tgctttccct   1620
ggtttgagaa acatcaactt ggaaatcaaa aagggtgaat tcgttgttgt taccggttcc   1680
attggtgctg gtaaatcctc tttgctacaa gctatctctg gtttgatgaa agagtctcc    1740
ggtaaggttt acgtcgatgg tgacttgttg ttgtgtggtt acccttgggt tcaaaacgct   1800
actatcagag acaacatctt gttcggttta ccattcgacc aagaaaagta cgaccaagtt   1860
gtttacgctt gttctttgca atctgacttc aaccaattcc aaggtggtga catgactgaa   1920
gttggtgaaa gaggtattac cttgtctggt ggtcaaaagg ctagaattaa cttggccaga   1980
tccgtctacg ctgacaagga cattattttg ttggatgacg ttttgtctgc tgtcgatgct   2040
aaggttggta gacatattgt cgatacctgt ttgttgggtt tattgaagga caagacccgt   2100
atcatggcta cccaccaatt gtctttaatt gactctgctg acagaatgat tttcttgaac   2160
ggtgatggtt ctattgactg tggtactatt ccgaattaa aggaccgtaa cgaaaaattg    2220
aacgaattgt tgtctcacca aaaggacaag gccaacgact ctgatgaaga attggaattg   2280
caagaagaaa tcgaatctaa ggaacaacac ttgaaggaag attttgtctga agttaagcac   2340
gaaatcaagg aagaacaaaa gaagatggaa atctccggtg atgtcggtga agaattcgaa   2400
cacgctgacg aacacaagga aattgttaga attattggtg atgaggaaag agctgtcaac   2460
gctttgaagg ccgatgtcta catcaactac gctaaattgg ccttcggtaa gttgggtcta   2520
ttctccttga tgttgttcgt caccgttgct gctttgcaaa cttactgtaa catgttcact   2580
aacacctggt tatccttctg gattgaagaa aagttccatg gtagatccaa gtccttctac   2640
atgggtattt acatcatgtt cgctttcttg tacactttct tcctagctgc ctttttctac   2700
tctatgtgtt acttctgtaa cagagcttcc aagtatttga actacaaggc ctccgaaaag   2760
attttgcacg ttccaatgtc tttcatggac attttctcca tcggtcgtgt tttgaataga   2820
ttcaccaagg acaccgatgt cttggacaac gaaattttgg accaattcag acaattcttg   2880
tccccattct gtaacgccat tggtactatc gtcttgtgca tcatctacat tccatggttc   2940
gctattgccg tcccattgat tgtcactttc tacgtcttgg tcgccaacta ctaccaagct   3000
tctgctcgtg aaatcaagag attggaagct gtcaagcgtt ctttggtctt tggtcacttc   3060
aacgaagctc tatctggtaa ggaaactatc aaggcttaca gagctatcga cagagtcaag   3120
caaagattga acaaattgat cgatgggcaa aacgaagctt actttttgac cattgttaac   3180
caaagatggt gggtgccaa tttgtctatc ttgtctttct gtatggtttt catcatctct    3240
ttcttgtgtg tcttcagagt cttcaacatt tctgctgctt ccactggttt attattgact   3300
tacgttatca acttgaccaa taccatcact atgatgatga gagctatgac ccaagtcgaa   3360
aacgaattta actccgttga gagattgaac cactacgctt cgacttagt ccaagaagct     3420
ccatacgaaa tcccagaaaa cgatccacca aagactggc caaagtacgg tgaaatcatt    3480
ttcaaggatg tttccatgag atacagacca gaattgccat cgttttgaa gaacatcaac     3540
ctatccatcg gtaagggtga aaagattggt ttctgtggta aaccggtgc cggtaagtct     3600
actttcatga cttgtttgta cagaatttct gagttcgaag gtaccatcgt tatcgatgac   3660
gtcgatatct ccaagttggg tttgcacaaa ttgcgttcta agttgactat tatcccacaa   3720
gacccagtct tattcgttgg ttccatcaga gaaaacttag acccatttgg tgaatactct   3780
```

```
gacgaagaat tatgggaagc tttgaccatc tccggtttga tcaacaaaga agacttgaac    3840
gaggttaaga agcaaaatga aaatgacgac aacttgaaca agttccactt gattagaatg    3900
gtcgaagatg atggtgttaa cttctccatc ggtgaacgtc aattgattgc tctagccaga    3960
gctttggtca gaaagactaa gattttgatc ttggacgaag ctacttcttc tgtcgattac    4020
gctactgact ccagaattca aaagaccatt gctactgaat cgacgactg  tatgatcttg    4080 tgtatcgctc acagattaaa caccatcttg aactacgaca agatcgtcgt catggacaaa    4140
ggtgaaatcg ttgaattcga taagccaaga tctttgttca tgagagaaga aggtgttttc    4200
agatccatgt gtgaacaagc taacatcacc attgaagatt ttccataa                 4248

<210> SEQ ID NO 34
<211> LENGTH: 4248
<212> TYPE: DNA
<213> ORGANISM: Issatchenkia orientalis

<400> SEQUENCE: 34
atgtcggcgc ttaatacgga tgccttagag agtcagcctg acttcaagtt ccagagacaa      60
aagaggttga tgtctccatt tatgtcgaaa aaagtgcctc ctatacctac aaaggaagag     120
aggaaaccct atggggagta ccatacaaac atactatttc gtattatgtt ttggtggttg     180
aatcctattt tgaatgtcgg gtacaaaagg acattgactg aacaggattt attctatctt     240
gataatagcc agactatgga caccctctat gagaccttca aaagccatct aaagacgaca     300
attgagaaat caatgaaaaa ataccttcag gagaaataca gtaaagaggg gaagacatat     360
gacccaagta gtataccctac agctgaagac ttaaaagatt tccaaatacc catttatgca     420
atcccattgt gcttgttcaa aactctatac tggcagtata gtcttggtaa tctctacaaa     480
gtattatccg actgtacatc tgctacaaca ccttt attgc agaagaaact cattaatttt     540
gttcagatga aatcctttac cgcattagga agtacgggga aaggtgtagg gtacgccatc     600
ggtgtatgct tgatgatctt cttccaagca ataactgtca atcatgcctt tcataatttg     660
caaatctgtg gtgccaaatc taaggcgatt cttacgagaa tgttattgga taaatcaatg     720
tcagtcgatg ccagaggtaa tcatttttt  cctgctagta aagttcagag catgatatcc     780
acagatttga atagggtaga tttggctatt ggcttttttcc catttgcact acgtgtgta      840 tttccaattg ctatttgtat aggcttgctt atttggaacg ttggtgtgtc agcattagtg     900
ggaattgcca ttttcgttgc caatgtcggt ctcttagccg tttctatacc tagacttatg     960
cggttcagga taaaggccat ggtattcaca gacaagagag ttactttaat gaaagagctg    1020
ttaaaaaatt ttaaaatgat caagttctat agctgggaaa attcatacgc cagaaggatc    1080
caggatgcca gattcaagga gatgaaattg attttgtctt tacagtcttt aagaaatatt    1140
gtgatgtcag tttcatttgc tatgccgaca ttggcttcaa tggcaacatt ttgtactgcc    1200
tttgatatca caagtggtaa aaatgctgcc tctttattct cctctctttc tctcttccaa    1260
gttttatcaa tgcaattcat gttagcccca gttgccctta atactgctgc tgatatgatg    1320
gtgtcaatga aaaagttcaa tcaattttta gctcatgctg acttggatcc agagcagtat    1380
cgtatagaag aatttcacga cgataaattg gcggtgaaag ttgataatgc  cacttttgaa    1440
tgggatacgt ttgacgatga taaagttgaa gatcctgctc ttgaatttga aaaacaggac    1500
aatgacagtc ttgaaaaagt ttccagtcat aatacggtcg attatgacag taccgaaaag    1560
attagaaatg atacaagctc gatagattct accaaaatct tggagaaaac agcatttcct    1620
```

```
ggcctaagaa acataaatct agagattaag aaaggcgaat tgttgttgt tacaggtagt    1680
atcggtgctg gtaaatcatc ccttctccag gccatctcgg gattgatgaa aagagtatct   1740
ggtaaggttt atgttgatgg tgacttattg ctatgcggtt atccatgggt tcaaaatgct   1800
acgattcggg acaacatttt gtttggtttg ccatttgacc aagaaaagta cgaccaagtt   1860
gtttatgctt gttcattgca gagcgacttc aatcagttcc aaggtggtga catgaccgag   1920
gttggtgaac gaggtattac attatctggt ggtcaaaagg ctagaatcaa cttggcaaga   1980
tctgtatatg ctgacaagga tataatttta cttgatgatg ttttaagtgc tgttgatgcg   2040
aaggtgggtc gacatatcgt tgatacttgc cttcttggtt tgttaaagga taaaactaga   2100
attatggcaa ctcaccaact aagtttgatt gactctgcag atcgaatgat tttcctcaat   2160
ggggatggaa gtattgattg cggtaccatc tcagaattga agacagaaa tgaaaaactg    2220
aacgaacttt tgtctcatca aaaggataag gcaaatgact ccgacgaaga gttagaattg   2280
caagaagaaa tcgagtcgaa agaacaacat ctcaaagaag atttatctga ggtgaaacat   2340
gaaatcaaag aagaacagaa gaagatggaa ataagcggtg atgtaggaga gagtttgaa    2400
catgcagatg aacataaaga gattgttagg attattggtg atgaagaaag agccgtgaat   2460
gccctgaagg cggatgttta tatcaattat gctaaacttg catttggtaa actcggattg   2520
ttttcactga tgttgtttgt cacagttgct gctttacaga cttactgcaa tatgtttacc   2580
aacacatggt tatcttttg gatagaagaa aaattccacg gcagatccaa aagttttac    2640
atggggatct acattatgtt tgccttctta tacacatttt tccttgctgc attttctat    2700
tcaatgtgct atttctgcaa tagggcttcc aagtatctta attataaagc ttcagaaaaa   2760
atcttgcatg ttccaatgtc cttcatggat attctccaa ttggtcgagt tttgaataga   2820
tttacaaaag atactgatgt gttagataac gagatactag atcaatttag acagtttttg   2880
agtcccttct gcaatgctat cggtaccatt gttctatgta ttatttacat tccatggttt   2940
gcaattgctg ttccccttaat tgttacattt tatgttttgg ttgccaatta ctaccaagcc   3000
agcgctagag agatcaaaag gttagaagca gttaaaaggt cgttggtctt tggccatttc   3060
aatgaagcat tatccggaaa ggagacaatc aaagcttata gggcaatcga cagagtcaag   3120
caaaggttga acaaattgat tgatgggcag aacgaggctt attttctaac cattgttaac   3180
cagagatggt taggtgccaa tttatcgatc ttatcatttt gtatggtctt cattatctcg   3240
ttcttgtgtg ttttcagagt tttcaatatc agtgcagcgt cgactggttt actttaacc   3300
tatgtcataa atttgacaaa taccattact atgatgatga gagctatgac gcaagttgaa   3360
aatgagttca attcagttga aagattaaac cattatgcct ttgatcttgt ccaggaggcc   3420
ccttatgaga ttcctgagaa tgatccaccc caggactggc ctaagtatgg tgaaattatt   3480
ttcaaagatg ttagtatgag atatagacca gaattaccat ttgttttgaa gaatatcaac   3540
ttaagtattg ggaaaggtga gaaaattgga ttttgtggaa gaaccggtgc tggtaagtct   3600
acgttcatga cttgcttgta caggatttcc gaatttgaag gaactattgt tattgatgat   3660
gttgatatca gtaaattggg tttacataaa ctaagatcca aattaactat tattccacaa   3720
gatccagtgt tatttgtcgg ttcgatccga gagaatctgg atccatttgg cgagtattct   3780
gatgaagaat tgtgggaggc acttacaatt tccggtttga tcaacaagga agatctaaac   3840
gaagtaaaaa aacagaacga aaatgatgat aacttaaaca aattccacct tatcagaatg   3900
gtggaggatg atggtgtgaa tttctctatt ggagagagac agttgattgc acttgccaga   3960
gctttggtta ggaaaaccaa aattctaatc ttagatgagg caacatcaag tgttgactat   4020
```

```
gccaccgatt caagaatcca aaagaccatt gccaccgaat tcgacgactg tatgatactg    4080
tgtattgctc acagattgaa tacgattcta aactacgata agattgtcgt tatggataag    4140
ggtgagattg ttgagtttga taaaccaaga tcattgttta tgagggagga agggtctttt    4200
aggtctatgt gtgagcaggc aaatatcaca atcgaagatt tcccttaa                4248
```

<210> SEQ ID NO 35
<211> LENGTH: 1415
<212> TYPE: PRT
<213> ORGANISM: Issatchenkia orientalis

<400> SEQUENCE: 35

```
Met Ser Ala Leu Asn Thr Asp Ala Leu Glu Ser Gln Pro Asp Phe Lys
1               5                   10                  15

Phe Gln Arg Gln Lys Arg Leu Met Ser Pro Phe Met Ser Lys Lys Val
            20                  25                  30

Pro Pro Ile Pro Thr Lys Glu Glu Arg Lys Pro Tyr Gly Glu Tyr His
        35                  40                  45

Thr Asn Ile Leu Phe Arg Ile Met Phe Trp Trp Leu Asn Pro Ile Leu
    50                  55                  60

Asn Val Gly Tyr Lys Arg Thr Leu Thr Glu Gln Asp Leu Phe Tyr Leu
65                  70                  75                  80

Asp Asn Ser Gln Thr Met Asp Thr Leu Tyr Glu Thr Phe Lys Ser His
                85                  90                  95

Leu Lys Thr Thr Ile Glu Lys Ser Met Lys Lys Tyr Leu Gln Glu Lys
            100                 105                 110

Tyr Ser Lys Glu Gly Lys Thr Tyr Asp Pro Ser Ile Pro Thr Ala
        115                 120                 125

Glu Asp Leu Lys Asp Phe Gln Ile Pro Ile Tyr Ala Ile Pro Leu Cys
    130                 135                 140

Leu Phe Lys Thr Leu Tyr Trp Gln Tyr Ser Leu Gly Asn Leu Tyr Lys
145                 150                 155                 160

Val Leu Ser Asp Cys Thr Ser Ala Thr Thr Pro Leu Leu Gln Lys Lys
                165                 170                 175

Leu Ile Asn Phe Val Gln Met Lys Ser Phe Thr Ala Leu Gly Ser Thr
            180                 185                 190

Gly Lys Gly Val Gly Tyr Ala Ile Gly Val Cys Leu Met Ile Phe Phe
        195                 200                 205

Gln Ala Ile Thr Val Asn His Ala Phe His Asn Leu Gln Ile Cys Gly
    210                 215                 220

Ala Lys Ser Lys Ala Ile Leu Thr Arg Met Leu Leu Asp Lys Ser Met
225                 230                 235                 240

Ser Val Asp Ala Arg Gly Asn His Phe Phe Pro Ala Ser Lys Val Gln
                245                 250                 255

Ser Met Ile Ser Thr Asp Leu Asn Arg Val Asp Leu Ala Ile Gly Phe
            260                 265                 270

Phe Pro Phe Ala Leu Thr Cys Val Phe Pro Ile Ala Ile Cys Ile Gly
        275                 280                 285

Leu Leu Ile Trp Asn Val Gly Val Ser Ala Leu Val Gly Ile Ala Ile
    290                 295                 300

Phe Val Ala Asn Val Gly Leu Leu Ala Val Ser Ile Pro Arg Leu Met
305                 310                 315                 320

Arg Phe Arg Ile Lys Ala Met Val Phe Thr Asp Lys Arg Val Thr Leu
                325                 330                 335
```

```
Met Lys Glu Leu Leu Lys Asn Phe Lys Met Ile Lys Phe Tyr Ser Trp
            340                 345                 350

Glu Asn Ser Tyr Ala Arg Arg Ile Gln Asp Ala Arg Phe Lys Glu Met
            355                 360                 365

Lys Leu Ile Leu Ser Leu Gln Ser Leu Arg Asn Ile Val Met Ser Val
            370                 375                 380

Ser Phe Ala Met Pro Thr Leu Ala Ser Met Ala Thr Phe Cys Thr Ala
385                 390                 395                 400

Phe Asp Ile Thr Ser Gly Lys Asn Ala Ala Ser Leu Phe Ser Ser Leu
            405                 410                 415

Ser Leu Phe Gln Val Leu Ser Met Gln Phe Met Leu Ala Pro Val Ala
            420                 425                 430

Leu Asn Thr Ala Ala Asp Met Met Val Ser Met Lys Lys Phe Asn Gln
            435                 440                 445

Phe Leu Ala His Ala Asp Leu Asp Pro Glu Gln Tyr Arg Ile Glu Glu
            450                 455                 460

Phe His Asp Asp Lys Leu Ala Val Lys Val Asp Asn Ala Thr Phe Glu
465                 470                 475                 480

Trp Asp Thr Phe Asp Asp Lys Val Glu Asp Pro Ala Leu Glu Phe
            485                 490                 495

Glu Lys Gln Asp Asn Asp Ser Leu Glu Lys Val Ser Ser His Asn Thr
            500                 505                 510

Val Asp Tyr Asp Ser Thr Glu Lys Ile Arg Asn Asp Thr Ser Ser Ile
            515                 520                 525

Asp Ser Thr Lys Ile Leu Glu Lys Thr Ala Phe Pro Gly Leu Arg Asn
            530                 535                 540

Ile Asn Leu Glu Ile Lys Lys Gly Glu Phe Val Val Thr Gly Ser
545                 550                 555                 560

Ile Gly Ala Gly Lys Ser Ser Leu Leu Gln Ala Ile Ser Gly Leu Met
                565                 570                 575

Lys Arg Val Ser Gly Lys Val Tyr Val Asp Gly Asp Leu Leu Leu Cys
            580                 585                 590

Gly Tyr Pro Trp Val Gln Asn Ala Thr Ile Arg Asp Asn Ile Leu Phe
            595                 600                 605

Gly Leu Pro Phe Asp Gln Glu Lys Tyr Asp Gln Val Val Tyr Ala Cys
            610                 615                 620

Ser Leu Gln Ser Asp Phe Asn Gln Phe Gln Gly Gly Asp Met Thr Glu
625                 630                 635                 640

Val Gly Glu Arg Gly Ile Thr Leu Ser Gly Gln Lys Ala Arg Ile
                645                 650                 655

Asn Leu Ala Arg Ser Val Tyr Ala Asp Lys Asp Ile Ile Leu Leu Asp
            660                 665                 670

Asp Val Leu Ser Ala Val Asp Ala Lys Val Gly Arg His Ile Val Asp
            675                 680                 685

Thr Cys Leu Leu Gly Leu Leu Lys Asp Lys Thr Arg Ile Met Ala Thr
            690                 695                 700

His Gln Leu Ser Leu Ile Asp Ser Ala Asp Arg Met Ile Phe Leu Asn
705                 710                 715                 720

Gly Asp Gly Ser Ile Asp Cys Gly Thr Ile Ser Glu Leu Lys Asp Arg
                725                 730                 735

Asn Glu Lys Leu Asn Glu Leu Leu Ser His Gln Lys Asp Lys Ala Asn
            740                 745                 750
```

```
Asp Ser Asp Glu Glu Leu Glu Leu Gln Glu Ile Glu Ser Lys Glu
            755                 760                 765
Gln His Leu Lys Glu Asp Leu Ser Glu Val Lys His Glu Ile Lys Glu
        770                 775                 780
Glu Gln Lys Lys Met Glu Ile Ser Gly Asp Val Gly Glu Glu Phe Glu
785                 790                 795                 800
His Ala Asp Glu His Lys Glu Ile Val Arg Ile Ile Gly Asp Glu Glu
                805                 810                 815
Arg Ala Val Asn Ala Leu Lys Ala Asp Val Tyr Ile Asn Tyr Ala Lys
            820                 825                 830
Leu Ala Phe Gly Lys Leu Gly Leu Phe Ser Leu Met Leu Phe Val Thr
            835                 840                 845
Val Ala Ala Leu Gln Thr Tyr Cys Asn Met Phe Thr Asn Thr Trp Leu
850                 855                 860
Ser Phe Trp Ile Glu Glu Lys Phe His Gly Arg Ser Lys Ser Phe Tyr
865                 870                 875                 880
Met Gly Ile Tyr Ile Met Phe Ala Phe Leu Tyr Thr Phe Phe Leu Ala
                885                 890                 895
Ala Phe Tyr Ser Met Cys Tyr Phe Cys Asn Arg Ala Ser Lys Tyr
            900                 905                 910
Leu Asn Tyr Lys Ala Ser Glu Lys Ile Leu His Val Pro Met Ser Phe
        915                 920                 925
Met Asp Ile Ser Pro Ile Gly Arg Val Leu Asn Arg Phe Thr Lys Asp
        930                 935                 940
Thr Asp Val Leu Asp Asn Glu Ile Leu Asp Gln Phe Arg Gln Phe Leu
945                 950                 955                 960
Ser Pro Phe Cys Asn Ala Ile Gly Thr Ile Val Leu Cys Ile Ile Tyr
                965                 970                 975
Ile Pro Trp Phe Ala Ile Ala Val Pro Leu Ile Val Thr Phe Tyr Val
            980                 985                 990
Leu Val Ala Asn Tyr Tyr Gln Ala Ser Ala Arg Glu Ile Lys Arg Leu
        995                 1000                1005
Glu Ala Val Lys Arg Ser Leu Val Phe Gly His Phe Asn Glu Ala
    1010                1015                1020
Leu Ser Gly Lys Glu Thr Ile Lys Ala Tyr Arg Ala Ile Asp Arg
    1025                1030                1035
Val Lys Gln Arg Leu Asn Lys Leu Ile Asp Gly Gln Asn Glu Ala
    1040                1045                1050
Tyr Phe Leu Thr Ile Val Asn Gln Arg Trp Leu Gly Ala Asn Leu
    1055                1060                1065
Ser Ile Leu Ser Phe Cys Met Val Phe Ile Ile Ser Phe Leu Cys
    1070                1075                1080
Val Phe Arg Val Phe Asn Ile Ser Ala Ala Ser Thr Gly Leu Leu
    1085                1090                1095
Leu Thr Tyr Val Ile Asn Leu Thr Asn Thr Ile Thr Met Met Met
    1100                1105                1110
Arg Ala Met Thr Gln Val Glu Asn Glu Phe Asn Ser Val Glu Arg
    1115                1120                1125
Leu Asn His Tyr Ala Phe Asp Leu Val Gln Glu Ala Pro Tyr Glu
    1130                1135                1140
Ile Pro Glu Asn Asp Pro Gln Asp Trp Pro Lys Tyr Gly Glu
    1145                1150                1155
Ile Ile Phe Lys Asp Val Ser Met Arg Tyr Arg Pro Glu Leu Pro
```

Phe Val Leu Lys Asn Ile Asn Leu Ser Ile Gly Lys Gly Glu Lys
1175                    1180                1185

Ile Gly Phe Cys Gly Arg Thr Gly Ala Gly Lys Ser Thr Phe Met
1190                    1195                1200

Thr Cys Leu Tyr Arg Ile Ser Glu Phe Glu Gly Thr Ile Val Ile
1205                    1210                1215

Asp Asp Val Asp Ile Ser Lys Leu Gly Leu His Lys Leu Arg Ser
1220                    1225                1230

Lys Leu Thr Ile Ile Pro Gln Asp Pro Val Leu Phe Val Gly Ser
1235                    1240                1245

Ile Arg Glu Asn Leu Asp Pro Phe Gly Glu Tyr Ser Asp Glu Glu
1250                    1255                1260

Leu Trp Glu Ala Leu Thr Ile Ser Gly Leu Ile Asn Lys Glu Asp
1265                    1270                1275

Leu Asn Glu Val Lys Lys Gln Asn Glu Asn Asp Asp Asn Leu Asn
1280                    1285                1290

Lys Phe His Leu Ile Arg Met Val Glu Asp Asp Gly Val Asn Phe
1295                    1300                1305

Ser Ile Gly Glu Arg Gln Leu Ile Ala Leu Ala Arg Ala Leu Val
1310                    1315                1320

Arg Lys Thr Lys Ile Leu Ile Leu Asp Glu Ala Thr Ser Ser Val
1325                    1330                1335

Asp Tyr Ala Thr Asp Ser Arg Ile Gln Lys Thr Ile Ala Thr Glu
1340                    1345                1350

Phe Asp Asp Cys Met Ile Leu Cys Ile Ala His Arg Leu Asn Thr
1355                    1360                1365

Ile Leu Asn Tyr Asp Lys Ile Val Val Met Asp Lys Gly Glu Ile
1370                    1375                1380

Val Glu Phe Asp Lys Pro Arg Ser Leu Phe Met Arg Glu Glu Gly
1385                    1390                1395

Val Phe Arg Ser Met Cys Glu Gln Ala Asn Ile Thr Ile Glu Asp
1400                    1405                1410

Phe Pro
1415

```
<210> SEQ ID NO 36
<211> LENGTH: 4134
<212> TYPE: DNA
<213> ORGANISM: Artificial sequence
<220> FEATURE:
<223> OTHER INFORMATION: ALNQ_214_12000

<400> SEQUENCE: 36
atgaagtctg acaacattgc tatggaagac ttgccagact ccaaatactt gaaacaacgt      60
agattattga ccccattgat gtctaagaag gtcccaccaa ttccatctga agacgaaaga     120
aaggcttacg gtgaatacta caccaaccca gtctctcgta tgatgttctg gtggttgaac     180
ccaatcctaa aagtcggtta cagaagaact ttgactgaaa acgacttgtt ctacctagaa     240
gatagacaaa gaactgaaac tttgtacgaa attttcagag ttacctaga cgaagaaatc     300 gctagagctt ggaaaaagtc tcaagaatcc tctgacgacc aagagaatt caagttgcca     360 atttacatta ttccattgtg tttgttcaag accatgaaat gggaatactc cagaggtatc     420
ttgcaaaaga ttttgggtga ctgtgcttct gctaccaccc cattattgca gaaaaagctc     480
```

```
atcaactttg tgcaagttaa gactttctct aacgtcggta acaccggtca aggtgttggt    540
tacgctattg gtgtctgttt gatgatcttc ttccaagttc taatgttgac tcacgctttc    600
cacaacttcc aaatctccgg tgctaaggct aaggctgttt tgaccagatt gttgttggac    660
aagtctttga ctgtcgatgc tagaggtaac cactacttcc cagcctccaa gatccaatct    720
atgatttcca ctgacttgaa cagaattgac ttggctgttg gtttcgctcc agtcggtttt    780
gtcaccattt tcccaatcat tatctgtatt gctttgttga tttggaacgt cggtgtttct    840
gctttggttg gtattggtgt tttcattgct aacattttcg ttttgggttt gttcgtttct    900
tccttgatgt tgtacagaga aaaggccatg gttttcactg acaagagagt taacttggtt    960
aaggaattgt tgaagaactt caaaatgatc aaattctact cctgggaaaa ctcttaccaa   1020
gatcgtatcg aaaacgctag aaacaatgaa atgaagtaca tcttgagatt acaattgttg   1080
agaaacttcg tcttctcttt agctttcgcc atgccagttt tggcttccat ggctaccttc   1140
tgtactgctt tcaagatcac cgatggtaaa tccgctgcct ctgttttctc ctccttatct   1200
ttgttcgaag tcttgtcttt acaattcatc ttggctccat tttccttgaa ctctactgtc   1260
gacatgatgg tcagtgttaa gaagattaac caattcttgc aacacaagga cactaaccca   1320
aacgaatttt ctgtcgaaaa gttttctgac tccactttgg ctatcaaggt cgataatgct   1380
tctttcgaat gggacacctt tgaagatgaa gaaaaggact acgaagaaga agctaagact   1440
aaggacaaca tcgaagatga ggaccataac tgtgccactg aaaccattaa gggtaagatc   1500
actgtcgact acaagtctga ttctgattcc atctcttcta ccttgaccaa gggtgtcaag   1560
accgctttcc caggtttgaa caacattaac ctagaaatcg ccagggtga attcatcgtt   1620 gtcaccggtg ccatcggttc tggtaagtct tctttgttgc aagccatctc tggtttaatg   1680
aagagaactt ctggtgaagt ctacgtcgat ggtgacttgt tgttgtgtgg ttatccatgg   1740
gttcaaaact ccactatcag agaaaacatc ttgttcggtt tgccattcaa caaggaaaga   1800
tacgaccaag ttgtttactc ctgttctttg caatctgatt ttgatcaatt ccaaggtggt   1860
gacatgaccg aagtcggtga agaggtatc actttgtctg gtggtcaaaa agccagaatt   1920
aacttagcta gatctgtcta tgctgacaag gatatcatct tattggatga tgtcttgtct   1980
gctgttgacg ctaaagtcgg taagcacatc gtcaacacct gtattttggg tctattgggt   2040
ggtaagacca gaattatggc tactcaccaa ttgtctttga ttgattccgc tgatagaatg   2100
gttttcttga acggtgacgg taccattgac ttcggtacca tcccagaatt acgtaagaga   2160
aaccaaaagt tgattgaatt gttacaacac caacgtgacc ctggtcaaga taaagaagat   2220
ttgtctaacg acttggacat tcaaggttct actgatgaag gtcaacaaat cgaacacgct   2280
gatgaacata aggaaatcgt taaaattatc ggtgatgagg aaaaggccgt taatgctttg   2340
tctttccaag tttactacaa ctactgtaag ttggctttcg gtaaattggg ttacatttct   2400
atgttggttt tcattatcgt cagctctttg gaaactttca cccaaatctt caccaacact   2460
tggttgtctt tctggatcga agataagttc gtttccagat ctaagaactt ctacatgggt   2520
atctacatca tgtttgcttt cttatacgct atcatgttgt gtttctttt gttcttgttg   2580 ggttacttct gtgttaaggc tgctgaaaga ttaaacatta aggcttctag aaagatcttg   2640
cacgttccaa tgtccttcat ggacattct ccaatcggtc gtgtcttaaa cagattcacc   2700
aaggataccg atgtcttgga caacgaattg ttggaacaat tgatccaatt cttatctcca   2760
ttgttcaact gtttcggtat catcatcttg tgtattgttt acatcccatg gttcgctatc   2820
ggtgttccaa ttatcttggg tttctacttc atcatcgctt cttactacca agcctctgct   2880
```

| | |
|---|---|
| agagaaatca agagattgga agctgtcaag agatcctttg tttcggtca tttccacgaa | 2940 |
| gtccttactg gtaaggatac catcaaggct tacaacgcca ttgacagaat gaagttgaaa | 3000 |
| ctaaacaagt tgatcgacga acaaaacgaa gcttactact tgactattgc taaccaaaga | 3060 |
| tggttgggtg ctaacttggc tatcgtttct ttctctatgg ttttcgttat ttctttctta | 3120 |
| tgtatcttca gagttttcaa catctccgcc gcttccactg gtttgttgtt aacctacgtt | 3180 |
| atcgccttga ctgactctat caccatgatt atgagagcta tgacccaagt cgaaaacgaa | 3240 |
| ttcaactccg tcgaacgtgt caaccactac gcttttgact tgatccaaga agccccatac | 3300 |
| gaaatcccag aaaacgaccc agctgaagac tggccacaac acggtaagat cgaattcaag | 3360 |
| gacgtttcca tgagatacag acctgaattg ccattcgttt tgaagaacat taacttgtcc | 3420 |
| gtcagagaac aagagaaaat tggtttctgt ggtagaactg gtgccggtaa gtccactttc | 3480 |
| atgacctgtt tgtacagaat cactgaatac gaaggtttga tctccatcga cggtgtcgat | 3540 |
| atctctagat tgggtttgca cagattgaga tccaagttga ccattattcc tcaagaccca | 3600 |
| gttctattcg ttggtaccat tagagaaaac ttggacccat tcaccgaaca ctccgatgac | 3660 |
| gaattgtggg aagctttggc catttccggt ttgatcgaac gtgaagactt ggaagtcgtc | 3720 |
| aagggtcaag aaaagattgg tggtaacgat tccggtaagt tgcacaagtt ccacttggtt | 3780 |
| cgtatggttg aagacgatgg tatcaacttc tctttgggtg agacaatt gattgctttg | 3840 |
| gctagagcct tggttagaaa gtccaagatc ttaatcttgg acgaagctac ttcttccgtc | 3900 |
| gactacgcta ctgattccaa gattcaaaga accattgcct ccgaattcag agactgtact | 3960 |
| attttgtgta tcgcccatag attgaacacc atcttaggtt acgacaagat cgtcgttatg | 4020 |
| gacaacggtg aaatcgttga atttgaaaac ccaaagttgt tgttcatgcg tgaaaactcc | 4080 |
| gtttcagat ccatgtgtga acaagctaac attaccatca tgactttga ataa | 4134 |

<210> SEQ ID NO 37
<211> LENGTH: 4134
<212> TYPE: DNA
<213> ORGANISM: Issatchenkia orientalis

<400> SEQUENCE: 37

| | |
|---|---|
| atgaagtcag ataacattgc aatggaggac ctacccgact ccaaatactt gaaacagaga | 60 |
| cgattattaa ctccgttgat gtcaaaaaaa gttccaccta ttccaagtga agatgagagg | 120 |
| aaggcatacg gggaatatta tacgaatccg gtatcacgga tgatgttttg gtggttaaat | 180 |
| cccattttga aggtgggata taggcgaaca ttgacggaga atgatctttt ctaccttgaa | 240 |
| gacagacaac gtacagagac attatatgaa atatttcgtg gttacttgga tgaggaaatt | 300 |
| gcacgtgcat ggaaaaaatc tcaagaaagc tcagatgatc caagagagtt caagcttccg | 360 |
| atctatatta tcccttatg tttatttaag acaatgaaat gggaatacag ccggggaatt | 420 |
| ctccagaaaa tcttgggtga ttgtgcttct gcaacgaccc cactattaca gaaaaaacta | 480 |
| atcaactttg tccaggtcaa gactttcagt aatgtcggaa atactggtca gggtgtagga | 540 |
| tatgctattg gcgtttgctt gatgattttc tttcaagttt taatgttaac tcatgcattt | 600 |
| cacaatttcc aaatttcggg tgcaaaggca aagctgttt tgcaacaagatt gctcttggat | 660 |
| aaatcgttga ctgttgatgc cagaggcaac cattatttc cagcgagtaa gattcaaagc | 720 |
| atgatttcta ctgatttgaa tagaatagac cttgctgtcg gatttgcacc agtgggggttt | 780 |
| gttactatat tccctattat tatctgcatt gccttattga tttggaatgt tggagtctcg | 840 |

-continued

```
gcattggttg gtattggggt attcattgca aacattttg tgttgggact ttttgtatca      900
agtctaatgt tatacaggga gaaggcgatg gtattcaccg acaaaagagt caatttggtt      960
aaggaactat tgaaaatttt taaaatgatt aagttctaca gttgggaaaa ctcttatcag     1020
gatagaattg aaaatgcaag gaacaacgaa atgaaatata ttttgaggtt acaattgcta     1080
agaaattttg tgttttcgtt agcttttgcg atgcctgttt tggcatcaat ggctacattt     1140
tgtacagcct ttaagataac tgacggcaaa agtgccgcat ctgtgttttc atctctctca     1200
ttgtttgaag ttttatcgct acaatttatt ttggccccct tctcactaaa ttctactgtg     1260
gatatgatgg tttcagttaa aaagataaac cagtttctgc agcataaaga taccaatcca     1320
aatgagttca gcgttgaaaa gttcagtgat agtacattgg caatcaaggt cgataatgca     1380
tcatttgaat gggatacgtt tgaggatgaa gagaaagatt atgaagagga agctaaaact     1440
aaagacaaca ttgaagatga agatcataat tgtgctacgg aaacaatcaa gggaaaaata     1500
acagtggact ataagagcga cagtgactca atttctagta ctttaacgaa aggggttaaa     1560
actgcatttc ctggactaaa taatatcaat cttgaaattg caaaagggga attcattgtt     1620
gttactggtg caattggttc cggcaaatcc tctctacttc aggccatttc tgggctaatg     1680
aagagaacat caggggaagt gtatgttgat ggtgatttgt tgttatgtgg ttacccgtgg     1740
gtacaaaact caacaatacg agagaatata ctatttggat taccatttaa taaggagagg     1800
tatgaccaag tcgtgtattc atgctcgttg cagagtgatt ttgatcaatt tcaaggaggt     1860
gatatgacgg aagttggcga gagagggata accttatcag gaggccaaaa ggccagaatt     1920
aatttagctc ggagtgttta tgctgataag gatattattt tattagacga cgttctcagt     1980
gcggtcgacg ctaaagttgg caagcatatt gtgaatacat gcatcttagg attattggga     2040
ggtaaaacaa gaatcatggc tacccaccaa ctaagtttga tcgactctgc tgatcgtatg     2100
gtttttctca atggagatgg aactattgat tttggtacta ttcctgagct aagaaagaga     2160
aaccagaagc tgattgagtt actacaacat caaagggatc caggtcaaga taaagaggat     2220
ctctcaaatg atttggatat tcaaggaagc acagatgagg gtcagcaaat tgagcatgca     2280
gacgagcata aagagatagt caagattatt ggtgacgagg aaaaagcagt taatgcattg     2340
agtttccagg tttattataa ctattgtaag cttgcatttg gtaagcttgg atatatttcg     2400
atgttggtat tcattattgt ttctagtttg gagaccttca cccaaatatt caccaatact     2460
tggttgtcat tttggatcga ggataaattt gttagtagat ccaaaaattt ctatatggga     2520
atatacatca tgtttgcatt tttgtatgca ataatgctat gttttttttct cttttttactg     2580 ggatatttt gtgtaaaggc agcagagaga ctaaatatta aagcatccag gaagattcta     2640
catgttccaa tgtctttat ggacatatca cctattggta gagtcttgaa tcggtttact     2700
aaagatacag atgtattaga caatgaattg ttagagcaat taattcaatt tttaagccca     2760
ctattcaact gttttggtat tatcatattg tgcattgttt ataccatg gtttgctatt     2820 ggtgtcccta taattcttgg atttattttt ataatagcca gttattatca ggccagtgca     2880
agagaaatca agagattaga ggctgtaaag aggtcgtttg ttttggccca ttttcacgaa     2940
gttctaacag ggaaagacac catcaaagca tataatgcta ttgatcggat gaaattgaag     3000
ctgaacaaat tgattgatga acagaatgaa gcttattatc taacaatcgc caatcagaga     3060
tggttaggag caaatttggc gattgtctca ttttcaatgg tttttgttat ttcgtttctg     3120
tgtatcttta gggttttcaa cataagtgca gcatccactg gtttgctttt gacctacgtc     3180
atagcactga cagattctat taccatgatt atgagagcaa tgactcaagt tgagaatgag     3240
```

-continued

```
ttcaactctg tggaacgggt caaccattat gcatttgatc ttatacaaga agcaccatat    3300
gaaataccgg agaatgatcc cgctgaggat tggccacaac atggcaaaat tgaattcaaa    3360
gatgtgagta tgagatatag accggaacta ccatttgttt tgaaaaatat caatttgagt    3420
gttagagaac aagaaaagat tggattttgt ggtagaacag gtgcaggtaa gtctacattt    3480
atgacatgtc tatataggat aacagaatac gaaggcctta tatcaatcga tggtgttgat    3540
attagccgat tagggttgca tagactacga tctaaattga ccattatacc gcaagacccg    3600
gtattatttg ttggtaccat tagggagaac ctcgatccat ttacagagca ttctgatgat    3660
gaattatggg aagcgcttgc gatatctgga ttgattgagc gggaagatct agaagtcgtc    3720
aagggacaag agaagatagg tgggaatgat agtgggaagt tacacaagtt ccacctagtt    3780
cgaatggttg aggatgatgg catcaatttt tcacttggtg agaggcagtt gattgcctta    3840
gccagggcat tagttaggaa aagcaagata ttgatattgg atgaggctac atcgagtgtt    3900
gactatgcta cagactctaa aatccagcga acgattgcta gtgagtttag ggattgtact    3960
atattatgta ttgctcatcg attgaacacc attttaggtt atgataaaat tgtcgttatg    4020
gacaatggtg agattgttga atttgagaat cccaaattgt tgtttatgag ggagaatagt    4080
gtatttcgat ccatgtgtga gcaggcaaac atcaccatca atgatttga ataa            4134
```

<210> SEQ ID NO 38
<211> LENGTH: 1377
<212> TYPE: PRT
<213> ORGANISM: Issatchenkia orientalis

<400> SEQUENCE: 38

```
Met Lys Ser Asp Asn Ile Ala Met Glu Asp Leu Pro Asp Ser Lys Tyr
1               5                   10                  15

Leu Lys Gln Arg Arg Leu Leu Thr Pro Leu Met Ser Lys Lys Val Pro
            20                  25                  30

Pro Ile Pro Ser Glu Asp Glu Arg Lys Ala Tyr Gly Glu Tyr Tyr Thr
        35                  40                  45

Asn Pro Val Ser Arg Met Met Phe Trp Trp Leu Asn Pro Ile Leu Lys
    50                  55                  60

Val Gly Tyr Arg Arg Thr Leu Thr Glu Asn Asp Leu Phe Tyr Leu Glu
65                  70                  75                  80

Asp Arg Gln Arg Thr Glu Thr Leu Tyr Glu Ile Phe Arg Gly Tyr Leu
                85                  90                  95

Asp Glu Glu Ile Ala Arg Ala Trp Lys Lys Ser Gln Glu Ser Ser Asp
            100                 105                 110

Asp Pro Arg Glu Phe Lys Leu Pro Ile Tyr Ile Ile Pro Leu Cys Leu
        115                 120                 125

Phe Lys Thr Met Lys Trp Glu Tyr Ser Arg Gly Ile Leu Gln Lys Ile
    130                 135                 140

Leu Gly Asp Cys Ala Ser Ala Thr Thr Pro Leu Leu Gln Lys Lys Leu
145                 150                 155                 160

Ile Asn Phe Val Gln Val Lys Thr Phe Ser Asn Val Gly Asn Thr Gly
                165                 170                 175

Gln Gly Val Gly Tyr Ala Ile Gly Val Cys Leu Met Ile Phe Phe Gln
            180                 185                 190

Val Leu Met Leu Thr His Ala Phe His Asn Phe Gln Ile Ser Gly Ala
        195                 200                 205

Lys Ala Lys Ala Val Leu Thr Arg Leu Leu Leu Asp Lys Ser Leu Thr
```

```
              210                 215                 220
Val Asp Ala Arg Gly Asn His Tyr Phe Pro Ala Ser Lys Ile Gln Ser
225                 230                 235                 240

Met Ile Ser Thr Asp Leu Asn Arg Ile Asp Leu Ala Val Gly Phe Ala
                    245                 250                 255

Pro Val Gly Phe Val Thr Ile Phe Pro Ile Ile Ile Cys Ile Ala Leu
                260                 265                 270

Leu Ile Trp Asn Val Gly Val Ser Ala Leu Val Gly Ile Gly Val Phe
            275                 280                 285

Ile Ala Asn Ile Phe Val Leu Gly Leu Phe Val Ser Ser Leu Met Leu
        290                 295                 300

Tyr Arg Glu Lys Ala Met Val Phe Thr Asp Lys Arg Val Asn Leu Val
305                 310                 315                 320

Lys Glu Leu Leu Lys Asn Phe Lys Met Ile Lys Phe Tyr Ser Trp Glu
                    325                 330                 335

Asn Ser Tyr Gln Asp Arg Ile Glu Asn Ala Arg Asn Asn Glu Met Lys
                340                 345                 350

Tyr Ile Leu Arg Leu Gln Leu Leu Arg Asn Phe Val Phe Ser Leu Ala
            355                 360                 365

Phe Ala Met Pro Val Leu Ala Ser Met Ala Thr Phe Cys Thr Ala Phe
        370                 375                 380

Lys Ile Thr Asp Gly Lys Ser Ala Ala Ser Val Phe Ser Ser Leu Ser
385                 390                 395                 400

Leu Phe Glu Val Leu Ser Leu Gln Phe Ile Leu Ala Pro Phe Ser Leu
                    405                 410                 415

Asn Ser Thr Val Asp Met Met Val Ser Val Lys Lys Ile Asn Gln Phe
                420                 425                 430

Leu Gln His Lys Asp Thr Asn Pro Asn Glu Phe Ser Val Glu Lys Phe
            435                 440                 445

Ser Asp Ser Thr Leu Ala Ile Lys Val Asp Asn Ala Ser Phe Glu Trp
        450                 455                 460

Asp Thr Phe Glu Asp Glu Lys Asp Tyr Glu Glu Ala Lys Thr
465                 470                 475                 480

Lys Asp Asn Ile Glu Asp Asp His Asn Cys Ala Thr Glu Thr Ile
                    485                 490                 495

Lys Gly Lys Ile Thr Val Asp Tyr Lys Ser Asp Ser Asp Ser Ile Ser
                500                 505                 510

Ser Thr Leu Thr Lys Gly Val Lys Thr Ala Phe Pro Gly Leu Asn Asn
            515                 520                 525

Ile Asn Leu Glu Ile Ala Lys Gly Glu Phe Ile Val Val Thr Gly Ala
        530                 535                 540

Ile Gly Ser Gly Lys Ser Ser Leu Leu Gln Ala Ile Ser Gly Leu Met
545                 550                 555                 560

Lys Arg Thr Ser Gly Glu Val Tyr Val Asp Gly Asp Leu Leu Leu Cys
                    565                 570                 575

Gly Tyr Pro Trp Val Gln Asn Ser Thr Ile Arg Glu Asn Ile Leu Phe
                580                 585                 590

Gly Leu Pro Phe Asn Lys Glu Arg Tyr Asp Gln Val Val Tyr Ser Cys
            595                 600                 605

Ser Leu Gln Ser Asp Phe Asp Gln Phe Gln Gly Gly Asp Met Thr Glu
        610                 615                 620

Val Gly Glu Arg Gly Ile Thr Leu Ser Gly Gly Gln Lys Ala Arg Ile
625                 630                 635                 640
```

```
Asn Leu Ala Arg Ser Val Tyr Ala Asp Lys Asp Ile Ile Leu Leu Asp
                645                 650                 655

Asp Val Leu Ser Ala Val Asp Ala Lys Val Gly Lys His Ile Val Asn
            660                 665                 670

Thr Cys Ile Leu Gly Leu Leu Gly Gly Lys Thr Arg Ile Met Ala Thr
        675                 680                 685

His Gln Leu Ser Leu Ile Asp Ser Ala Asp Arg Met Val Phe Leu Asn
    690                 695                 700

Gly Asp Gly Thr Ile Asp Phe Gly Thr Ile Pro Glu Leu Arg Lys Arg
705                 710                 715                 720

Asn Gln Lys Leu Ile Glu Leu Leu Gln His Gln Arg Asp Pro Gly Gln
                725                 730                 735

Asp Lys Glu Asp Leu Ser Asn Asp Leu Asp Ile Gln Gly Ser Thr Asp
            740                 745                 750

Glu Gly Gln Gln Ile Glu His Ala Asp Glu His Lys Glu Ile Val Lys
        755                 760                 765

Ile Ile Gly Asp Glu Glu Lys Ala Val Asn Ala Leu Ser Phe Gln Val
    770                 775                 780

Tyr Tyr Asn Tyr Cys Lys Leu Ala Phe Gly Lys Leu Gly Tyr Ile Ser
785                 790                 795                 800

Met Leu Val Phe Ile Ile Val Ser Ser Leu Glu Thr Phe Thr Gln Ile
                805                 810                 815

Phe Thr Asn Thr Trp Leu Ser Phe Trp Ile Glu Asp Lys Phe Val Ser
            820                 825                 830

Arg Ser Lys Asn Phe Tyr Met Gly Ile Tyr Ile Met Phe Ala Phe Leu
        835                 840                 845

Tyr Ala Ile Met Leu Cys Phe Phe Leu Phe Leu Leu Gly Tyr Phe Cys
    850                 855                 860

Val Lys Ala Ala Glu Arg Leu Asn Ile Lys Ala Ser Arg Lys Ile Leu
865                 870                 875                 880

His Val Pro Met Ser Phe Met Asp Ile Ser Pro Ile Gly Arg Val Leu
                885                 890                 895

Asn Arg Phe Thr Lys Asp Thr Asp Val Leu Asp Asn Glu Leu Leu Glu
            900                 905                 910

Gln Leu Ile Gln Phe Leu Ser Pro Leu Phe Asn Cys Phe Gly Ile Ile
        915                 920                 925

Ile Leu Cys Ile Val Tyr Ile Pro Trp Phe Ala Ile Gly Val Pro Ile
    930                 935                 940

Ile Leu Gly Phe Tyr Phe Ile Ala Ser Tyr Tyr Gln Ala Ser Ala
945                 950                 955                 960

Arg Glu Ile Lys Arg Leu Glu Ala Val Lys Arg Ser Phe Val Phe Gly
                965                 970                 975

His Phe His Glu Val Leu Thr Gly Lys Asp Thr Ile Lys Ala Tyr Asn
            980                 985                 990

Ala Ile Asp Arg Met Lys Leu Lys Leu Asn Lys Leu Ile Asp Glu Gln
        995                 1000                1005

Asn Glu Ala Tyr Tyr Leu Thr Ile Ala Asn Gln Arg Trp Leu Gly
        1010                1015                1020

Ala Asn Leu Ala Ile Val Ser Phe Ser Met Val Phe Val Ile Ser
        1025                1030                1035

Phe Leu Cys Ile Phe Arg Val Phe Asn Ile Ser Ala Ala Ser Thr
        1040                1045                1050
```

-continued

| | | | | | | | | | | | |
|---|---|---|---|---|---|---|---|---|---|---|---|
| Gly | Leu | Leu | Leu | Thr | Tyr | Val | Ile | Ala | Leu | Thr | Asp | Ser | Ile | Thr |
| | 1055 | | | | 1060 | | | | 1065 | | |
| Met | Ile | Met | Arg | Ala | Met | Thr | Gln | Val | Glu | Asn | Glu | Phe | Asn | Ser |
| 1070 | | | | | 1075 | | | | | 1080 | | |
| Val | Glu | Arg | Val | Asn | His | Tyr | Ala | Phe | Asp | Leu | Ile | Gln | Glu | Ala |
| 1085 | | | | | 1090 | | | | 1095 | | |
| Pro | Tyr | Glu | Ile | Pro | Glu | Asn | Asp | Pro | Ala | Glu | Asp | Trp | Pro | Gln |
| 1100 | | | | | 1105 | | | | | 1110 | | |
| His | Gly | Lys | Ile | Glu | Phe | Lys | Asp | Val | Ser | Met | Arg | Tyr | Arg | Pro |
| 1115 | | | | | 1120 | | | | 1125 | | |
| Glu | Leu | Pro | Phe | Val | Leu | Lys | Asn | Ile | Asn | Leu | Ser | Val | Arg | Glu |
| 1130 | | | | | 1135 | | | | | 1140 | | |
| Gln | Glu | Lys | Ile | Gly | Phe | Cys | Gly | Arg | Thr | Gly | Ala | Gly | Lys | Ser |
| 1145 | | | | | 1150 | | | | 1155 | | |
| Thr | Phe | Met | Thr | Cys | Leu | Tyr | Arg | Ile | Thr | Glu | Tyr | Glu | Gly | Leu |
| 1160 | | | | | 1165 | | | | | 1170 | | |
| Ile | Ser | Ile | Asp | Gly | Val | Asp | Ile | Ser | Arg | Leu | Gly | Leu | His | Arg |
| 1175 | | | | | 1180 | | | | 1185 | | |
| Leu | Arg | Ser | Lys | Leu | Thr | Ile | Ile | Pro | Gln | Asp | Pro | Val | Leu | Phe |
| 1190 | | | | | 1195 | | | | | 1200 | | |
| Val | Gly | Thr | Ile | Arg | Glu | Asn | Leu | Asp | Pro | Phe | Thr | Glu | His | Ser |
| 1205 | | | | | 1210 | | | | 1215 | | |
| Asp | Asp | Glu | Leu | Trp | Glu | Ala | Leu | Ala | Ile | Ser | Gly | Leu | Ile | Glu |
| 1220 | | | | | 1225 | | | | | 1230 | | |
| Arg | Glu | Asp | Leu | Glu | Val | Val | Lys | Gly | Gln | Glu | Lys | Ile | Gly | Gly |
| 1235 | | | | | 1240 | | | | 1245 | | |
| Asn | Asp | Ser | Gly | Lys | Leu | His | Lys | Phe | His | Leu | Val | Arg | Met | Val |
| 1250 | | | | | 1255 | | | | | 1260 | | |
| Glu | Asp | Asp | Gly | Ile | Asn | Phe | Ser | Leu | Gly | Glu | Arg | Gln | Leu | Ile |
| 1265 | | | | | 1270 | | | | 1275 | | |
| Ala | Leu | Ala | Arg | Ala | Leu | Val | Arg | Lys | Ser | Lys | Ile | Leu | Ile | Leu |
| 1280 | | | | | 1285 | | | | | 1290 | | |
| Asp | Glu | Ala | Thr | Ser | Ser | Val | Asp | Tyr | Ala | Thr | Asp | Ser | Lys | Ile |
| 1295 | | | | | 1300 | | | | 1305 | | |
| Gln | Arg | Thr | Ile | Ala | Ser | Glu | Phe | Arg | Asp | Cys | Thr | Ile | Leu | Cys |
| 1310 | | | | | 1315 | | | | | 1320 | | |
| Ile | Ala | His | Arg | Leu | Asn | Thr | Ile | Leu | Gly | Tyr | Asp | Lys | Ile | Val |
| 1325 | | | | | 1330 | | | | 1335 | | |
| Val | Met | Asp | Asn | Gly | Glu | Ile | Val | Glu | Phe | Glu | Asn | Pro | Lys | Leu |
| 1340 | | | | | 1345 | | | | | 1350 | | |
| Leu | Phe | Met | Arg | Glu | Asn | Ser | Val | Phe | Arg | Ser | Met | Cys | Glu | Gln |
| 1355 | | | | | 1360 | | | | 1365 | | |
| Ala | Asn | Ile | Thr | Ile | Asn | Asp | Phe | Glu |
| 1370 | | | | | 1375 | | |

STEVIOL GLYCOSIDE TRANSPORT

CROSS-REFERENCE TO RELATED APPLICATIONS

This application is a divisional of U.S. Ser. No. 15/751,526, filed 9 Feb. 2018, which is a National Stage entry of International Application No. PCT/EP2016/069357, filed 15 Aug. 2016, and claims benefit to U.S. Provisional Application No. 62/204,704, filed 13 Aug. 2015. The disclosure of the priority applications are incorporated in their entirety herein by reference.

REFERENCE TO SEQUENCE LISTING SUBMITTED AS A COMPLIANT ASCII TEXT FILE (.TXT)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2919208-345002_ST25.txt" created on 9 Apr. 2020, and 90,605 bytes in size) is submitted concurrently with the instant application, and the entire contents of the Sequence Listing are incorporated herein by reference.

BACKGROUND

Field of the Invention

The present invention relates to a recombinant host capable of producing a steviol glycoside. The invention also relates to a process for the preparation of a steviol glycoside using such a recombinant host. The invention also relates to a fermentation broth comprising a steviol glycoside, a steviol glycoside and to a composition comprising two or more steviol glycosides. The invention further relates to a foodstuff, feed or beverage which comprises a steviol glycoside or a composition comprising two or more steviol glycosides.

Description of Related Art

The leaves of the perennial herb, *Stevia rebaudiana* Bert., accumulate quantities of intensely sweet compounds known as steviol glycosides. Whilst the biological function of these compounds is unclear, they have commercial significance as alternative high potency sweeteners.

These sweet steviol glycosides have functional and sensory properties that appear to be superior to those of many high potency sweeteners. In addition, studies suggest that stevioside can reduce blood glucose levels in Type II diabetics and can reduce blood pressure in mildly hypertensive patients.

Steviol glycosides accumulate in Stevia leaves where they may comprise from 10 to 20% of the leaf dry weight. Stevioside and rebaudioside A are both heat and pH stable and suitable for use in carbonated beverages and many other foods. Stevioside is between 110 and 270 times sweeter than sucrose, rebaudioside A between 150 and 320 times sweeter than sucrose. In addition, rebaudioside D is also a high-potency diterpene glycoside sweetener which accumulates in Stevia leaves. It may be about 200 times sweeter than sucrose. Rebaudioside M is a further high-potency diterpene glycoside sweetener. It is present in trace amounts in certain stevia variety leaves, but has been suggested to have a superior taste profile.

Steviol glycosides have traditionally been extracted from the *Stevia* plant. In *Stevia*, (−)-kaurenoic acid, an intermediate in gibberellic acid (GA) biosynthesis, is converted into the tetracyclic diterpene steviol, which then proceeds through a multi-step glycosylation pathway to form the various steviol glycosides. However, yields may be variable and affected by agriculture and environmental conditions. Also, Stevia cultivation requires substantial land area, a long time prior to harvest, intensive labour and additional costs for the extraction and purification of the glycosides.

More recently, interest has grown in producing steviol glycosides using fermentative processes. WO2013/110673 and WO2015/007748 describe microorganisms that may be used to produce at least the steviol glycosides rebaudioside A, rebaudioside D and rebaudioside M.

Further improvement of such microorganisms is desirable in order that higher amounts of steviol glycosides may be produced and/or additional or new steviol glycosides and/or higher amounts of specific steviol glycosides and/or mixtures of steviol glycosides having desired ratios of different steviol glycosides.

SUMMARY OF THE INVENTION

The present invention is based on the identification of proteins which are capable of mediating steviol glycoside transport.

Accordingly, one or more such proteins may be overexpressed in a recombinant host (such as a microbial cell) in order to increase steviol glycoside transport out of the host. Alternatively, a host (such as a microbial cell) may be modified so as to express less of one or more such proteins than a corresponding non-modified version of the host. In this case, more steviol glycoside may be retained within the host which is then glycosylated to a steviol glycoside comprising a higher number of sugar moieties.

Thus, the invention relates to a recombinant host, for example a cell such as a microbial cell, which produces steviol glycoside outside the host to a greater degree than a corresponding host not overexpressing the protein. This may facilitate easier recovery of steviol glycosides. The invention also relates to a recombinant host capable of producing a steviol glycoside which overexpresses a heterologous polypeptide which mediates steviol glycoside transport.

Accordingly, the invention relates to a recombinant host capable of producing a steviol glycoside which overexpresses a polypeptide which mediates steviol glycoside transport and which polypeptide comprises the amino acid sequence set forth in SEQ ID NO: 35 or SEQ ID NO: 38 or an amino acid sequence having at least about 50% sequence identity to either thereto.

The invention also relates to a recombinant host capable of producing a steviol glycoside which has been modified, preferably in its genome, to result in a deficiency in the production of a polypeptide which mediates steviol glycoside transport and which polypeptide comprises the amino acid sequence set forth in SEQ ID NO: 35 of SEQ ID NO: 38 or an amino acid sequence having at least about 50% sequence identity to either thereto.

The invention also relates to a recombinant host which comprises steviol glycosides (inside and/or outside the host) having a higher or lower average glycosylation number than a corresponding host not modified according to the invention.

The invention also relates to:
a process for the preparation of a steviol glycoside which comprises fermenting a recombinant host according to any one of the preceding claims in a suitable fermentation medium and, optionally, recovering the steviol glycoside;

a fermentation broth comprising a steviol glycoside obtainable by a process of the invention;

a steviol glycoside obtained by a process or a fermentation broth of the invention;

a composition comprising two or more steviol glycosides of the invention or obtainable by a process of the invention;

a foodstuff, feed or beverage which comprises a steviol glycoside or a composition of the invention.

DESCRIPTION OF THE SEQUENCE LISTING

Figure 1:
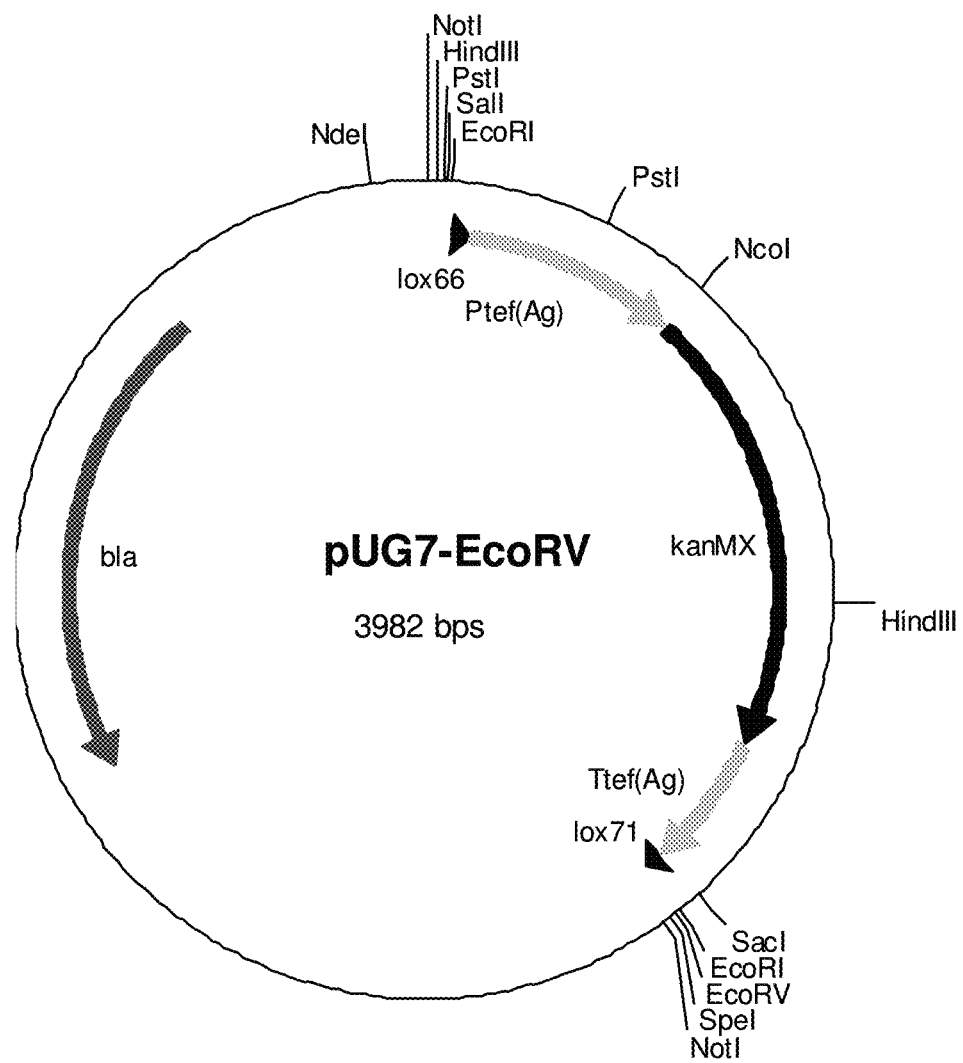
FIG. 1 sets out a schematic representation of the plasmid pUG7-KanMX.

A description of the sequences is set out in Table 15. Sequences described herein may be defined with reference to the sequence listing or with reference to the database accession numbers also set out in Table 15.

DETAILED DESCRIPTION OF THE INVENTION

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The invention relates to the identification of polypeptides which are capable of mediating steviol glycoside transport. Such a polypeptide may directly mediate steviol glycoside transport, i.e. may be a transporter protein, or may indirectly mediate steviol glycoside transport. Such a polypeptide may be capable of mediating transport of one or more steviol glycoside.

The invention relates to a recombinant host either overexpressing or having reduced expression of such a polypeptide. The terms recombinant host or recombinant cell may, depending on the context, be used interchangeably.

Such a polypeptide as described herein may be overexpressed in a recombinant host, such as a recombinant host cell, capable of producing one or more steviol glycosides. Such a cell may be capable of producing more of one or more steviol glycosides external to the cell than a corresponding cell which does not overexpress the polypeptide. That is to say, a recombinant cell according to the invention may have increased or decreased steviol glycoside transport in a comparison with a corresponding non-recombinant cell.

Accordingly, the invention provides a recombinant host capable of producing a steviol glycoside which overexpresses a polypeptide, the polypeptide being one which is capable of mediating steviol glycoside transport and which polypeptide comprises the amino acid sequence set forth in SEQ ID NO: 35 or SEQ ID NO: 38 or an amino acid sequence having at least about 50% sequence identity to either thereto.

The expression of such a polypeptide may also be modified in a host, such as a recombinant host cell, such that it is reduced compared to a corresponding cell which has not been similarly modified. In this way, the amount of one or more steviol glycosides outside the cell may be reduced in comparison with a corresponding cell which has not been similarly modified. This may allow for increased glycosylation of one or more steviol glycosides within the cell compared with a corresponding cell which has not been similarly modified. Such a host may thus comprise steviol glycosides having a higher average glycosylation number compared with a corresponding cell which has not been similarly modified.

Accordingly, the invention provides a recombinant host capable of producing a steviol glycoside which has been modified, preferably in its genome, to result in a deficiency in the production of a polypeptide, the polypeptide being one which is capable of mediating steviol glycoside transport and which polypeptide comprises the amino acid sequence set forth in SEQ ID NO: 35 or SEQ ID NO: 38 or an amino acid sequence having at least about 50% sequence identity to either thereto.

A host cell of the invention is a recombinant host cell. "Recombinant" in this sense means that the host cell is a non-naturally occurring host cell, for example modified by introduction of one or more nucleic acids using recombinant techniques. A nucleic acid used to modify a host cell to arrive at a recombinant host cell of the invention may be a naturally-occurring nucleic acid or a non-naturally occurring nucleic acid.

Thus, when used in reference to a host of the invention, "recombinant" indicates that a cell has been modified by the introduction of one or more heterologous nucleic acid or protein or the alteration of a native nucleic acid or protein, or that the cell is derived from a cell so modified. The term "heterologous" as used herein refers to nucleic acid or amino acid sequences not naturally occurring in a host cell. In other words, the nucleic acid or amino acid sequence is not identical to that naturally found in the host cell.

The invention relates to a recombinant host capable of producing a steviol glycoside which overexpresses a heterologous polypeptide which mediates steviol glycoside transport. Such a heterologous polypeptide may be obtained from or derived from a genus or species other than that of the host. Accordingly, if the recombinant host is a yeast, the heterologous polypeptide which mediates steviol glycoside transport may be obtained from or derived from a different genus or species of yeast.

For example, if the host cell is a *Saccharomyces* (e.g., *S. cerevisiae, S. bayanus, S. pastorianus, S. carlsbergensis*), the heterologous polypeptide which mediates steviol glycoside transport may be obtained from or derived from a *Candida* (e.g., *C. krusei, C. revkaufi, C. pulcherrima, C. tropicalis, C. utilis*), an *Issatchenkia* (eg. *I. orientalis*) or a *Yarrowia* (e.g., *Y. lipolytica* (formerly classified as *Candida lipolytica*)).

For example, if the host cell is a *Candida* (e.g., *C. krusei, C. revkaufi, C. pulcherrima, C. tropicalis, C. utilis*), the heterologous polypeptide which mediates steviol glycoside transport may be obtained from or derived from a *Saccharomyces* (e.g., *S. cerevisiae, S. bayanus, S. pastorianus, S. carlsbergensis*), an *Issatchenkia* (eg. *I. orientalis*) or a *Yarrowia* (e.g., *Y. lipolytica* (formerly classified as *Candida lipolytica*)).

For example, if the host cell is an *Issatchenkia* (eg. *I. orientalis*), the heterologous polypeptide which mediates steviol glycoside transport may be obtained or derived from a *Saccharomyces* (e.g., *S. cerevisiae, S. bayanus, S. pastorianus, S. carlsbergensis*), a *Candida* (e.g., *C. krusei, C. revkaufi, C. pulcherrima, C. tropicalis, C. utilis*) or a *Yarrowia* (e.g., *Y. lipolytica* (formerly classified as *Candida lipolytica*)).

For example, if the host cell is a *Yarrowia* (e.g., *Y. lipolytica* (formerly classified as *Candida lipolytica*)), the heterologous polypeptide which mediates steviol glycoside transport may be obtained from or derived from a *Saccharomyces* (e.g., *S. cerevisiae, S. bayanus, S. pastorianus, S. carlsbergensis*). a *Candida* (e.g., *C. krusei, C. revkaufi, C. pulcherrima, C. tropicalis, C. utilis*) or an *Issatchenkia* (eg. *I. orientalis*).

If the host cell is *Saccharomyces cerevisiae*, the heterologous polypeptide which mediates steviol glycoside transport may be obtained from or derived from *Yarrowia lipolytica* (formerly classified as *Candida lipolytica*)), *Candida krusei* or *Issatchenkia orientalis*.

If the host cell is *Yarrowia lipolytica*, the heterologous polypeptide which mediates steviol glycoside transport may be obtained from or derived from *Saccharomyces cerevisiae, Yarrowia lipolytica* (formerly classified as *Candida lipolytica*)) or *Candida krusei* or *Issatchenkia orientalis*.

If the host cell is *Candida krusei* or *Issatchenkia orientalis*, the heterologous polypeptide which mediates steviol glycoside transport may be obtained from or derived from *Saccharomyces cerevisiae* or *Yarrowia lipolytica*.

The term "derived from" also includes the terms "originated from," "obtained from," "obtainable from," "isolated from," and "created from," and generally indicates that one specified material find its origin in another specified material or has features that can be described with reference to the another specified material. As used herein, a substance (e.g., a nucleic acid molecule or polypeptide) "derived from" a microorganism may indicate that the substance is native to that microorganism or is a substance native to that microorganism, but may also indicate a substance that has been altered from a native version.

Thus, for example, a recombinant cell may express a polypeptide as defined herein not found within the native (non-recombinant) form of the cell. Alternatively, a recombinant cell may be modified so as to express a native gene encoding a polypeptide as defined herein to a greater degree than takes place within the native "non-recombinant" form of the cell.

Alternatively, a recombinant cell may be modified so as to express a native gene encoding a polypeptide as defined herein to a lesser degree than takes place within the native "non-recombinant" form of the cell.

In a cell of the invention, a polypeptide as defined herein may be overexpressed. Herein, "overexpressed", "overexpression" or the like implies that the recombinant host cell expresses more of the polypeptide than a corresponding cell which does not overexpress the polypeptide or, alternatively, that the polypeptide is expressed in a cell which would not typically express that protein. Alternatively, overexpression may be achieved by expressing a variant polypeptide having a higher specific activity.

A recombinant cell of the invention cell may be modified, preferably in its genome, to result in a deficiency in the production of a polypeptide as defined herein.

Such a cell may be from a parent host cell and be modified, preferably in its genome, if compared to the parent host cell to obtain a different genotype and/or a different phenotype if compared to the parent host cell from which it is derived.

Such a cell which has been modified, preferably in its genome, to result in a deficiency in the production of a polypeptide as defined herein, is a mutant host cell which has been modified, preferably in its genome, to result in a phenotypic feature wherein the cell: a) produces less of the product or produces substantially no product and/or b) produces a product having a decreased activity or decreased specific activity or a product having no activity or no specific activity and combinations of one or more of these possibilities as compared to the parent microbial host cell that has not been modified, when analyzed under the same conditions.

Such a recombinant host may be a full or partial knockout of a nucleic acid sequence encoding a polypeptide as described herein.

The term "recombinant" is synonymous with "genetically modified".

The invention thus concerns recombinant hosts overexpressing or deficient in a polypeptide identified as having steviol glycoside transport mediating activity: typically, the host is one which may be used for the production of steviol glycosides. The ability of a given recombinant host to produce a steviol glycoside may be a property of the host in non-recombinant form or may be a result of the introduction of one or more recombinant nucleic acid sequences (i.e. encoding enzymes leading to the production of a steviol glycoside).

For the purpose of this invention, a polypeptide having steviol glycoside transport mediating activity (i.e. a polypeptide which mediates steviol glycoside transport) is one which has an effect on transport of one or more steviol glycosides across a cell membrane. The effect may be direct, i.e. the polypeptide may be a transporter protein or comprise a functional transporter region. Alternatively, the effect may be indirect, i.e. the polypeptide is not a transporter protein, but its activity nevertheless has an effect on steviol glycoside transport.

Typically, the effect will be such that increasing the level of expression of the polypeptide increases the amount of transport of one or more steviol glycosides across the membrane of a cell (in comparison with a corresponding cell having a lower level of expression of the polypeptide). Conversely, decreasing the level of expression of the polypeptide may decrease the amount of transport of one or more steviol glycosides across the membrane of a cell (in comparison with a corresponding cell having a higher level of expression of the polypeptide).

Typically, a recombinant host of the invention is capable of producing a steviol glycoside. For example, a recombinant host of the invention may be capable of producing one or more of, for example but not limited to, steviol-13-monoside, steviol-19-monoside, 13-[(β-D-Glucopyranosyl)oxy)kaur-16-en-18-oic acid 2-O-β-D-glucopyranosyl-β-D-glucopyranosyl ester, rubusoside, stevioside, steviol-19-diside, steviolbioside, rebA, rebB, rebC, rebD, rebE or rebM. A recombinant host of the invention may be capable of producing one or more of the steviol glycosides set out in Ceunen and Geuns, Journal of Natural Products 76(6), 1201-1228, 2013.

Thus, a cell of the invention may be one in which the amount of total amount of steviol glycosides outside the cell as compared with inside the cell is greater or less than compared with a corresponding cell which either does not overexpress or does not have a reduced level of expression of a cell of the invention.

Alternatively, a cell of the invention may have the same total amount of steviol glycosides outside the cell as compared with inside the cell compared with a corresponding cell which either does not overexpress or does not have a reduced level of expression of a cell of the invention, but may have an altered distribution of steviol glycosides inside and outside the cell.

Thus, a recombinant host of the invention is capable of producing a steviol glycoside. For example, a recombinant host of the invention may be capable of producing one or more of, for example, steviol-13-monoside, steviol-19-monoside, 13-[(β-D-Glucopyranosyl)oxy)kaur-16-en-18-oic acid 2-O-β-D-glucopyranosyl-β-D-glucopyranosyl ester, rubusoside, stevioside, steviol-19-diside, steviolbioside, rebA, rebB, rebC, rebD, rebE or rebM.

Thus, a recombinant host of the invention may be one in which at least about 10%, at least about 20%, at least about 30%, at least about 40%, at least about 50% of the rebA produced by the cell is outside the cell.

Thus, a recombinant host of the invention may be one in which at least about 10%, at least about 20%, at least about 30%, at least about 40%, at least about 50% of the rebD produced by the cell is outside the cell.

Thus, a recombinant host of the invention may be one in which at least about 10%, at least about 20%, at least about 30%, at least about 40%, at least about 50% of the rebM produced by the cell is outside the cell.

A recombinant cell of the invention may be one in which no more than about 50%, no more than about 40%, no more than about 30%, no more than about 20%, no more than about 10% of the rebA produced by the cell is outside the cell.

A recombinant cell of the invention may be one in which no more than about 50%, no more than about 40%, no more than about 30%, no more than about 20%, no more than about 10% of the rebD produced by the cell is outside the cell.

A recombinant cell of the invention may be one in which no more than about 50%, no more than about 40%, no more than about 30%, no more than about 20%, no more than about 10% of the rebM produced by the cell is outside the cell.

A recombinant cell of the invention may be one where the average glycosylation number of the steviol glycosides is at least 3, at least 4, at least 5, at least 6 or more. The average glycosylation number may be increased or decreased in comparison with a corresponding cell not modified according to the invention. For example, average glycosylation may decrease when a polypeptide as described herein is overexpressed. For example, average glycosylation may increase (in particular in a cell itself) when expression of a polypeptide of the invention is reduced.

The average glycosylation may refer to that in the supernatant of a recombinant cell of the invention or to the average glycosylation in the broth (pellet+supernatant).

The invention thus provides a recombinant cell capable of producing a steviol glycoside either overexpressing or deficient in the expression of a polypeptide comprising the amino acid sequence set forth in SEQ ID NO: 35 or SEQ ID NO: 38 or an amino acid sequence having at least about 50% sequence identity to either thereto. Such an amino acid sequence has an effect of steviol glycoside transport, i.e. is a mediator of steviol glycoside transport.

The polypeptide may also be defined as one comprising the following amino acid sequence (or an amino acid sequence having at least about 45% sequence identity thereto):

```
                                          (SEQ ID NO: 35)
MSALNTDALESQPDFKFQRQKRLMSPFMSKKVPPIPTKEERKPYGEYH

TNILFRIMFWWLNPILNVGYKRTLTEQDLFYLDNSQTMDTLYETFKSH

LKTTIEKSMKKYLQEKYSKEGKTYDPSSIPTAEDLKDFQIPIYAIPLC

LFKTLYWQYSLGNLYKVLSDCTSATTPLLQKKLINFVQMKSFTALGST

GKGVGYAIGVCLMIFFQAITVNHAFHNLQICGAKSKAILTRMLLDKSM

SVDARGNHFFPASKVQSMISTDLNRVDLAIGFFPPFALTCVFPIAICIG

LLIWNVGVSALVGIAIFVANVGLLAVSIPRLMRFRIKAMVFTDKRVTL

MKELLKNFKMIKFYSWENSYARRIQDARFKEMKLILSLQSLRNIVMSV
```

```
SFAMPTLASMATFCTAFDITSGKNAASLFSSLSLFQVLSMQFMLAPVA

LNTAADMMVSMKKFNQFLAHADLDPEQYRIEEFHDDKLAVKVDNATFE

WDTFDDDKVEDPALEFEKQDNDSLEKVSSHNTVDYDSTEKIRNDTSSI

DSTKILEKTAFPGLRNINLEIKKGEFVVVTGSIGAGKSSLLQAISGLM

KRVSGKVYVDGDLLLCGYPWVQNATIRDNILFGLPFDQEKYDQVVYAC

SLQSDFNQFQGGDMTEVGERGITLSGGQKARINLARSVYADKDIILLD

DVLSAVDAKVGRHIVDTCLLGLLKDKTRIMATHQLSLIDSADRMIFLN

GDGSIDCGTISELKDRNEKLNELLSHQKDKANDSDEELELQEEIESKE

QHLKEDLSEVKHEIKEEQKKMEISGDVGEEFEHADEHKEIVRIIGDEE

RAVNALKADVYINYAKLAFGKLGLFSLMLFVTVAALQTYCNMFTNTWL

SFWIEEKFHGRSKSFYMGIYIMFAFLYTFFLAAFFYSMCYFCNRASKY

LNYKASEKILHVPMSFMDISPIGRVLNRFTKDTDVLDNEILDQFRQFL

SPFCNAIGTIVLCIIYIPWFAIAVPLIVTFYVLVANYYQASAREIKRL

EAVKRSLVFGHFNEALSGKETIKAYRAIDRVKQRLNKLIDGQNEAYFL

TIVNQRWLGANLSILSFCMVFIISFLCVFRVFNISAASTGLLLTYVIN

LTNTITMMMRAMTQVENEFNSVERLNHYAFDLVQEAPYEIPENDPPQD

WPKYGEIIFKDVSMRYRPELPFVLKNINLSIGKGEKIGFCGRTGAGKS

TFMTCLYRISEFEGTIVIDDVDISKLGLHKLRSKLTIIPQDPVLFVGS

IRENLDPFGEYSDEELWEALTISGLINKEDLNEVKKQNENDDNLNKFH

LIRMVEDDGVNFSIGERQLIALARALVRKTKILILDEATSSVDYATDS

RIQKTIATEFDDCMILCIAHRLNTILNYDKIVVMDKGEIVEFDKPRSL

FMREEGVFRSMCEQANITIEDFP;
or
                                          (SEQ ID NO: 38)
MKSDNIAMEDLPDSKYLKQRRLLTPLMSKKVPPIPSEDERKAYGEYYT

NPVSRMMFWWLNPILKVGYRRTLTENDLFYLEDRQRTETLYEIFRGYL

DEEIARAWKKSQESSDDPREFKLPIYIIPLCLFKTMKWEYSRGILQKI

LGDCASATTPLLQKKLINFVQVKTFSNVGNTGQGVGYAIGVCLMIFFQ

VLMLTHAFHNFQISGAKAKAVLTRLLLDKSLTVDARGNHYFPASKIQS

MISTDLNRIDLAVGFAPVGFVTIFPIIICIALLIWNVGVSALVGIGVF

IANIFVLGLFVSSLMLYREKAMVFTDKRVNLVKELLKNFKMIKFYSWE

NSYQDRIENARNNEMKYILRLQLLRNFVFSLAFAMPVLASMATFCTAF

KITDGKSAASVFSSLSLFEVLSLQFILAPFSLNSTVDMMVSVKKINQF

LQHKDTNPNEFSVEKFSDSTLAIKVDNASFEWDTFEDEEKDYEEEAKT

KDNIEDEDHNCATETIKGKITVDYKSDSDSISSTLTKGVKTAFPGLNN

INLEIAKGEFIVVTGAIGSGKSSLLQAISGLMKRTSGEVYVDGDLLLC

GYPWVQNSTIRENILFGLPFNKERYDQVVYSCSLQSDFDQFQGGDMTE

VGERGITLSGGQKARINLARSVYADKDIILLDDVLSAVDAKVGKHIVN

TCILGLLGGKTRIMATHQLSLIDSADRMVFLNGDTIDFGTIPELRKR

NQKLIELLQHQRDPGQDKEDLSNDLDIQGSTDEGQQIEHADEHKEIVK

IIGDEEKAVNALSFQVYYNYCKLAFGKLGYISMLVFIIVSSLETFTQI

FTNTWLSFWIEDKFVSRSKNFYMGIYIMFAFLYAIMLCFFLFLLGYFC

VKAAERLNIKASRKILHVPMSFMDISPIGRVLNRFTKDTDVLDNELLE

QLIQFLSPLFNCFGIIILCIVYIPWFAIGVPIILGFYFIIASYYQASA

REIKRLEAVKRSFVFGHFHEVLTGKDTIKAYNAIDRMKLKLNKLIDEQ

NEAYYLTIANQRWLGANLAIVSFSMVFVISFLCIFRVFNISAASTGLL

LTYVIALTDSITMIMRAMTQVENEFNSVERVNHYAFDLIQEAPYEIPE

NDPAEDWPQHGKIEFKDVSMRYRPELPFVLKNINLSVREQEKIGFCGR

TGAGKSTFMTCLYRITEYEGLISIDGVDISRLGLHRLRSKLTIIPQDP

VLFVGTIRENLDPFTEHSDDELWEALAISGLIEREDLEVVKGQEKIGG

NDSGKLHKFHLVRMVEDDGINFSLGERQLIALARALVRKSKILILDEA

TSSVDYATDSKIQRTIASEFRDCTILCIAHRLNTILGYDKIVVMDNGE

IVEFENPKLLFMRENSVFRSMCEQANITINDFE
```

A polypeptide, typically having steviol glycoside transport mediating activity, may comprise an amino acid sequence having at least about 50%, at least about 55%, at least about 60%, at least about 65%, at least about 70%, at least about 75%, at least about 80%, at least about 85%, at least about, 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% sequence identity to SEQ ID NO: 35.

A polypeptide, typically having steviol glycoside transport mediating activity, may comprise an amino acid sequence having at least about 50%, at least about 55%, at least about 60%, at least about 65%, at least about 70%, at least about 75%, at least about 80%, at least about 85%, at least about, 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% sequence identity to SEQ ID NO: 38.

A polypeptide, typically having steviol glycoside transport mediating activity, encoded by a recombinant nucleic acid present in a recombinant host of the invention may comprise an amino acid sequence which is a fragment of an amino acid sequence described herein, for example a truncated version of such an amino acid sequence.

That is to say, the invention also a recombinant host overexpressing a biologically active fragment of a polypeptide having steviol glycoside transport mediating activity as described herein.

Biologically active fragments of a polypeptide of the invention include polypeptides comprising amino acid sequences sufficiently identical to or derived from the amino acid sequence of SEQ ID NO: 29 which include fewer amino acids than the full-length polypeptide as given in SEQ ID NO: 29, but which exhibit at least one biological activity of the corresponding full-length polypeptide.

Typically, biologically active fragments comprise a domain or motif with at least one activity of the polypeptide of the invention. A biologically active fragment of a polypeptide of the invention can be a polypeptide which is, for example, about 10, about 25, about 50, about 100 or more amino acids in length or at least about 100 amino acids, at least 150, 200, 250, 300, 350, 400, 600, 1000 amino acids in length, or of a length up to the total number of amino acids of the polypeptide of the invention. Moreover, other biologically active portions, in which other regions of the polypeptide are deleted, can be prepared by recombinant techniques and evaluated for one or more of the biological activities of the native form of a polypeptide of the invention. The invention also features nucleic acid fragments which encode the above biologically active fragments of the polypeptide of the invention.

A recombinant host of the invention may overexpress or be deficient in such a polypeptide.

A recombinant host of the invention may comprise recombinant nucleic acid sequences encoding more than one such polypeptide, for example two, three, four or more such polypeptides. The polypeptides thus encoded may be the same or different.

A recombinant cell of the invention may be modified so as to reduce the expression level of more than one such polypeptide, for example two, three, four or more such polypeptides.

An overexpressed polypeptide encoded by a recombinant nucleic acid present in a recombinant host may be one which is obtainable from or derived from or found in an organism of the genus *Pichia*, for example one which is obtainable from or derived from or found in a *Pichia kudriavzeii*.

As used herein, the term "polypeptide" refers to a molecule comprising amino acid residues linked by peptide bonds and containing more than five amino acid residues. The amino acids are identified by either the single-letter or three-letter designations. The term "protein" as used herein is synonymous with the term "polypeptide" and may also refer to two or more polypeptides. Thus, the terms "protein", "peptide" and "polypeptide" can be used interchangeably.

Polypeptides may optionally be modified (e.g., glycosylated, phosphorylated, acylated, farnesylated, prenylated, sulfonated, and the like) to add functionality. Polypeptides exhibiting activity may be referred to as enzymes. It will be understood that, as a result of the degeneracy of the genetic code, a multitude of nucleotide sequences encoding a given polypeptide may be produced.

A polypeptide encoded by a recombinant nucleic acid for use in a recombinant host of the invention may comprise a signal peptide and/or a propeptide sequence. In the event that a polypeptide of the invention comprises a signal peptide and/or a propeptide, sequence identity may be calculated over the mature polypeptide sequence.

A recombinant nucleic acid sequence for use in a recombinant host of the invention may be provided in the form of a nucleic acid construct. The term "nucleic acid construct" refers to a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term "expression cassette" when the nucleic acid construct contains all the control sequences required for expression of a coding sequence, wherein said control sequences are operably linked to said coding sequence.

A recombinant nucleic acid sequence for use in a recombinant host of the invention may be provided in the form of an expression vector, wherein the polynucleotide sequence is operably linked to at least one control sequence for the expression of the polynucleotide sequence in a recombinant host cell.

The term "operably linked" as used herein refers to two or more nucleic acid sequence elements that are physically linked and are in a functional relationship with each other. For instance, a promoter is operably linked to a coding sequence if the promoter is able to initiate or regulate the transcription or expression of a coding sequence, in which case the coding sequence should be understood as being "under the control of" the promoter. Generally, when two nucleic acid sequences are operably linked, they will be in the same orientation and usually also in the same reading frame. They usually will be essentially contiguous, although this may not be required.

An expression vector comprises a polynucleotide coding for a polypeptide as described herein, operably linked to the appropriate control sequences (such as a promoter, and transcriptional and translational stop signals) for expression and/or translation in vitro, or in the host cell of the polynucleotide.

The expression vector may be any vector (e.g., a plasmid or virus), which can be conveniently subjected to recombinant DNA procedures and can bring about the expression of the polynucleotide. The choice of the vector will typically depend on the compatibility of the vector with the cell into which the vector is to be introduced. The vectors may be linear or closed circular plasmids. The vector may be an autonomously replicating vector, i.e., a vector, which exists as an extra-chromosomal entity, the replication of which is independent of chromosomal replication, e.g., a plasmid, an extra-chromosomal element, a mini-chromosome, or an artificial chromosome.

Alternatively, the vector may be one which, when introduced into the host cell, is integrated into the genome and replicated together with the chromosome(s) into which it has been integrated. The integrative cloning vector may integrate at random or at a predetermined target locus in the chromosomes of the host cell. A vector may comprise one or more selectable markers, which permit easy selection of transformed cells.

A recombinant host capable of producing a steviol glycoside which has been modified, preferably in its genome, to result in a deficiency in the production of a polypeptide described herein may be generated according to methods well known to those skilled in the art. A sequence encoding a polypeptide as described herein may be modified such that less or no expression of the polypeptide takes place. A sequence encoding a polypeptide as described herein may be partially or entirely deleted, for example.

A recombinant host of the invention may comprise any polypeptide as described herein. A recombinant host of the invention may overexpress or be deficient in any polypeptide described herein. Typically, a recombinant host of the invention is capable of producing a steviol glycoside. For example, a recombinant host of the invention may be capable of producing one or more of, for example, steviol-13-monoside, steviol-19-monoside, 13-[(β-D-Glucopyranosyl)oxy)kaur-16-en-18-oic acid 2-O-β-D-glucopyranosyl-β-D-glucopyranosyl ester, rubusoside, stevioside, steviol-19-diside, steviolbioside, rebA, rebE, rebD or rebM.

A recombinant host of the invention may comprise one or more recombinant nucleic acid sequences encoding one or more polypeptides having UDP-glycosyltransferase (UGT) activity.

For the purposes of this invention, a polypeptide having UGT activity is one which has glycosyltransferase activity (EC 2.4), i.e. that can act as a catalyst for the transfer of a monosaccharide unit from an activated nucleotide sugar (also known as the "glycosyl donor") to a glycosyl acceptor molecule, usually an alcohol. The glycosyl donor for a UGT is typically the nucleotide sugar uridine diphosphate glucose (uracil-diphosphate glucose, UDP-glucose).

Figure 14:
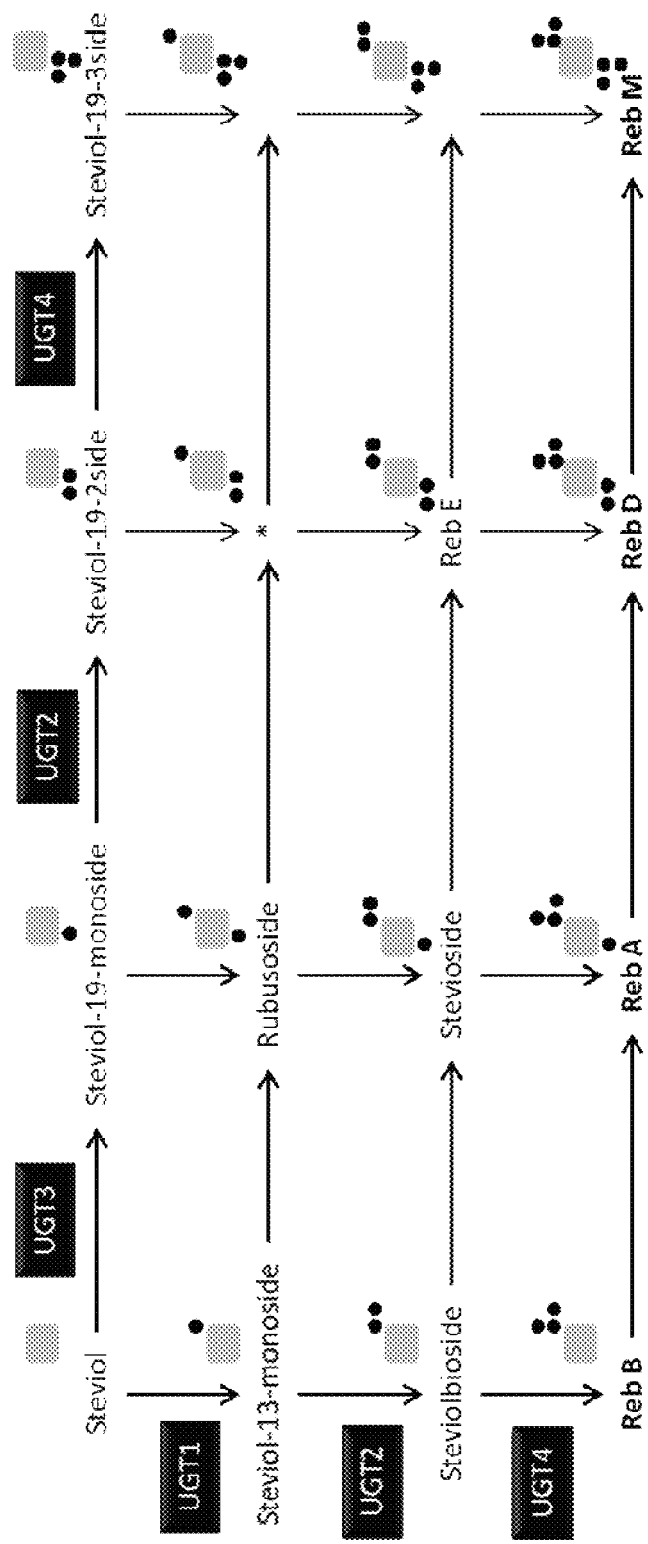
FIG. 14 sets out a schematic diagram of the potential pathways leading to biosynthesis of steviol glycosides. The compound shown with an asterisk is 13-[(β-D-Glucopyranosyl)oxy]kaur-16-en-18-oic acid 2-O-β-D-glucopyranosyl-β-D-glucopyranosyl ester.

Such additional UGTs may be selected so as to produce a desired steviol glycoside. Schematic diagrams of steviol glycoside formation are set out in Humphrey et al., Plant Molecular Biology (2006) 61: 47-62 and Mohamed et al., J. Plant Physiology 168 (2011) 1136-1141. In addition, FIG. 14 sets out a schematic diagram of steviol glycoside formation.

A recombinant host of the invention may thus comprise one or more recombinant nucleic acid sequences encoding one or more of:
  (i) a polypeptide having UGT74G1 activity;
  (ii) a polypeptide having UGT2 activity;
  (iii) a polypeptide having UGT85C2 activity; and
  (iv) a polypeptide having UGT76G1 activity.

A recombinant yeast suitable for use in the invention may comprise a nucleotide sequence encoding a polypeptide capable of catalyzing the addition of a C-13-glucose to steviol. That is to say, a recombinant yeast suitable for use in a method of the invention may comprise a UGT which is capable of catalyzing a reaction in which steviol is converted to steviolmonoside.

Such a recombinant yeast suitable for use in a method of the invention may comprise a nucleotide sequence encoding a polypeptide having the activity shown by UDP-glycosyl-transferase (UGT) UGT85C2, whereby the nucleotide sequence upon transformation of the yeast confers on that yeast the ability to convert steviol to steviolmonoside.

UGT85C2 activity is transfer of a glucose unit to the 13-OH of steviol. Thus, a suitable UGT85C2 may function as a uridine 5'-diphospho glucosyl: steviol 13-OH transferase, and a uridine 5'-diphospho glucosyl: steviol-19-0-glucoside 13-OH transferase. A functional UGT85C2 polypeptides may also catalyze glucosyl transferase reactions that utilize steviol glycoside substrates other than steviol and steviol-19-O-glucoside. Such sequences may be referred to as UGT1 sequences herein.

A recombinant yeast suitable for use in the invention may comprise a nucleotide sequence encoding a polypeptide which has UGT2 activity.

A polypeptide having UGT2 activity is one which functions as a uridine 5'-diphospho glucosyl: steviol-13-O-glucoside transferase (also referred to as a steviol-13-monoglucoside 1,2-glucosylase), transferring a glucose moiety to the C-2' of the 13-O-glucose of the acceptor molecule, steviol-13-O-glucoside. Typically, a suitable UGT2 polypeptide also functions as a uridine 5'-diphospho glucosyl: rubusoside transferase transferring a glucose moiety to the C-2' of the 13-O-glucose of the acceptor molecule, rubusoside.

A polypeptide having UGT2 activity may also catalyze reactions that utilize steviol glycoside substrates other than steviol-13-0-glucoside and rubusoside, e.g., functional UGT2 polypeptides may utilize stevioside as a substrate, transferring a glucose moiety to the C-2' of the 19-O-glucose residue to produce rebaudioside E. A functional UGT2 polypeptides may also utilize rebaudioside A as a substrate, transferring a glucose moiety to the C-2' of the 19-O-glucose residue to produce rebaudioside D. However, a functional UGT2 polypeptide may be one which does not transfer a glucose moiety to steviol compounds having a 1,3-bound glucose at the C-13 position, i.e., transfer of a glucose moiety to steviol 1,3-bioside and 1,3-stevioside typically does not occur.

A polypeptide having UGT2 activity may also transfer sugar moieties from donors other than uridine diphosphate glucose. For example, a polypeptide having UGT2 activity act as a uridine 5'-diphospho D-xylosyl: steviol-13-O-glucoside transferase, transferring a xylose moiety to the C-2' of the 13-O-glucose of the acceptor molecule, steviol-13-O-glucoside. As another example, a polypeptide having UGT2 activity may act as a uridine 5'-diphospho L-rhamnosyl: steviol-13-0-glucoside transferase, transferring a rhamnose moiety to the C-2' of the 13-O-glucose of the acceptor molecule, steviol.

A recombinant yeast suitable for use in the method of the invention may comprise a nucleotide sequence encoding a polypeptide having UGT activity may comprise a nucleotide sequence encoding a polypeptide capable of catalyzing the addition of a C-19-glucose to steviolbioside. That is to say, a recombinant yeast of the invention may comprise a UGT which is capable of catalyzing a reaction in which steviolbioside is converted to stevioside. Accordingly, such a recombinant yeast may be capable of converting steviolbioside to stevioside. Expression of such a nucleotide sequence may confer on the recombinant yeast the ability to produce at least stevioside.

A recombinant yeast suitable for use in a method of the invention may thus also comprise a nucleotide sequence encoding a polypeptide having the activity shown by UDP-glycosyltransferase (UGT) UGT74G1, whereby the nucleotide sequence upon transformation of the yeast confers on the cell the ability to convert steviolbioside to stevioside.

Suitable UGT74G1 polypeptides may be capable of transferring a glucose unit to the 13-OH and/or the 19-COOH of steviol. A suitable UGT74G1 polypeptide may function as a uridine 5'-diphospho glucosyl: steviol 19-COOH transferase and/or a uridine 5'-diphospho glucosyl: steviol-13-O-glucoside 19-COOH transferase. Functional UGT74G1 polypeptides also may catalyze glycosyl transferase reactions that utilize steviol glycoside substrates other than steviol and steviol-13-O-glucoside, or that transfer sugar moieties from donors other than uridine diphosphate glucose. Such sequences may be referred to herein as UGT3 sequences.

A recombinant yeast suitable for use in a method the invention may comprise a nucleotide sequence encoding a polypeptide capable of catalyzing glucosylation of the C-3' of the glucose at the C-13 position of stevioside. That is to say, a recombinant yeast suitable for use in a method of the invention may comprise a UGT which is capable of catalyzing a reaction in which stevioside is converted to rebaudioside A. Accordingly, such a recombinant yeast may be capable of converting stevioside to rebaudioside A. Expression of such a nucleotide sequence may confer on the yeast the ability to produce at least rebaudioside A.

A recombinant yeast suitable for use in a method of the invention may thus also comprise a nucleotide sequence encoding a polypeptide having the activity shown by UDP-glycosyltransferase (UGT) UGT76G1, whereby the nucleotide sequence upon transformation of a yeast confers on that yeast the ability to convert stevioside to rebaudioside A.

A suitable UGT76G1 adds a glucose moiety to the C-3' of the C-13-O-glucose of the acceptor molecule, a steviol 1,2 glycoside. Thus, UGT76G1 functions, for example, as a uridine 5'-diphospho glucosyl: steviol 13-0-1,2 glucoside C-3' glucosyl transferase and a uridine 5'-diphospho glucosyl: steviol-19-0-glucose, 13-0-1,2 bioside C-3' glucosyl transferase. Functional UGT76G1 polypeptides may also catalyze glucosyl transferase reactions that utilize steviol glycoside substrates that contain sugars other than glucose, e.g., steviol rhamnosides and steviol xylosides. Such sequences may be referred to herein as UGT4 sequences. A UGT4 may alternatively or in addition be capable of converting RebD to RebM.

A recombinant yeast suitable for use in a method of the invention typically comprises nucleotide sequences encoding at least one polypeptide having UGT1 activity, at least one polypeptide having UGT2 activity, least one polypeptide having UGT3 activity and at least one polypeptide having UGT4 activity. One or more of these nucleic acid sequences may be recombinant. A given nucleic acid may encode a polypeptide having one or more of the above activities. For example, a nucleic acid encode for a polypeptide which has two, three or four of the activities set out above. Preferably, a recombinant yeast for use in the method of the invention comprises UGT1, UGT2 and UGT3 and UGT4 activity. Suitable UGT1, UGT2, UGT3 and UGT4 sequences are described in Table 1 of WO2015/007748.

A recombinant host of the invention may comprise two or more nucleic acid sequences encoding a polypeptide having any one UGT activity, for example UGT1, 2, 3 or 4, activity. Where a recombinant host of the invention comprises two or more nucleic acid sequence encoding a polypeptide having any one UGT activity, those nucleic acid sequences may be the same or different and/or may encode the same or different polypeptides. In particular, a recombinant host of the invention may comprise a nucleic acid sequence encoding a two different UGT2 polypeptides.

A recombinant host according to the invention may comprise one or more recombinant nucleotide sequence(s) encoding one of more of:
a polypeptide having ent-copalyl pyrophosphate synthase activity;
a polypeptide having ent-Kaurene synthase activity;
a polypeptide having ent-Kaurene oxidase activity; and
a polypeptide having kaurenoic acid 13-hydroxylase activity.

For the purposes of this invention, a polypeptide having ent-copalyl pyrophosphate synthase (EC 5.5.1.13) is capable of catalyzing the chemical reaction:

This enzyme has one substrate, geranylgeranyl pyrophosphate, and one product, ent-copalyl pyrophosphate. This enzyme participates in gibberellin biosynthesis. This enzyme belongs to the family of isomerase, specifically the class of intramolecular lyases. The systematic name of this enzyme class is ent-copalyl-diphosphate lyase (decyclizing). Other names in common use include having ent-copalyl pyrophosphate synthase, ent-kaurene synthase A, and ent-kaurene synthetase A.

Suitable nucleic acid sequences encoding an ent-copalyl pyrophosphate synthase may for instance comprise a sequence as set out in SEQ ID. NO: 1, 3, 5, 7, 17, 19, 59, 61, 141, 142, 151, 152, 153, 154, 159, 160, 182 or 184 of WO2015/007748.

For the purposes of this invention, a polypeptide having ent-kaurene synthase activity (EC 4.2.3.19) is a polypeptide that is capable of catalyzing the chemical reaction:

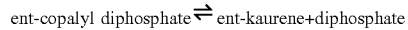

Hence, this enzyme has one substrate, ent-copalyl diphosphate, and two products, ent-kaurene and diphosphate.

This enzyme belongs to the family of lyases, specifically those carbon-oxygen lyases acting on phosphates. The systematic name of this enzyme class is ent-copalyl-diphosphate diphosphate-lyase (cyclizing, ent-kaurene-forming). Other names in common use include ent-kaurene synthase B, ent-kaurene synthetase B, ent-copalyl-diphosphate diphosphate-lyase, and (cyclizing). This enzyme participates in diterpenoid biosynthesis.

Suitable nucleic acid sequences encoding an ent-Kaurene synthase may for instance comprise a sequence as set out in SEQ ID. NO: 9, 11, 13, 15, 17, 19, 63, 65, 143, 144, 155, 156, 157, 158, 159, 160, 183 or 184 of WO2015/007748.

ent-copalyl diphosphate synthases may also have a distinct ent-kaurene synthase activity associated with the same protein molecule. The reaction catalyzed by ent-kaurene synthase is the next step in the biosynthetic pathway to gibberellins. The two types of enzymic activity are distinct, and site-directed mutagenesis to suppress the ent-kaurene synthase activity of the protein leads to build up of ent-copalyl pyrophosphate.

Accordingly, a single nucleotide sequence used in a recombinant host of the invention may encode a polypeptide having ent-copalyl pyrophosphate synthase activity and ent-kaurene synthase activity. Alternatively, the two activities may be encoded two distinct, separate nucleotide sequences.

For the purposes of this invention, a polypeptide having ent-kaurene oxidase activity (EC 1.14.13.78) is a polypep-

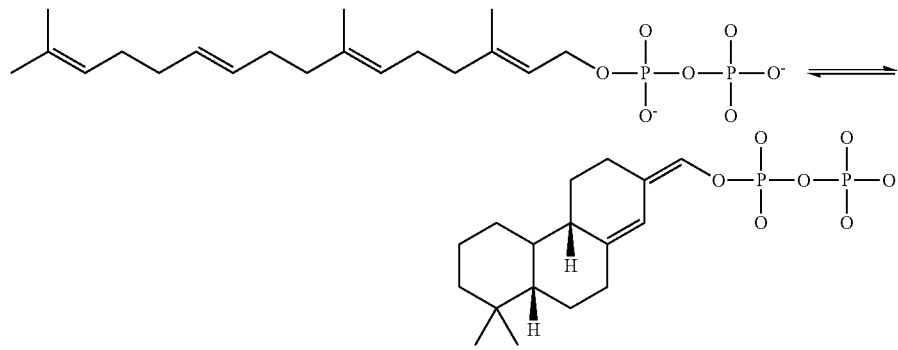

tide which is capable of catalysing three successive oxidations of the 4-methyl group of ent-kaurene to give kaurenoic acid. Such activity typically requires the presence of a cytochrome P450.

Suitable nucleic acid sequences encoding an ent-Kaurene oxidase may for instance comprise a sequence as set out in SEQ ID. NO: 21, 23, 25, 67, 85, 145, 161, 162, 163, 180 or 186 of WO2015/007748.

For the purposes of the invention, a polypeptide having kaurenoic acid 13-hydroxylase activity (EC 1.14.13) is one which is capable of catalyzing the formation of steviol (ent-kaur-16-en-13-ol-19-oic acid) using NADPH and O2. Such activity may also be referred to as ent-ka 13-hydroxylase activity.

Suitable nucleic acid sequences encoding a kaurenoic acid 13-hydroxylase may for instance comprise a sequence as set out in SEQ ID. NO: 27, 29, 31, 33, 69, 89, 91, 93, 95, 97, 146, 164, 165, 166, 167 or 185 of WO2015/007748.

A recombinant host of the invention may comprise a recombinant nucleic acid sequence encoding a polypeptide having NADPH-cytochrome p450 reductase activity. That is to say, a recombinant host of the invention may be capable of expressing a nucleotide sequence encoding a polypeptide having NADPH-cytochrome p450 reductase activity. For the purposes of the invention, a polypeptide having NADPH-Cytochrome P450 reductase activity (EC 1.6.2.4; also known as NADPH:ferrihemoprotein oxidoreductase, NADPH:hemoprotein oxidoreductase, NADPH:P450 oxidoreductase, P450 reductase, POR, CPR, CYPOR) is typically one which is a membrane-bound enzyme allowing electron transfer to cytochrome P450 in the microsome of the eukaryotic cell from a FAD- and FMN-containing enzyme NADPH:cytochrome P450 reductase (POR; EC 1.6.2.4).

In a recombinant host of the invention, the ability of the host to produce geranylgeranyl diphosphate (GGPP) may be upregulated. Upregulated in the context of this invention implies that the recombinant host produces more GGPP than an equivalent non-recombinant host.

Accordingly, a recombinant host of the invention may comprise one or more nucleotide sequence(s) encoding hydroxymethylglutaryi-CoA reductase, farnesyl-pyrophosphate synthetase and geranylgeranyl diphosphate synthase, whereby the nucleotide sequence(s) upon transformation of a host confer(s) on that host the ability to produce elevated levels of GGPP. Thus, a recombinant host according to the invention may comprise one or more recombinant nucleic acid sequence(s) encoding one or more of hydroxymethylglutaryl-CoA reductase, farnesyl-pyrophosphate synthetase and geranylgeranyl diphosphate synthase.

Accordingly, a recombinant host of the invention may comprise nucleic acid sequences encoding one or more of:
a polypeptide having hydroxymethylglutaryl-CoA reductase activity;
a polypeptide having farnesyl-pyrophosphate synthetase activity; and A recombinant host of the invention may be, for example, an multicellular organism or a cell thereof or a unicellular organism. A host of the invention may be a prokaryotic, archaebacterial or eukaryotic host cell.

A prokaryotic host cell may, but is not limited to, a bacterial host cell. An eukaryotic host cell may be, but is not limited to, a yeast, a fungus, an amoeba, an algae, an animal, an insect host cell.

An eukaryotic host cell may be a fungal host cell. "Fungi" include all species of the subdivision *Eumycotina* (Alexopoulos, C. J., 1962, In: Introductory Mycology, John Wiley & Sons, Inc., New York). The term fungus thus includes among others filamentous fungi and yeast.

"Filamentous fungi" are herein defined as eukaryotic microorganisms that include all filamentous forms of the subdivision *Eumycotina* and *Oomycota* (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligatory aerobic. Filamentous fungal strains include, but are not limited to, strains of *Acremonium, Aspergillus, Agaricus, Aureobasidium, Cryptococcus, Corynascus, Chrysosporium, Filibasidium, Fusarium, Humicola, Magnaporthe, Monascus, Mucor, Myceliophthora, Mortierella, Neocallimastix, Neurospora, Paecilomyces, Penicillium, Piromyces, Phanerochaete Podospora, Pycnoporus,* *Rhizopus, Schizophyllum, Sordaria, Talaromyces, Rasmsonia, Thermoascus, Thielavia, Tolypocladium, Trametes* and *Trichoderma*. Preferred filamentous fungal strains that may serve as host cells belong to the species *Aspergillus niger, Aspergillus oryzae, Aspergillus fumigatus, Penicillium chrysogenum, Penicillium citrinum, Acremonium chrysogenum, Trichoderma reesei, Rasamsonia emersonii* (formerly known as *Talaromyces emersonii*), *Aspergillus sojae, Chrysosporium lucknowense, Myceliophtora thermophyla*. Reference host cells for the comparison of fermentation characteristics of transformed and untransformed cells, include e.g. *Aspergillus niger* CBS120.49, CBS 513.88, *Aspergillus oryzae* ATCC16868, ATCC 20423, IFO 4177, ATCC 1011, ATCC 9576, ATCC14488-14491, ATCC 11601, ATCC12892, *Aspergillus fumigatus* AF293 (CBS101355), *P. chrysogenum* CBS 455.95, *Penicillium citrinum* ATCC 38065, *Penicillium chrysogenum* P2, *Acremonium chrysogenum* ATCC 36225, ATCC 48272, *Trichoderma reesei* ATCC 26921, ATCC 56765, ATCC 26921, *Aspergillus sojae* ATCC11906, *Chrysosporium lucknowense* ATCC44006 and derivatives of all of these strains. Particularly preferred as filamentous fungal host cell are *Aspergillus niger* CBS 513.88 and derivatives thereof.

An eukaryotic host cell may be a yeast cell. Preferred yeast host cells may be selected from the genera: *Saccharomyces* (e.g., *S. cerevisiae, S. bayanus, S. pastorianus, S. carlsbergensis*), *Brettanomyces, Kluyveromyces, Candida* (e.g., *C. krusei, C. revkaufi, C. pulcherrima, C. tropicalis, C. utilis*), *Issatchenkia* (eg. *I. orientalis*) *Pichia* (e.g., *P. pastoris* and *P. kudriavzevii*), *Schizosaccharomyces, Hansenula, Kloeckera, Pachysolen, Schwanniomyces, Trichosporon, Yarrowia* (e.g., *Y. lipolytica* (formerly classified as *Candida lipolytica*)), *Yamadazyma*.

Prokaryotic host cells may be bacterial host cells. Bacterial host cell may be Gram negative or Gram positive bacteria. Examples of bacteria include, but are not limited to, bacteria belonging to the genus *Bacillus* (e.g., *B. subtilis, B. amyloliquefaciens, B. licheniformis, B. puntis, B. megaterium, B. halodurans, B. pumilus,*), *Acinetobacter, Nocardia, Xanthobacter, Escherichia* (e.g., *E. coli* (e.g., strains DH 1 OB, Stbl2, DH5-alpha, DB3, DB3.1), DB4, DB5, JDP682 and ccdA-over (e.g., U.S. application Ser. No. 09/518, 188))), *Streptomyces, Erwinia, Klebsiella, Serratia* (e.g., *S. marcessans*), *Pseudomonas* (e.g., *P. aeruginosa*), *Salmonella* (e.g., *S. typhimurium, S. typhi*). Bacteria also include, but are not limited to, photosynthetic bacteria (e.g., green non-sulfur bacteria (e.g., *Choroflexus* bacteria (e.g., *C. aurantiacus*), *Chloronema* (e.g., *C. gigateum*)), green sulfur bacteria (e.g., *Chlorobium* bacteria (e.g., *C. limicola*), *Pelodictyon* (e.g., *P. luteolum*), purple sulfur bacteria (e.g., *Chromatium* (e.g., *C. okeni*)), and purple non-sulfur bacteria (e.g., *Rhodospirillum* (e.g., *R. rubrum*), *Rhodobacter* (e.g. *R. sphaeroides, R. capsulatus*), and *Rhodomicrobium* bacteria (e.g., *R. vanellil*)).

Host Cells may be host cells from non-microbial organisms. Examples of such cells, include, but are not limited to, insect cells (e.g., *Drosophila* (e.g., *D. melanogaster*), *Spodoptera* (e.g., *S. frugiperda* Sf9 or Sf21 cells) and *Trichoplusa* (e.g., High-Five cells); nematode cells (e.g., *C. elegans* cells); avian cells; amphibian cells (e.g., *Xenopus laevis* cells); reptilian cells; and mammalian cells (e.g., NIH3T3, 293, CHO, COS, VERO, C127, BHK, Per-C6, Bowes melanoma and HeLa cells).

A recombinant host according to the present invention may be able to grow on any suitable carbon source known in the art and convert it to a steviol glycoside. The recombinant host may be able to convert directly plant biomass, celluloses, hemicelluloses, pectines, rhamnose, galactose, fucose, maltose, maltodextrines, ribose, ribulose, or starch, starch derivatives, sucrose, lactose and glycerol. Hence, a preferred host expresses enzymes such as cellulases (endo-cellulases and exocellulases) and hemicellulases (e.g. endo- and exo-xylanases, arabinases) necessary for the conversion of cellulose into glucose monomers and hemicellulose into xylose and arabinose monomers, pectinases able to convert pectines into glucuronic acid and galacturonic acid or amylases to convert starch into glucose monomers. Preferably, the host is able to convert a carbon source selected from the group consisting of glucose, xylose, arabinose, sucrose, lactose and glycerol. The host cell may for instance be a eukaryotic host cell as described in WO03/062430, WO06/009434, EP1499708B1, WO2006096130 or WO04/099381.

Thus, in a further aspect, the invention also provides a process for the preparation of a steviol glycoside which comprises fermenting a recombinant host of the invention which is capable of producing at least one steviol glycoside in a suitable fermentation medium, and optionally recovering the steviol glycoside.

The fermentation medium used in the process for the production of a steviol glycoside may be any suitable fermentation medium which allows growth of a particular eukaryotic host cell. The essential elements of the fermentation medium are known to the person skilled in the art and may be adapted to the host cell selected.

Preferably, the fermentation medium comprises a carbon source selected from the group consisting of plant biomass, celluloses, hemicelluloses, pectines, rhamnose, galactose, fucose, fructose, maltose, maltodextrines, ribose, ribulose, or starch, starch derivatives, sucrose, lactose, fatty acids, triglycerides and glycerol. Preferably, the fermentation medium also comprises a nitrogen source such as ureum, or an ammonium salt such as ammonium sulphate, ammonium chloride, ammoniumnitrate or ammonium phosphate.

The fermentation process according to the present invention may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity. A SSF process may be particularly attractive if starch, cellulose, hemicelluose or pectin is used as a carbon source in the fermentation process, where it may be necessary to add hydrolytic enzymes, such as cellulases, hemicellulases or pectinases to hydrolyse the substrate.

The recombinant host used in the process for the preparation of a steviol glycoside may be any suitable recombinant host as defined herein above. It may be advantageous to use a recombinant eukaryotic recombinant host according to the invention in the process since most eukaryotic cells do not require sterile conditions for propagation and are insensitive to bacteriophage infections. In addition, eukaryotic host cells may be grown at low pH to prevent bacterial contamination.

The recombinant host according to the present invention may be a facultative anaerobic microorganism. A facultative anaerobic recombinant host can be propagated aerobically to a high cell concentration. This anaerobic phase can then be carried out at high cell density which reduces the fermentation volume required substantially, and may minimize the risk of contamination with aerobic microorganisms.

The fermentation process for the production of a steviol glycoside according to the present invention may be an aerobic or an anaerobic fermentation process.

An anaerobic fermentation process may be herein defined as a fermentation process run in the absence of oxygen or in which substantially no oxygen is consumed, preferably less than 5, 2.5 or 1 mmol/L/h, and wherein organic molecules serve as both electron donor and electron acceptors. The fermentation process according to the present invention may also first be run under aerobic conditions and subsequently under anaerobic conditions.

The fermentation process may also be run under oxygen-limited, or micro-aerobical, conditions. Alternatively, the fermentation process may first be run under aerobic conditions and subsequently under oxygen-limited conditions. An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used.

The production of a steviol glycoside in the process according to the present invention may occur during the growth phase of the host cell, during the stationary (steady state) phase or during both phases. It may be possible to run the fermentation process at different temperatures.

The process for the production of a steviol glycoside may be run at a temperature which is optimal for the recombinant host. The optimum growth temperature may differ for each transformed recombinant host and is known to the person skilled in the art. The optimum temperature might be higher than optimal for wild type organisms to grow the organism efficiently under non-sterile conditions under minimal infection sensitivity and lowest cooling cost. Alternatively, the process may be carried out at a temperature which is not optimal for growth of the recombinant host.

The process for the production of a steviol glycoside according to the present invention may be carried out at any suitable pH value. If the recombinant host is a yeast, the pH in the fermentation medium preferably has a value of below 6, preferably below 5.5, preferably below 5, preferably below 4.5, preferably below 4, preferably below pH 3.5 or below pH 3.0, or below pH 2.5, preferably above pH 2. An advantage of carrying out the fermentation at these low pH values is that growth of contaminant bacteria in the fermentation medium may be prevented.

Such a process may be carried out on an industrial scale. The product of such a process is one or more steviol glycosides.

Recovery of steivol glycoside(s) from the fermentation medium may be performed by known methods in the art, for instance by distillation, vacuum extraction, solvent extraction, or evaporation.

In the process for the production of a steviol glycoside according to the invention, it may be possible to achieve a concentration of above 5 mg/l fermentation broth, preferably above 10 mg/l, preferably above 20 mg/l, preferably above 30 mg/l fermentation broth, preferably above 40 mg/l, more preferably above 50 mg/l, preferably above 60 mg/l, preferably above 70, preferably above 80 mg/l, preferably above 100 mg/l, preferably above 1 g/l, preferably above 5 g/l, preferably above 10 g/l, for example at least about 15 g/L, such as at least about 20 g/l.

The invention further provides a fermentation broth comprising a steviol glycoside obtainable by the process of the invention for the preparation of a steivol glycoside.

In the event that one or more steviol glycosides is expressed within a recombinant host of the invention, such cells may need to be treated so as to release them. Preferentially, at least one steviol glycoside, for example rebA or rebM, is produced extracellularly The invention also provides a steviol glycoside obtained by a process according to the invention for the preparation of a steviol glycoside or obtainable from a fermentation broth of the invention. Such a steviol glycoside may be a non-naturally occurring steviol glycoside, that is to say one which is not produced in plants.

Also provided is a composition obtainable by a process of the invention (which typically comprises one or more steviol glycosides). Also provided is a composition comprising two or more steviol glycosides obtainable by a process of the invention for the preparation of a steviol glycoside or obtainable from a fermentation broth of the invention. In such a composition, one or more of the steviol glycosides may be a non-naturally occurring steviol glycoside, that is to say one which is not produced in plants. These are all compositions of the invention.

A composition of the invention may be used in any application known for such compounds. In particular, such a composition may for instance be used as a sweetener, for example in a food or a beverage. According to the invention therefore, there is provided a foodstuff, feed or beverage which comprises a composition of the invention.

For example a composition of the invention may be formulated in soft drinks, as a tabletop sweetener, chewing gum, dairy product such as yoghurt (eg. plain yoghurt), cake, cereal or cereal-based food, nutraceutical, pharmaceutical, edible gel, confectionery product, cosmetic, toothpastes or other oral cavity composition, etc. In addition, a composition of the invention can be used as a sweetener not only for drinks, foodstuffs, and other products dedicated for human consumption, but also in animal feed and fodder with improved characteristics.

Accordingly, the invention provides, inter alia, a foodstuff, feed or beverage which comprises a composition of the invention.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

A composition of the invention can be used in dry or liquid forms. It can be added before or after heat treatment of food products. The amount of the sweetener depends on the purpose of usage. It can be added alone or in the combination with other compounds.

A composition of the invention may be blended with one or more further non-caloric or caloric sweeteners. Such blending may be used to improve flavour or temporal profile or stability. A wide range of both non-caloric and caloric sweeteners may be suitable for blending with a composition of the invention. For example, non-caloric sweeteners such as mogroside, monatin, aspartame, acesulfame salts, cyclamate, sucralose, saccharin salts or erythritol. Caloric sweeteners suitable for blending with a steviol glycoside or a composition of the invention include sugar alcohols and carbohydrates such as sucrose, glucose, fructose and HFCS. Sweet tasting amino acids such as glycine, alanine or serine may also be used.

A composition of the invention can be used in the combination with a sweetener suppressor, such as a natural sweetener suppressor. It may be combined with an umami taste enhancer, such as an amino acid or a salt thereof.

A composition of the invention can be combined with a polyol or sugar alcohol, a carbohydrate, a physiologically active substance or functional ingredient (for example a carotenoid, dietary fiber, fatty acid, saponin, antioxidant, nutraceutical, flavonoid, isothiocyanate, phenol, plant sterol or stanol (phytosterols and phytostanols), a polyols, a prebiotic, a probiotic, a phytoestrogen, soy protein, sulfides/thiols, amino acids, a protein, a vitamin, a mineral, and/or a substance classified based on a health benefits, such as cardiovascular, cholesterol-reducing or anti-inflammatory.

A composition of the invention may include a flavoring agent, an aroma component, a nucleotide, an organic acid, an organic acid salt, an inorganic acid, a bitter compound, a protein or protein hydrolyzate, a surfactant, a flavonoid, an astringent compound, a vitamin, a dietary fiber, an antioxidant, a fatty acid and/or a salt.

A composition of the invention may be applied as a high intensity sweetener to produce zero calorie, reduced calorie or diabetic beverages and food products with improved taste characteristics. Also it can be used in drinks, foodstuffs, pharmaceuticals, and other products in which sugar cannot be used.

In addition, a composition of the invention may be used as a sweetener not only for drinks, foodstuffs, and other products dedicated for human consumption, but also in animal feed and fodder with improved characteristics.

The examples of products where a composition of the invention can be used as a sweetening compound can be as alcoholic beverages such as vodka, wine, beer, liquor, sake, etc; natural juices, refreshing drinks, carbonated soft drinks, diet drinks, zero calorie drinks, reduced calorie drinks and foods, yogurt drinks, instant juices, instant coffee, powdered types of instant beverages, canned products, syrups, fermented soybean paste, soy sauce, vinegar, dressings, mayonnaise, ketchups, curry, soup, instant bouillon, powdered soy sauce, powdered vinegar, types of biscuits, rice biscuit, crackers, bread, chocolates, caramel, candy, chewing gum, jelly, pudding, preserved fruits and vegetables, fresh cream, jam, marmalade, flower paste, powdered milk, ice cream, sorbet, vegetables and fruits packed in bottles, canned and boiled beans, meat and foods boiled in sweetened sauce, agricultural vegetable food products, seafood, ham, sausage, fish ham, fish sausage, fish paste, deep fried fish products, dried seafood products, frozen food products, preserved seaweed, preserved meat, tobacco, medicinal products, and many others. In principal it can have unlimited applications.

The sweetened composition comprises a beverage, non-limiting examples of which include non-carbonated and carbonated beverages such as colas, ginger ales, root beers, ciders, fruit-flavored soft drinks (e.g., citrus-flavored soft drinks such as lemon-lime or orange), powdered soft drinks, and the like; fruit juices originating in fruits or vegetables, fruit juices including squeezed juices or the like, fruit juices containing fruit particles, fruit beverages, fruit juice beverages, beverages containing fruit juices, beverages with fruit flavorings, vegetable juices, juices containing vegetables, and mixed juices containing fruits and vegetables; sport drinks, energy drinks, near water and the like drinks (e.g., water with natural or synthetic flavorants); tea type or favorite type beverages such as coffee, cocoa, black tea, green tea, oolong tea and the like; beverages containing milk components such as milk beverages, coffee containing milk components, cafe au lait, milk tea, fruit milk beverages, drinkable yogurt, lactic acid bacteria beverages or the like; and dairy products.

Generally, the amount of sweetener present in a sweetened composition varies widely depending on the particular type of sweetened composition and its desired sweetness.

Those of ordinary skill in the art can readily discern the appropriate amount of sweetener to put in the sweetened composition.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

Thus, compositions which incorporate a composition of the invention can be made by any method known to those skilled in the art that provide homogenous even or homogeneous mixtures of the ingredients. These methods include dry blending, spray drying, agglomeration, wet granulation, compaction, co-crystallization and the like.

In solid form a composition of the invention can be provided to consumers in any form suitable for delivery into the comestible to be sweetened, including sachets, packets, bulk bags or boxes, cubes, tablets, mists, or dissolvable strips. The composition can be delivered as a unit dose or in bulk form.

For liquid sweetener systems and compositions convenient ranges of fluid, semi-fluid, paste and cream forms, appropriate packing using appropriate packing material in any shape or form shall be invented which is convenient to carry or dispense or store or transport any combination containing any of the above sweetener products or combination of product produced above.

A composition of the invention may include various bulking agents, functional ingredients, colorants, flavors.

The terms "sequence homology" or "sequence identity" or "homology" or "identity" are used interchangeably herein. For the purpose of this invention, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, emboss.bioinformatics.nl). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at ncbi.nlm.nih.gov/.

Standard genetic techniques, such as overexpression of enzymes in the host cells, genetic modification of host cells, or hybridisation techniques, are known methods in the art, such as described in Sambrook and Russel (2001) "Molecular Cloning: A Laboratory Manual ($3^{rd}$ edition), Cold Spring Harbor Laboratory, Cold Spring Harbor Laboratory Press, or F. Ausubel et al, eds., "Current protocols in molecular biology", Green Publishing and Wiley Interscience, New York (1987). Methods for transformation, genetic modification etc of fungal host cells are known from e.g. EP-A-0 635 574, WO 98/46772, WO 99/60102 and WO 00/37671, WO90/14423, EP-A-0481008, EP-A-0635 574 and U.S. Pat. No. 6,265,186.

EMBODIMENTS OF THE INVENTION

1. A recombinant host capable of producing a steviol glycoside which overexpresses a polypeptide which mediates steviol glycoside transport and which polypeptide comprises the amino acid sequence set forth in SEQ ID NO: 35 or SEQ ID NO: 38 or an amino acid sequence having at least about 50% sequence identity to either thereto.
2. A recombinant host capable of producing a steviol glycoside which has been modified, preferably in its genome, to result in a deficiency in the production of a polypeptide which mediates steviol glycoside transport and which polypeptide comprises the amino acid sequence set forth in SEQ ID NO: 35 or SEQ ID NO: 38 or an amino acid sequence having at least about 50% sequence identity to either thereto.
3. A recombinant host according to embodiment 1, which comprises a recombinant nucleic acid encoding a polypeptide which comprises the amino acid sequence set forth in SEQ ID NO: 35 or SEQ ID NO: 38 or an amino acid sequence having at least about 50% sequence identity to either thereto.
4. A recombinant host according to any one of the preceding embodiments which comprises one or more recombinant nucleotide sequence(s) encoding:
   a polypeptide having ent-copalyl pyrophosphate synthase activity;
   a polypeptide having ent-Kaurene synthase activity;
   a polypeptide having ent-Kaurene oxidase activity; and
   a polypeptide having kaurenoic acid 13-hydroxylase activity.
5. A recombinant host according to any one of the preceding embodiments, which comprises a recombinant nucleic acid sequence encoding a polypeptide having NADPH-cytochrome p450 reductase activity.
6. A recombinant host according to any one of the preceding embodiments which comprises a recombinant nucleic acid sequence encoding one or more of:
   (i) a polypeptide having UGT74G1 activity;
   (ii) a polypeptide having UGT2 activity;
   (iii) a polypeptide having UGT85C2 activity; and
   (iv) a polypeptide having UGT76G1 activity.
7. A recombinant host according to any one of the preceding embodiments, wherein the host belongs to one of the genera *Saccharomyces, Aspergillus, Pichia, Kluyveromyces, Candida, Hansenula, Humicola, Issatchenkia, Trichosporon, Brettanomyces, Pachysolen, Yarrowia, Yamadazyma* or *Escherichia*.
8. A recombinant host according to embodiment 7, wherein the recombinant host is a *Saccharomyces cerevisiae* cell, a *Yarrowia lipolitica* cell, a *Candida krusei* cell, an *Issatchenkia orientalis* cell or an *Escherichia coli* cell.
9. A recombinant host according to any one of the preceding embodiments, wherein the ability of the host to produce geranylgeranyl diphosphate (GGPP) is upregulated.
10. A recombinant host according to any one of the preceding embodiments which comprises a nucleic acid sequence encoding one or more of:
    a polypeptide having hydroxymethylglutaryl-CoA reductase activity; or
    a polypeptide having farnesyl-pyrophosphate synthetase activity.
11. A recombinant host capable of producing a steviol glycoside which overexpresses a heterologous polypeptide which mediates steviol glycoside transport.
12. A process for the preparation of a steviol glycoside which comprises fermenting a recombinant host according to any one of the preceding embodiments in a suitable fermentation medium and, optionally, recovering the steviol glycoside.
13. A process according to embodiment 12 for the preparation of a steviol glyocisde, optionally wherein the process is carried out on an industrial scale.
14. A fermentation broth comprising a steviol glycoside obtainable by the process according to embodiment 12 or 13.
15. A steviol glycoside obtained by a process according to embodiment 12 or 13 or obtained from a fermentation broth according to embodiment 14.
16. A composition obtainable by a process according to embodiment 12 or 13, a composition comprising two or more steviol glycosides obtained by a process according to embodiment 12 or 13 or a composition obtained from a fermentation broth according to embodiment 14.
17. A foodstuff, feed or beverage which comprises a steviol glycoside according to claim 15 or a composition according to claim 16.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present invention is further illustrated by the following Examples:

EXAMPLES

General

Standard genetic techniques, such as overexpression of enzymes in the host cells, as well as for additional genetic modification of host cells, are known methods in the art, such as described in Sambrook and Russel (2001) "Molecular Cloning: A Laboratory Manual (3$^{rd}$ edition), Cold Spring Harbor Laboratory, Cold Spring Harbor Laboratory Press, or F. Ausubel et al, eds., "Current protocols in molecular biology", Green Publishing and Wiley Interscience, New York (1987). Methods for transformation and genetic modification of fungal host cells are known from e.g. EP-A-0 635 574, WO 98/46772, WO 99/60102 and WO 00/37671.

Example 1: Over-Expression of ERG20, BTS1 and tHMG in *S. cerevisiae*

For over-expression of ERG20, BTS1 tHMG1, expression cassettes were designed to be integrated in one locus using technology described in WO2013/076280. To amplify the 5' and 3' integration flanks for the integration locus, suitable primers and genomic DNA from a CEN.PK yeast strain (van Dijken et al. Enzyme and Microbial Technology 26 (2000) 706-714) was used. The different genes were ordered as cassettes (containing homologous sequence, promoter, gene, terminator, homologous sequence) at DNA2.0. The genes in these cassettes were flanked by constitutive promoters and terminators. See Table 1. Plasmid DNA from DNA2.0 containing the ERG20, tHMG1 and BTS1 cassettes were dissolved to a concentration of 100 ng/μl. In a 50 μl PCR mix 20 ng template was used together with 20 pmol of the primers. The material was dissolved to a concentration of 0.5 μg/μl.

TABLE 1

Composition of the over-expression constructs

| Promoter | ORF | Terminator |
|---|---|---|
| Eno2 | ERG20 | Adh1 |
| (SEQ ID NO: 1) | (SEQ ID NO: 2) | (SEQ ID NO: 3) |
| Fba1 | tHMG1 | Adh2 |
| (SEQ ID NO: 4) | (SEQ ID NO: 5) | (SEQ ID NO: 6) |
| Tef1 | BTS1 | Gmp1 |
| (SEQ ID NO: 7) | (SEQ ID NO: 8) | (SEQ ID NO: 9) |

For amplification of the selection marker, the pUG7-EcoRV construct (FIG. 1) and suitable primers were used. The KanMX fragment was purified from gel using the Zymoclean Gel DNA Recovery kit (ZymoResearch). Yeast strain Cen.PK113-3C was transformed with the fragments listed in Table 2.

TABLE 2

DNA fragments used for transformation of ERG20, tHMG1 and BTS1

| Fragment |
| --- |
| 5'YPRcTau3 |
| ERG20 cassette |
| tHMG1 cassette |
| KanMX cassette |
| BTS1 cassette |
| 3'YPRcTau3 |

Figure 2:
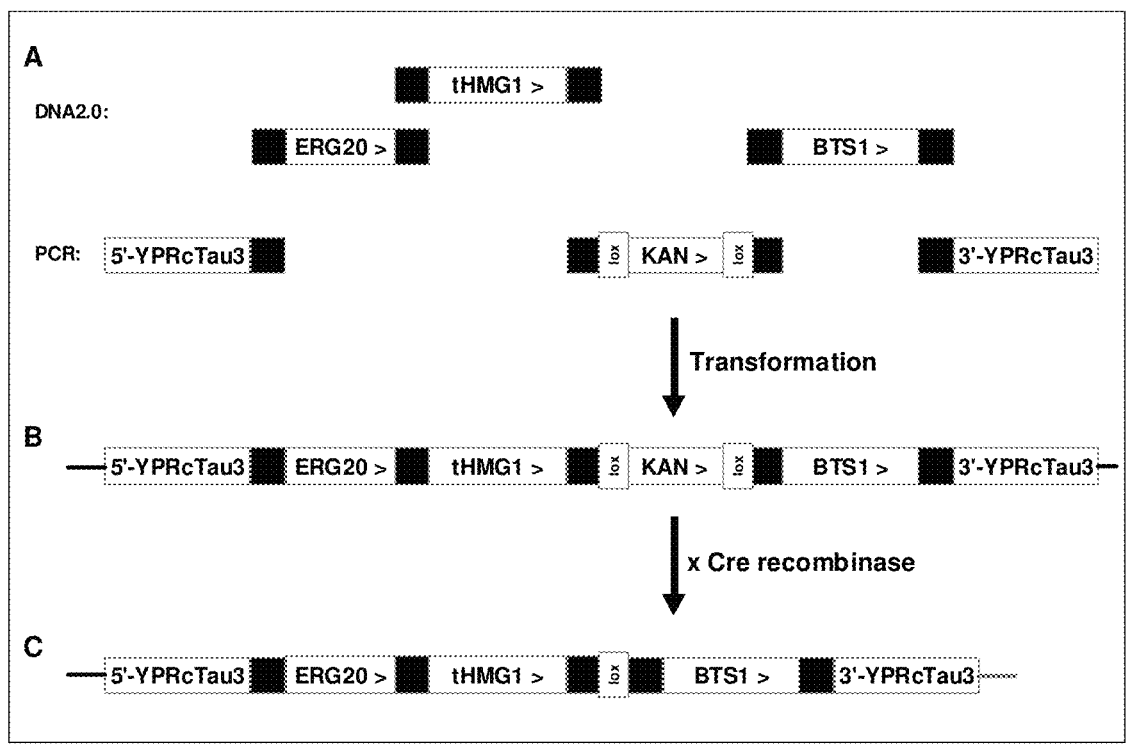
FIG. 2 sets out a schematic representation of the method by which the ERG20, tHMG1 and BTS1 over-expression cassettes are designed (A) and integrated (B) into the yeast genome. (C) shows the final situation after removal of the KANMX marker by the Cre recombinase.

After transformation and recovery for 2.5 hours in YEPhD (yeast extract phytone peptone glucose; BBL Phytone Peptone from BD) at 30° C. the cells were plated on YEPhD agar with 200 µg/ml G418 (Sigma). The plates were incubated at 30° C. for 4 days. Correct integration was established with diagnostic PCR and sequencing. Overexpression was confirmed with LC/MS on the proteins. The schematic of the assembly of ERG20, tHMG1 and BTS1 is illustrated in FIG. 2. This strain is named STV002.

Expression of CRE-recombinase in this strain led to out-recombination of the KanMX marker. Correct out-recombination, and presence of ERG20, tHMG and BTS1 was established with diagnostic PCR.

Example 2. Knock Down of Erg9

For reducing the expression of Erg9, an Erg9 knock down construct was designed and used that contains a modified 3' end, that continues into the TRP1 promoter driving TRP1 expression.

Figure 3:
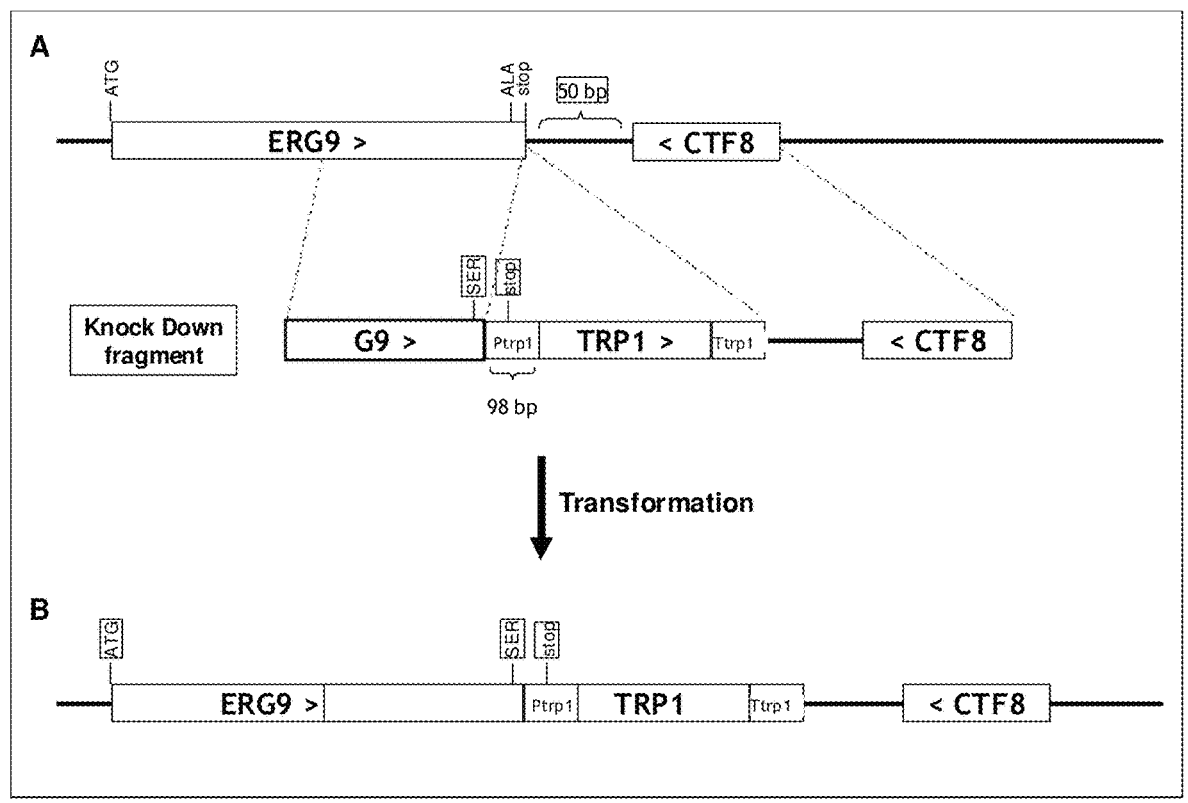
FIG. 3 sets out a schematic representation of the ERG9 knock down construct. This consists of a 500 bp long 3' part of ERG9, 98 bp of the TRP1 promoter, the TRP1 open reading frame and terminator, followed by a 400 bp long downstream sequence of ERG9. Due to introduction of a XbaI site at the end of the ERG9 open reading frame the last amino acid changes into Ser and the stop codon into Arg. A new stop codon is located in the TRP1 promoter, resulting in an extension of 18 amino acids.

The construct containing the Erg9-KD fragment was transformed to *E. coli* TOP10 cells. Transformants were grown in 2PY(2 times Phytone peptone Yeast extract), sAMP medium. Plasmid DNA was isolated with the QIAprep Spin Miniprep kit (Qiagen) and digested with SalI-HF (New England Biolabs). To concentrate, the DNA was precipitated with ethanol. The fragment was transformed to *S. cerevisiae*, and colonies were plated on mineral medium (Verduyn et al, 1992. Yeast 8:501-517) agar plates without tryptophan. Correct integration of the Erg9-KD construct was confirmed with diagnostic PCR and sequencing. The schematic of performed transformation of the Erg9-KD construct is illustrated in FIG. 3. The strain was named STV003.

Example 3. Over-Expression of UGT2_1a

For over-expression of UGT2_1a, technology was used as described in patent application nos. WO2013/076280 and WO2013/144257. The UGT2_1a was ordered as a cassette (containing homologous sequence, promoter, gene, terminator, homologous sequence) at DNA2.0. For details, see Table 3. To obtain the fragments containing the marker and Cre-recombinase, technology was used as described in patent application no. WO2013/135728. The NAT marker, conferring resistance to nourseothricin was used for selection.

TABLE 3

Composition of the over-expression construct

| Promoter | ORF | Terminator |
| --- | --- | --- |
| Pgk1 (SEQ ID NO: 10) | UGT2_1a (SEQ ID NO: 11) | Adh2 (SEQ ID NO: 6) |

Suitable primers were used for amplification. To amplify the 5' and 3' integration flanks for the integration locus, suitable primers and genomic DNA from a CEN.PK yeast strain was used.

*S. cerevisiae* yeast strain STV003 was transformed with the fragments listed in Table 4, and the transformation mix was plated on YEPhD agar plates containing 50 µg/ml nourseothricin (Lexy NTC from Jena Bioscience).

TABLE 4

DNA fragments used for transformation of UGT2_1a

| Fragment |
| --- |
| 5'Chr09.01 |
| UGT2_1a cassette |
| NAT-CR |
| RE |
| 3'Chr09.01 |

Figure 4:
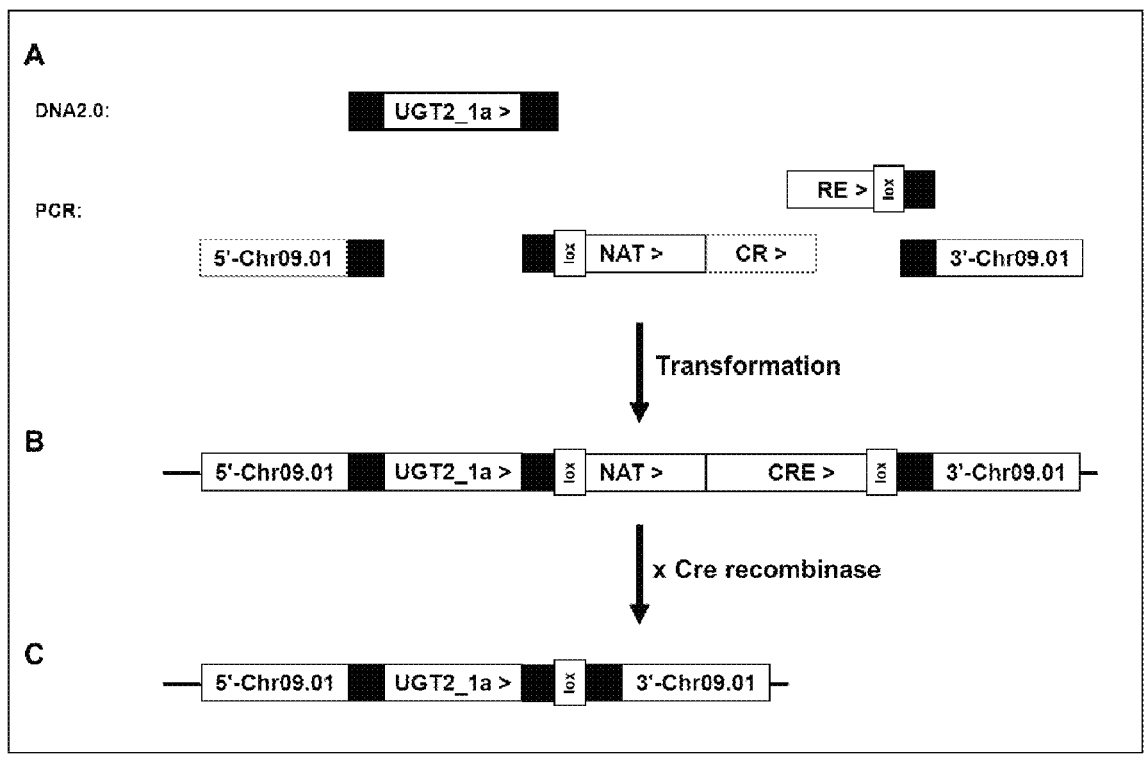
FIG. 4 sets out a schematic representation of how UGT2_1a is integrated into the genome. A. different fragments used in transformation; B. situation after integration; C. situation after expression of Cre recombinase.

Expression of the CRE recombinase is activated by the presence of galactose. To induce the expression of the CRE recombinase, transformants were restreaked on YEPh Galactose medium. This resulted in out-recombination of the marker(s) located between lox sites. Correct integration of the UGT2_1a and out-recombination of the NAT marker was confirmed with diagnostic PCR. The resulting strain was named STV004. The schematic of the performed transformation of the UGT2_1a construct is illustrated in FIG. 4.

Example 4. Over-Expression of Production Pathway to RebA: CPS, KS, KO, KAH, CPR, UGT1, UGT3 and UGT4

All pathway genes leading to the production of RebA were designed to be integrated in one locus using technology described in patent application nos. WO2013/076280 and WO2013/144257. To amplify the 5' and 3' integration flanks for the integration locus, suitable primers and genomic DNA from a CEN.PK yeast strain was used. The different genes were ordered as cassettes (containing homologous sequence, promoter, gene, terminator, homologous sequence) at DNA2.0 (see Table 5 for overview). The DNA from DNA2.0 was dissolved to 100 ng/µl. This stock solution was further diluted to 5 ng/µl, of which 1 µl was used in a 50 µl-PCR mixture. The reaction contained 25 pmol of each primer. After amplification, DNA was purified with the NucleoSpin 96 PCR Clean-up kit (Macherey-Nagel) or alternatively concentrated using ethanol precipitation.

TABLE 5

Sequences used for production pathway to RebA

| Promoter | ORF | SEQ ID | Terminator |
| --- | --- | --- | --- |
| Kl prom 12.pro (SEQ ID NO: 12) | trCPS_SR | 13 | Sc ADH2.ter (SEQ ID NO: 9) |
| Sc PGK1.pro (SEQ ID NO: 10) | trKS_SR | 14 | Sc TAL1.ter (SEQ ID NO: 15) |

TABLE 5-continued

Sequences used for production pathway to RebA

| Promoter | ORF | SEQ ID | Terminator |
|---|---|---|---|
| Sc ENO2.pro (SEQ ID NO: 1) | KO_2 | 16 | Sc TPI1.ter (SEQ ID NO: 17) |
| Ag lox_TEF1.pro (SEQ ID NO: 18) | KANMX | 19 | Ag TEF1_lox.ter (SEQ ID NO: 20) |
| Sc TEF1.pro (SEQ ID NO: 7) | KAH_4 | 21 | Sc GPM1.ter (SEQ ID NO: 9) |
| Kl prom 6.pro (SEQ ID NO: 22) | CPR_3 | 23 | Sc PDC1.ter (SEQ ID NO: 24) |
| Kl prom 3.pro (SEQ ID NO: 25) | UGT1_SR | 26 | Sc TDH1.ter (SEQ ID NO: 27) |
| Kl prom 2.pro (SEQ ID NO: 28) | UGT3_SR | 29 | Sc ADH1.ter (SEQ ID NO: 3) |
| Sc FBA1.pro (SEQ ID NO: 4) | UGT4_SR | 30 | Sc ENO1.ter (SEQ ID NO: 31) |

All fragments for the pathway to RebA, the marker and the flanks (see overview in Table 6) were transformed to *S. cerevisiae* yeast strain STV004. After overnight recovery in YEPhD at 20° C. the transformation mixes were plated on YEPhD agar containing 200 µg/ml G418. These were incubated 3 days at 25° C. and one night at RT.

TABLE 6

DNA fragments used for transformation of CPS, KS, KO, KanMX, KAH, CPR, UGT1, UGT3 and UGT4

| Fragment |
|---|
| 5'INT1 |
| CPS cassette |
| KS cassette |
| KO cassette |
| KanMX cassette |
| KAH cassette |
| CPR cassette |
| UGT1 cassette |
| UGT3 cassette |
| UGT4 cassette |
| 3'INT1 |

Figure 5:
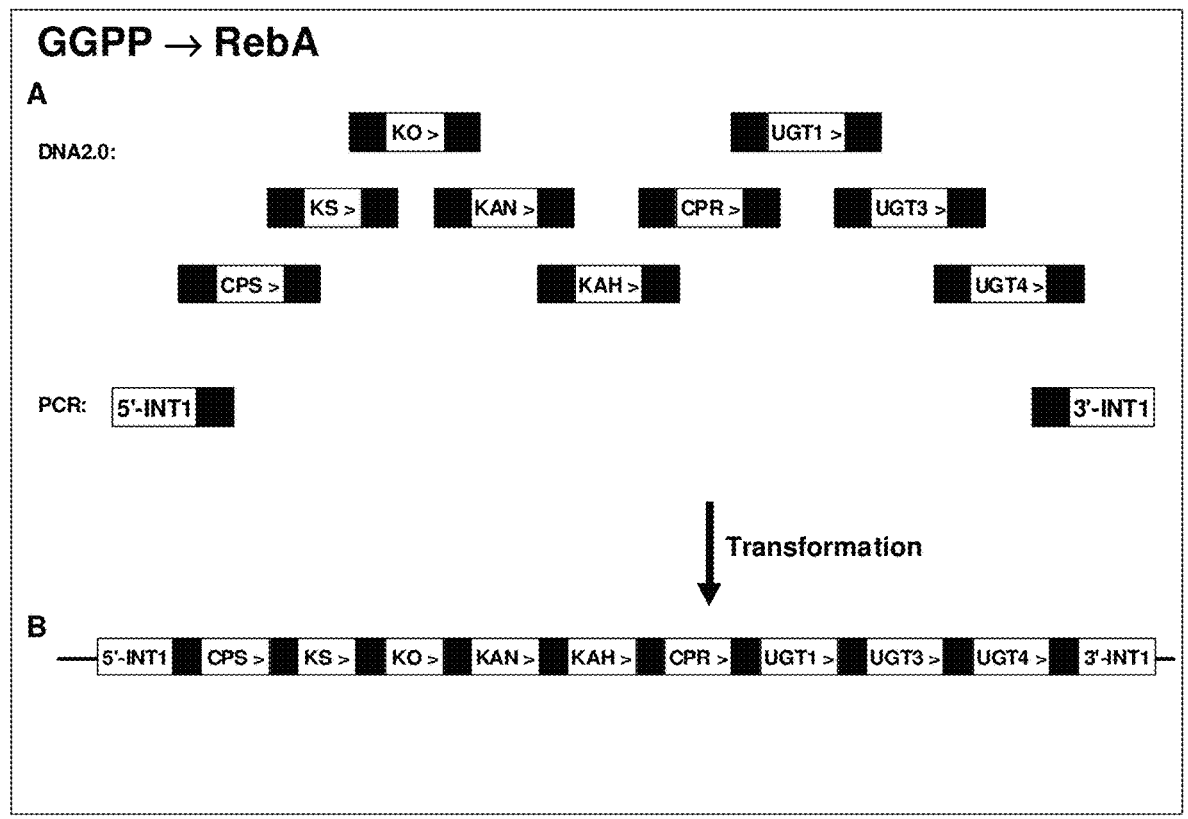
FIG. 5 sets out a schematic representation of how the pathway from GGPP to RebA is integrated into the genome. A. different fragments used in transformation; B. situation after integration.

Correct integration was confirmed with diagnostic PCR and sequence analysis (3500 Genetic Analyzer, Applied Biosystems). The sequence reactions were done with the BigDye Terminator v3.1 Cycle Sequencing kit (Life Technologies). Each reaction (10 µl) contained 50 ng template and 3.2 pmol primer. The products were purified by ethanol/EDTA precipitation, dissolved in 10 µl HiDi formamide and applied onto the apparatus. The strain was named STV016. The schematic of how the pathway from GGPP to RebA is integrated into the genome is illustrated in FIG. 5. Table 7 sets out the strains used in Examples 1 to 5.

Example 5: Construction of Strain STV027

To remove the KanMX marker from the chromosome of strain STV016, this strain was transformed with plasmid pSH65, expressing Cre-recombinase (Guldender, 2002). Subsequently plasmid pSH65 was cured from the strain by growing on non-selective medium (YEP 2% glucose). The resulting, KanMX-free and pSH65-free strains, as determined by plating on plates containing 200 µg G418/ml or 20 µg phleomycin/ml, where no growth should occur, was named STV027. Absence of the KanMX marker was furthermore confirmed with diagnostic PCR. The resulting strain was named STV027.

Example 6: Construction of Strain STV035

To introduce additional copies of KAH and CPR available PCR fragments were used (see Table 6 and Table 7). The KanMX selection marker fragment was amplified from pUG7-EcoRV (FIG. 1) with the appropriate primers. To amplify the 5' and 3' integration flanks for the integration locus, suitable primers and genomic DNA from a CEN.PK yeast strain was used.

STV027 was transformed with these fragments (Table 7) according the Gietz method. After 2 h recovery in YEPhD at 30° C. the transformation mixes were plated on YEPhD agar containing 200 µg/ml G418. These were incubated for 4 days at 30° C.

TABLE 7

DNA fragments used for transformation of KanMX, KAH and CPR to STV027.

| Fragment |
|---|
| 5'Chr11.04 |
| KanMX cassette |
| KAH cassette |
| CPR cassette |
| 3' Chr11.04 |

Figure 6:
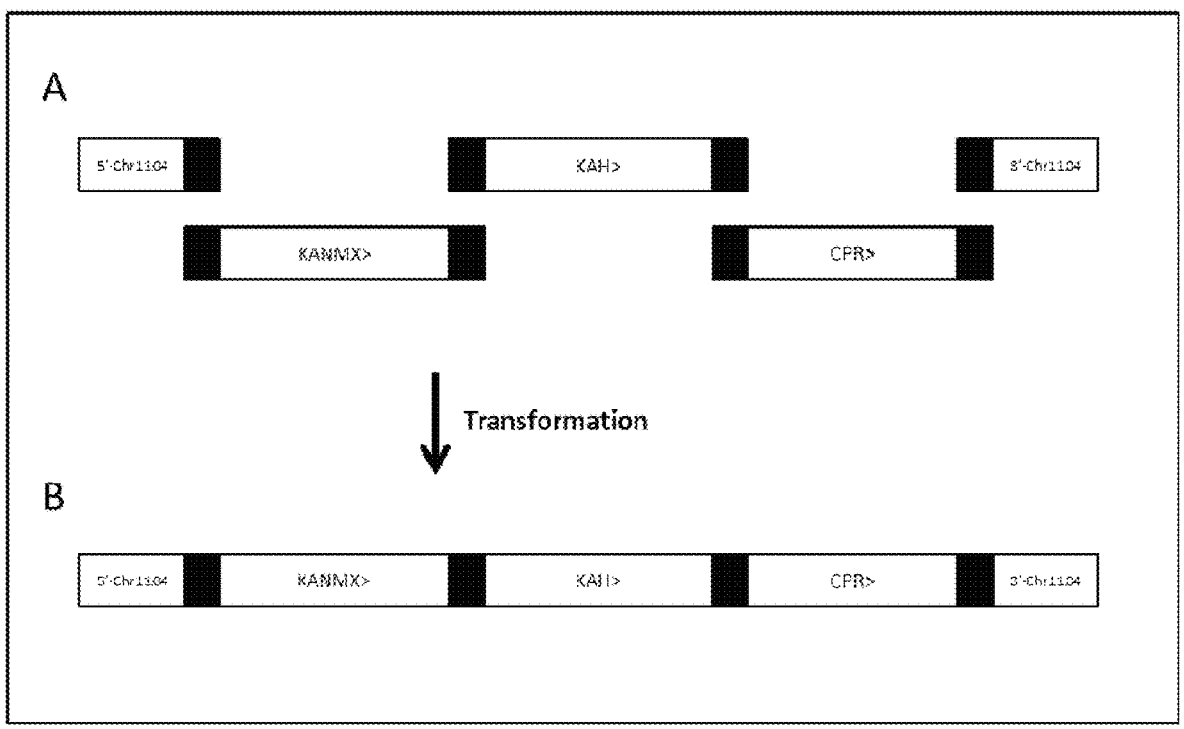
FIG. 6 sets out a schematic representation of how KAH and CPR are integrated in the genome. A. different fragments used in transformation; B. situation after integration.

The schematic of how KAH and CPR are integrated into the genome is illustrated in FIG. 6. Correct integration was confirmed with diagnostic PCR. The resulting strain was named STV035.

Example 7: Construction of Strain STV058

For the integration of a second copy of CPS this gene was amplified together with a TDH3 promoter and ADH2 terminator.

TABLE 8

Sequences in CPS cassette (2)

| Promoter | ORF | SEQ ID | Terminator |
|---|---|---|---|
| Sc TDH3.pro (SEQ ID NO: 32) | trCPS_SR | 12 | Sc ADH2.ter (SEQ ID NO: 9) |

Figure 7:
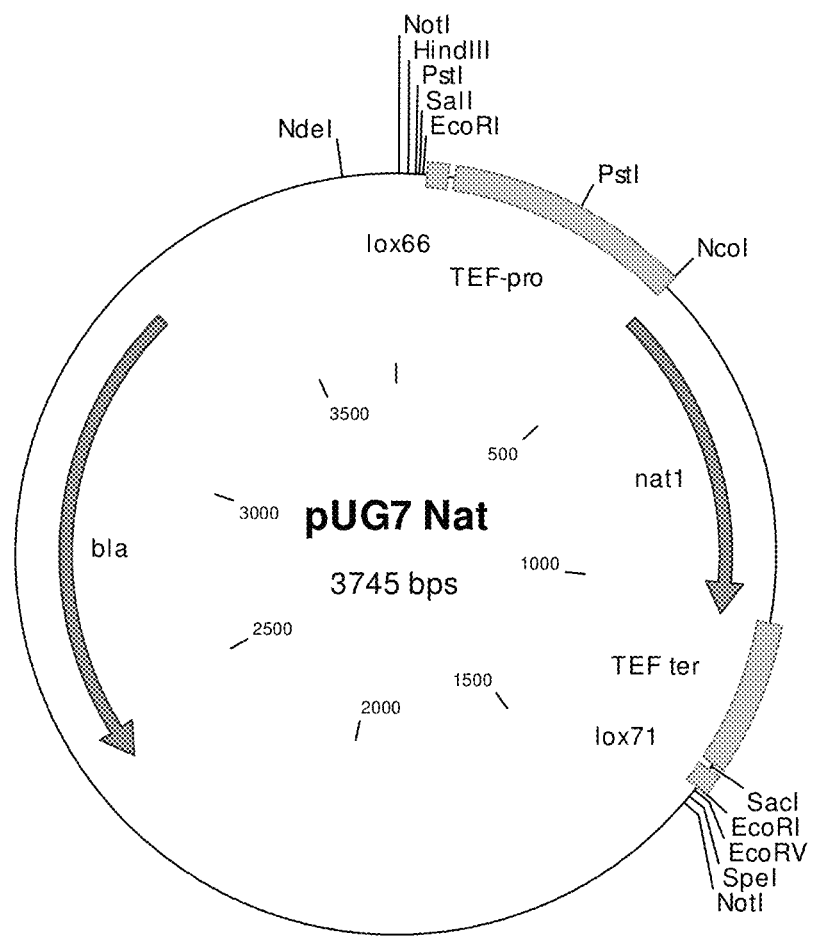
FIG. 7 sets out a schematic representation of the plasmid pUG7-NAT.

Due to presence of a KanMX marker in STV035 a NAT marker was amplified from pUG7-NAT (FIG. 7) with the appropriate primers. To amplify the 5' and 3' integration flanks for the integration locus, suitable primers and genomic DNA from a CEN.PK yeast strain was used.

TABLE 9

DNA fragments used for transformation of CPS and NAT to STV035.

| Fragment |
|---|
| 5'Chr2.06 |
| CPS cassette (2) |
| NAT |
| 3' Chr2.06 |

Figure 8:
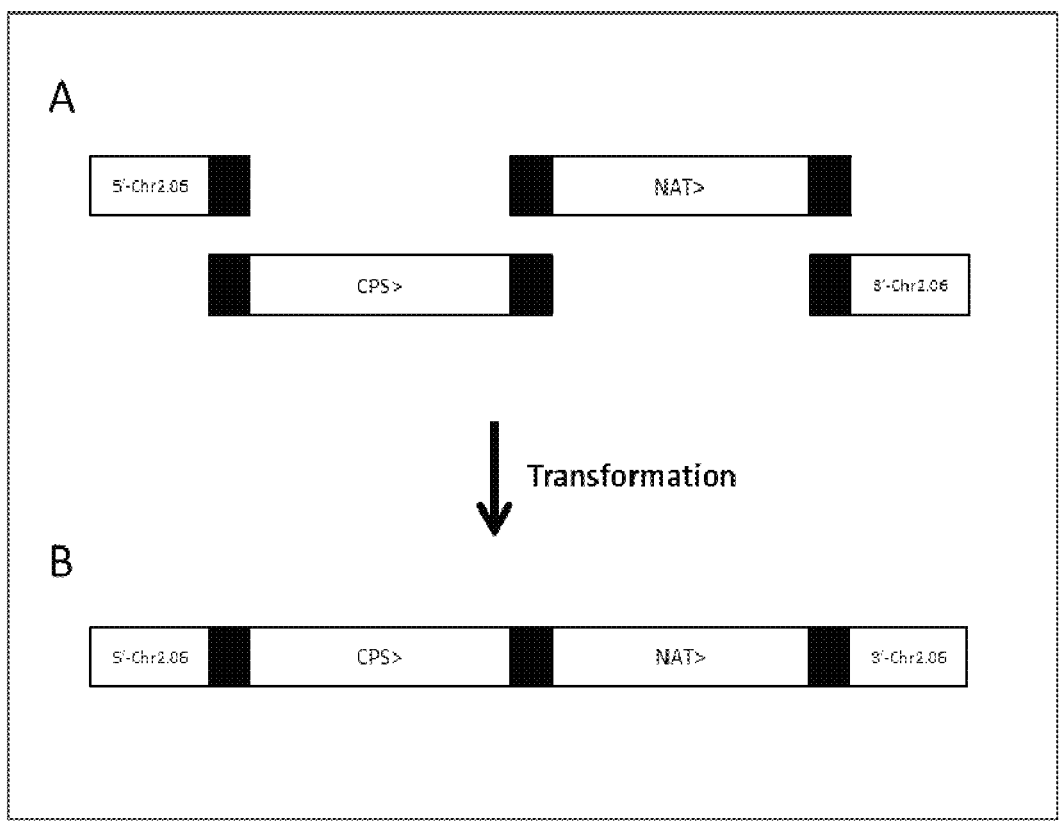
FIG. 8 sets out a schematic representation of how CPS is integrated in the genome. A. different fragments used in transformation; B. situation after integration.
Figure 9:
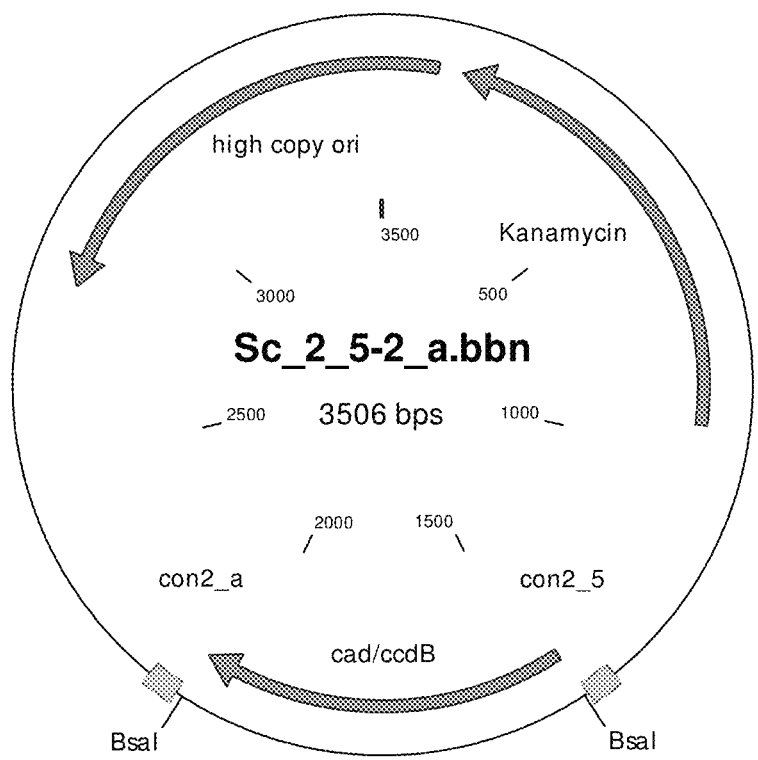
FIG. 9 sets out a schematic representation of plasmid Sc_2_5-2_a.bbn

The different fragments for integration of the second copy of CPS (Table 9) were combined and transformed to STV035. After recovery the transformation mix was plated on YEPhD agar plates containing 50 µg/ml nourseothricin. These were incubated for 3 days at 30° C. Correct integration was confirmed with diagnostic PCR. The new strain was named STV058. The schematic of how the CPS is integrated into the genome is illustrated in FIG. 8.

TABLE 10

Table of strains

| Strain | Background | Genotype |
| --- | --- | --- |
| Cen.PK113-3C | — | MATa URA3 HIS3 LEU2 trp1-289 MAL2-8C SUC2 |
| STV002 | Cen.PK113-3C | MATa URA3 HIS3 LEU2 trp1-289 MAL2-8C SUC2 YPRcTau3::ERG20, tHMG1, KanMX, BTS1 |
| STV003 | STV002 | MATa URA3 HIS3 LEU2 trp1-289 MAL2-8C SUC2 YPRcTau3::ERG20, tHMG1, KanMX, BTS1 ERG9::ERG9-KD TRP1 |
| STV004 | STV003 | MATa URA3 HIS3 LEU2 trp1-289 MAL2-8C SUC2 YPRcTau3::ERG20, tHMG1, BTS1 ERG9::ERG9-KD TRP1 Chr09.01::UGT2_1a |
| STV016 | STV004 | MATa URA3 HIS3 LEU2 trp1-289 MAL2-8C SUC2 YPRcTau3::ERG20, tHMG1, BTS1 ERG9::ERG9-KD TRP1 Chr09.01::UGT2_1a INT1::CPS, KS, KO, KanMX, KAH, CPR, UGT1, UGT3, UGT4 |
| STV027 | STV016 | MATa URA3 HIS3 LEU2 trp1-289 MAL2-8C SUC2 YPRcTau3::ERG20, tHMG1, BTS1 ERG9::ERG9-KD TRP1 Chr09.01::UGT2_1a INT1::CPS, KS, KO, KAH, CPR, UGT1, UGT3, UGT4 |
| STV035 | STV027 | MATa URA3 HIS3 LEU2 trp1-289 MAL2-8C SUC2 YPRcTau3::ERG20, tHMG1, BTS1 ERG9::ERG9-KD TRP1 Chr09.01::UGT2_1a INT1::CPS, KS, KO, KAH, CPR, UGT1, UGT3, UGT4 5'Chr11.04::KanMX, KAH, CPR |
| STV058 | STV035 | MATa URA3 HIS3 LEU2 trp1-289 MAL2-8C SUC2 YPRcTau3::ERG20, tHMG1, BTS1 ERG9::ERG9-KD TRP1 Chr09.01::UGT2_1a INT1::CPS, KS, KO, KAH, CPR, UGT1, UGT3, UGT4 5'Chr11.04::KanMX, KAH, CPR 5'Chr2.06::CPS, NAT |

Example 8. Expression of *I. orientalis* ALNQ 007_38000 and ALNQ 214_12000 in *S. cerevisiae* Strain STV058

For expression of ALNQ_007_38000 (SEQ ID NO: 33) and ALNQ_214_12000 (SEQ ID NO: 36), expression cassettes were designed to be integrated in the *S. cerevisiae* STV058 Chr01.05 locus, using technology described in patent application nos. WO2013/076280 and WO2013/144257. To amplify the 5' and 3' integration flanks for the integration locus, suitable primers and genomic DNA from a CEN.PK yeast strain were used.

The two transporter genes were amplified from *I. orientalis* CBS 5147 genomic DNA using suitable primers. The PCR amplicons were sub-cloned in a in a Zero Blunt TOPO vector (Life Technologies). The genes were cloned into the Sc_2_5-2_a.bbn vector using BspMI or BsaI in which they were flanked by the constitutive promoters KI_ENO1 or Sc_GPM1 and Sc_TAL1 terminator resulting in two expression cassettes for each transporter gene. The expression cassettes were PCR-amplified in six times 50 µl PCR mix. The PCR product was purified and concentrated using NucleoSpin Gel and PCR Clean-up Kit (Machery Nagel).

Figure 10:
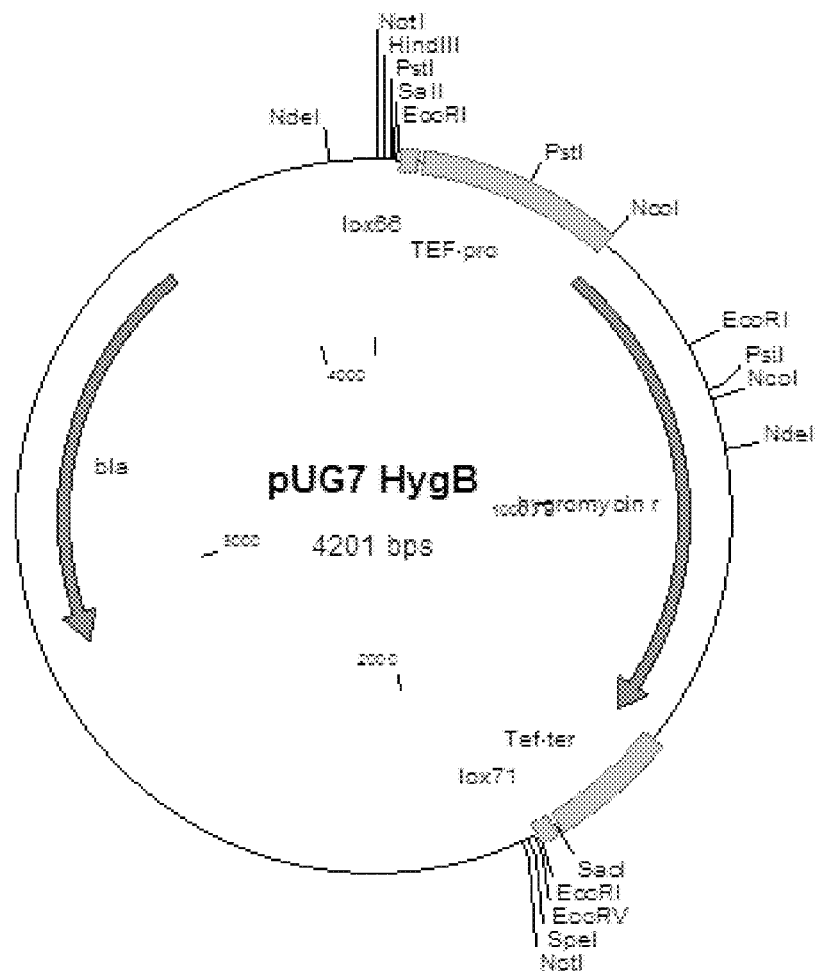
FIG. 10 sets out a schematic representation of the plasmid pUG7-HYG
Figure 11:
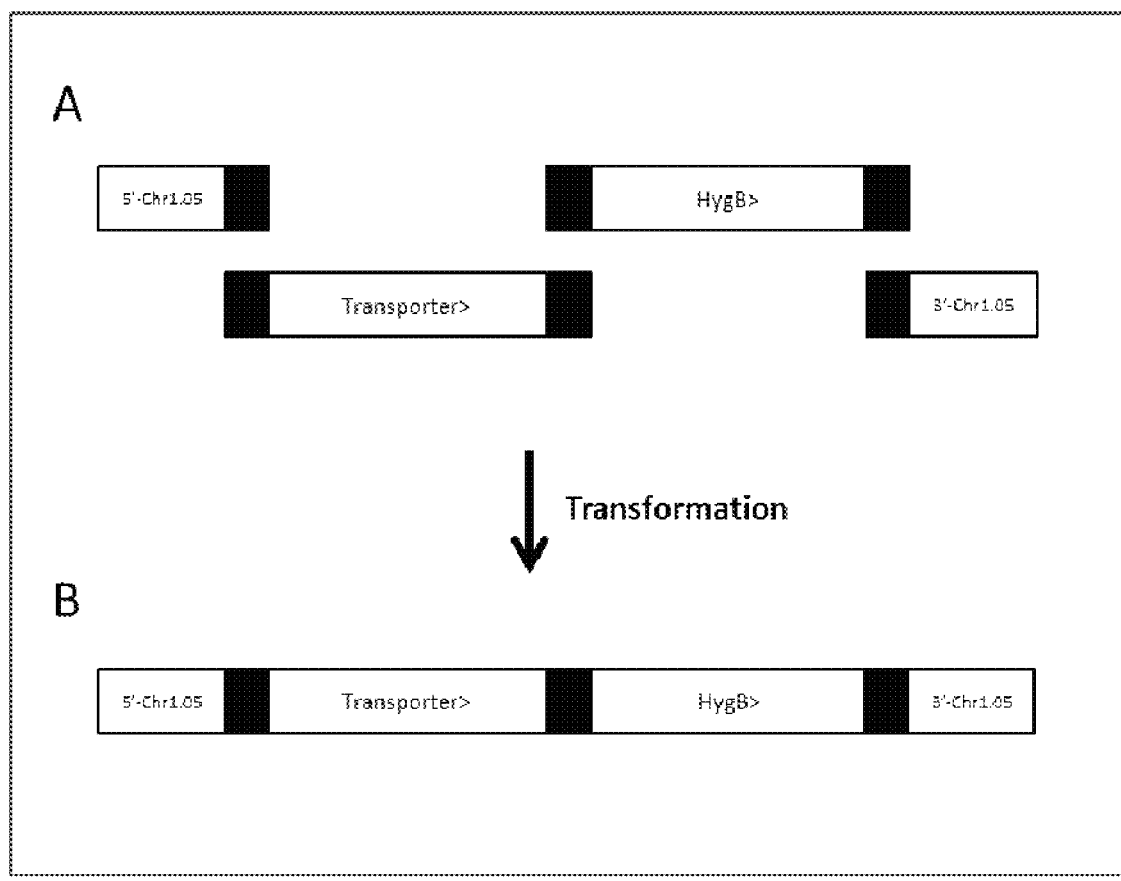
FIG. 11 sets out a schematic representation of how the transporter genes ALNQ_007_38000 and ALNQ_214_12000 are integrated into the genome. A. different fragments used in transformation; B. situation after integration.

For amplification of the selection marker, the pUG7-HygB construct (FIG. 10) and suitable primers were used. The PCR product was purified and concentrated using NucleoSpin Gel and PCR Clean-up Kit (Machery Nagel). Yeast strain *S. cerevisiae* STV058 was transformed with the fragments listed in Table 11. The in-vivo assembly is illustrated in FIG. 11.

TABLE 11

Fragments transformed to *S. cerevisiae* STV058

| Over expression strain | ENO1_ALNQ_007_38000 | GPM1_ALNQ_007_38000 | ENO1_ALNQ_214_12000 | GPM1_ALNQ_214_12000 |
| --- | --- | --- | --- | --- |
| 5' Chr01.05 | 205 ng | 205 ng | 205 ng | 205 ng |
| Transporter ORF cassette | 477 ng | 258 ng | 529 ng | 246 ng |
| HygB cassette | 204 ng | 204 ng | 204 ng | 204 ng |
| 3' Chr01.05 | 201 ng | 201 ng | 201 ng | 201 ng |

After transformation and recovery for 2 hours in YEPhD at 30° C. the cells were plated on YEPhD agar with 200 µg/ml HygB (Invitrogen). The plates were incubated at 30° C. for 2 days. Transformants were purified by re-streaking them on YEPhD agar with 200 µg/ml HygB. Correct integration and assembly was established with diagnostic PCR.

Example 9. Fermentation of STV058 and ALNQ 007_38000 and ALNQ 214_12000 Transporter Overexpression Strains A pre-culture was inoculated with colony material from YEPh-D agar. The pre-culture was grown in 96-Half Deep Well Plate in 200 µl mineral medium with glucose as carbon source. The pre-culture was incubated 72 hours in an Infors incubator at 27° C., 750 rpm and 80% humidity.

40 µl of pre-culture was used to inoculate 2.5 ml mineral medium with glucose as carbon source in a 24-Deep Well Plate. These production cultures were incubated 120 hours in an Infors incubator at 27° C., 550 rpm, 80% humidity. The production cultures were well homogenized and 0.5 ml of culture was transferred to a 96-well plate. This sample was used as whole broth sample. The remainder of the production cultures were pelleted by centrifugation at 3000×g for 10 minutes. After centrifugation 0.5 supernatant was transferred to a 96-well plate. This sample was used as supernatant sample. Both the whole broth 96-well plates and supernatant 96-well plates were incubated for 10 minutes at 90° C. in a water bath and cooled down to room temperature. To each well 0.25 ml of acetonitrile was added and homogenized. The plates were then centrifuged at 3000×g for 10 minutes to pellet cell material and debris. The whole broth and supernatant samples were diluted 200 times in 33% acetonitrile. Samples were analyzed for RebA and other steviolglycosides using LC/MS. We found that the strains that had the particular transporter gene over-expressions as described, produced higher titers of Rebaudioside A or other steviolglycosides such as Rebaudioside B in the supernatant fraction compared to the parent strain. For an overview of the results, see Tables 12, 13.

TABLE 12

Rebaudioside A concentrations in supernatant and broth

| Strain | Reb A supernatant (mg/L) | Reb A broth (mg/L) |
|---|---|---|
| STV058 | 29 | 137 |
| ENO1p_ALNQ_007_38000 | 51 | 95 |
| GPM1p_ALNQ_007_38000 | 53 | 79 |
| ENO1p_ALNQ_214_12000 | 171 | 178 |
| GPM1p_ALNQ_214_12000 | 155 | 151 |

Figure 12:
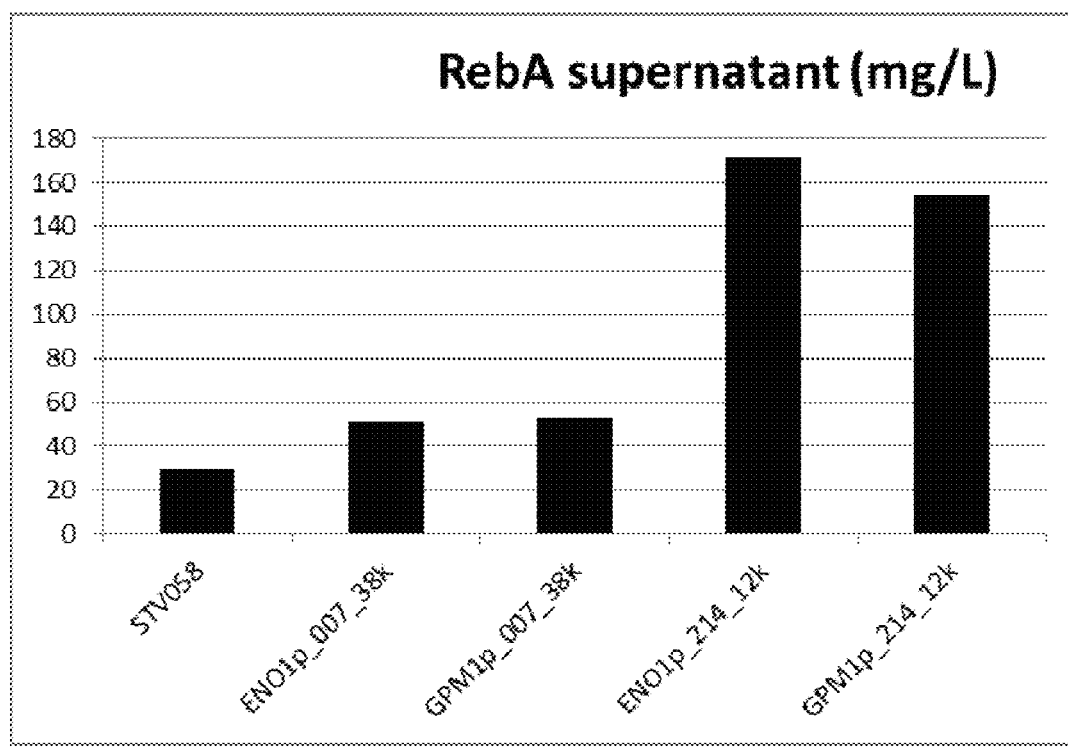
FIG. 12 sets out the production of Rebaudioside A in the supernatant in strains with over-expressed transporters ALNQ_007_38000 and ALNQ_214_12000.

Strains with over-expression of the ALNQ_007_38000 transporter or the ALNQ_214_12000 transporter have increased levels of Rebaudioside A in the supernatant. With the over-expression of the ALNQ_214_12000 transporter, the amount of RebA in the supernatant was increased with 5 to 6 fold compared to the reference strain. See also FIG. 12.

TABLE 13

Rebaudioside B concentrations in supernatant and broth

| Strain | Reb B supernatant (mg/L) | Reb B broth (mg/L) |
|---|---|---|
| STV058 | 7 | 41 |
| ENO1p_ALNQ_007_38000 | 124 | 139 |
| GPM1p_ALNQ_007_38000 | 165 | 170 |
| ENO1p_ALNQ_214_12000 | 15 | 19 |
| GPM1p_ALNQ_214_12000 | 15 | 17 |

Figure 13:
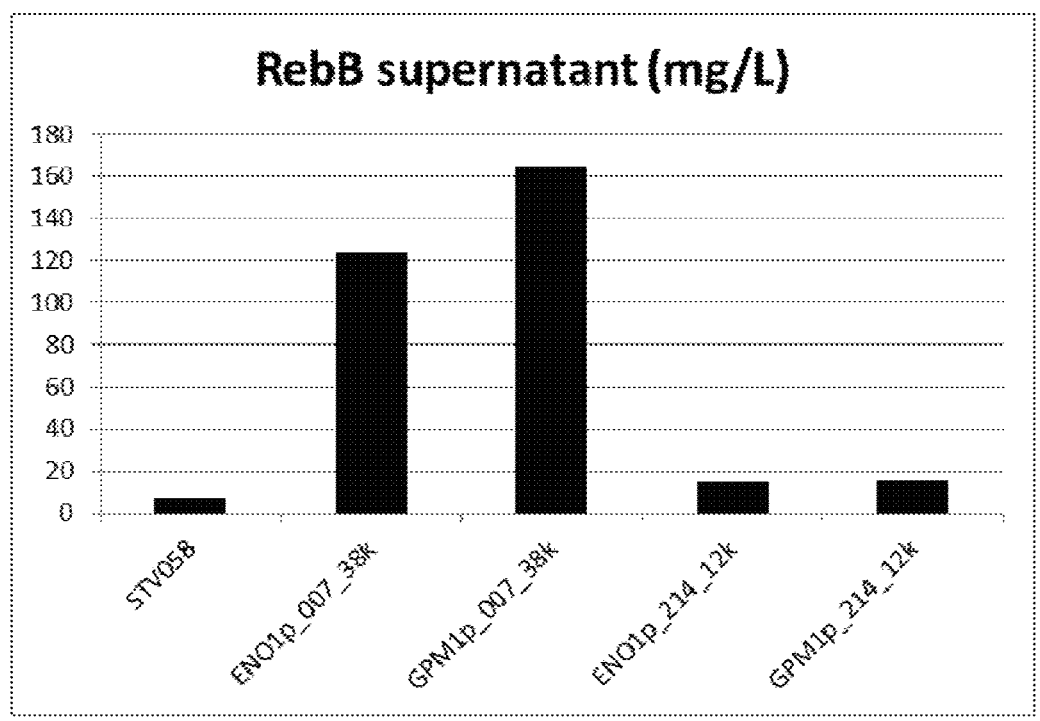
FIG. 13 sets out the production of Rebaudioside B in the supernatant in strains with over-expressed transporters ALNQ_007_38000 and ALNQ_214_12000.

Strains with over-expression of the ALNQ_007_38000 transporter or the ALNQ_214_12000 transporter have increased levels of Rebaudioside B in the supernatant. In the case of the ALNQ_007_38000 transporter this also results in a higher RebB concentration in the broth. See also FIG. 13. The observation that such high amounts of RebB are exported into the supernatant offer an explanation for the reduced Rebaudioside A production in the broth (Table 12), as Rebaudioside B in the supernatant is no longer available as substrate for Rebaudioside A production, which occurs inside the cell. For the extracellular production of Rebaudioside A or products downstream of Rebaudioside A, therefore the ALNQ_007_38000 (or equivalent) transporter may be a target for deletion in a host that contains such as transporter, such as *I. orientalis*, in combination with over-expression of a transporter that more specifically transports Rebaudioside A, such as the ALNQ_214_12000 transporter.

Strains with over-expression of the ALNQ_007_38000 transporter or the ALNQ_214_12000 transporter have decreased levels of Rebaudioside M in the broth. Because both transporters are efficient in exporting steviol glycosides such as Rebaudioside A and Rebaudioside B, lower amounts of these intermediates are available inside the cell for the conversion towards Rebaudioside M. Therefore, these transporters (or equivalent) may be target for deletion in a host that would have such a transporter, such as *I. orientalis*, to increase Rebaudioside M production.

TABLE 14

Rebaudioside M concentrations in supernatant and broth

| Strain | Reb M broth (mg/L) |
|---|---|
| STV058 | 60 |
| ENO1p_ALNQ_007_38000 | 25 |
| GPM1p_ALNQ_007_38000 | 13 |
| ENO1p_ALNQ_214_12000 | 7 |
| GPM1p_ALNQ_214_12000 | 2 |

TABLE 15

Description of the sequence listing

| SEQ ID NO | Description |
|---|---|
| SEQ ID NO: 1 | Eno2 promoter from *S. cerevisiae* |
| SEQ ID NO: 2 | ERG20 nucleic acid from *S. cerevisiae* |
| SEQ ID NO: 3 | Adh1 terminator from *S. cerevisiae* |
| SEQ ID NO: 4 | Fba1 promoter from *S. cerevisiae* |
| SEQ ID NO: 5 | tHMG nucleic acid from *S. cerevisiae* |
| SEQ ID NO: 6 | Adh2 terminator from *S. cerevisiae* |
| SEQ ID NO: 7 | Tef1 promoter from *S. cerevisiae* |
| SEQ ID NO: 8 | BTS1 nucleic acid from *S. cerevisiae* |
| SEQ ID NO: 9 | Gmp1 terminator from *S. cerevisiae* |
| SEQ ID NO: 10 | Pgk1 promoter from *S. cerevisiae* |
| SEQ ID NO: 11 | UGT2_1a CpO for *S. cerevisiae* |
| SEQ ID NO: 12 | Kl prom 12 promoter |
| SEQ ID NO: 13 | trCPS from *S. rebaudiana* CpO for *S. cerevisiae* |
| SEQ ID NO: 14 | trKS from *S. rebaudiana* CpO for *S. cerevisiae* |
| SEQ ID NO: 15 | TAL1 terminator from *S. cerevisiae* |
| SEQ ID NO: 16 | KO_2_Lactuca_sativa CpO for *S. cerevisiae* |
| SEQ ID NO: 17 | Tpi1 terminator from *S. cerevisiae* |
| SEQ ID NO: 18 | Ag lox_TEF1.pro nucleic acid construct |
| SEQ ID NO: 19 | KANMX ORF CpO for *S. cerevisiae* |
| SEQ ID NO: 20 | Ag Tef1_lox.ter nucleic acid construct |

TABLE 15-continued

Description of the sequence listing

| SEQ ID NO | Description |
| --- | --- |
| SEQ ID NO: 21 | KAH_4 from *Arabidopsis thaliana* CpO for *S. cerevisiae* |
| SEQ ID NO: 22 | KI prom 6.pro promoter |
| SEQ ID NO: 23 | CPR_3 from *Arabidopsis thaliana* CpO for *S. cerevisiae* |
| SEQ ID NO: 24 | Pdc1 terminator from *S. cerevisiae* |
| SEQ ID NO: 25 | KI prom3 promoter |
| SEQ ID NO: 26 | UGT1 from *S. rebaudiana* CpO for *S. cerevisiae* |
| SEQ ID NO: 27 | Tdh1 terminator from *S. cerevisiae* |
| SEQ ID NO: 28 | KI prom 2 promoter |
| SEQ ID NO: 29 | UGT3 from *S. rebaudiana* CpO for *S. cerevisiae* |
| SEQ ID NO: 30 | UGT4 from *S. rebaudiana* CpO for *S. cerevisiae* |
| SEQ ID NO: 31 | Eno1 terminator from *S. cerevisiae* |
| SEQ ID NO: 32 | TDH3 promoter from *S. cerevisiae* |
| SEQ ID NO: 33 | ALNQ_007_38000 CpO for *S. cerevisiae* |
| SEQ ID NO: 34 | ALNQ_007_38000 WT CDS from *I. orientalis* |
| SEQ ID NO: 35 | ALNQ_007_38000 WT from *I. orientalis* |
| SEQ ID NO: 36 | ALNQ_214_12000 CpO for *S. cerevisiae* |
| SEQ ID NO: 37 | ALNQ_214_12000 WT CDS from *I. orientalis* |
| SEQ ID NO: 38 | ALNQ_214_12000 WT from *I. orientalis* |

The invention claimed is:

1. A recombinant host capable of producing a steviol glycoside which overexpresses a polypeptide which mediates steviol glycoside transport and which polypeptide comprises the amino acid sequence set forth in SEQ ID NO:35 or an amino acid sequence having at least 98% sequence identity thereto.

2. The recombinant host according to claim 1, which comprises a recombinant nucleic acid encoding a polypeptide which comprises the amino acid sequence set forth in SEQ ID NO:35 or an amino acid sequence having at least 98% sequence identity thereto.

3. The recombinant host according to claim 1, which further comprises one or more recombinant nucleotide sequence(s) encoding:
   a polypeptide having ent-copalyl pyrophosphate synthase activity;
   a polypeptide having ent-Kaurene synthase activity;
   a polypeptide having ent-Kaurene oxidase activity; and
   a polypeptide having kaurenoic acid 13-hydroxylase activity.

4. The recombinant host according to claim 1, which further comprises a recombinant nucleic acid sequence encoding a polypeptide having NADPH-cytochrome p450 reductase activity.

5. The recombinant host according to claim 1, which further comprises a recombinant nucleic acid sequence encoding one or more of:
   (i) a polypeptide having UGT74G1 activity;
   (ii) a polypeptide having UGT2 activity;
   (iii) a polypeptide having UGT85C2 activity; and
   (iv) a polypeptide having UGT76G1 activity.

6. The recombinant host according to claim 1, wherein the host belongs to one of the genera *Saccharomyces, Aspergillus, Pichia, Kluyveromyces, Candida, Hansenula, Humicola, Issatchenkia, Trichosporon, Brettanomyces, Pachysolen, Yarrowia, Yamadazyma,* or *Escherichia.*

7. The recombinant host according to claim 6, wherein the recombinant host is a *Saccharomyces cerevisiae* cell, a *Yarrowia lipolitica* cell, an *Issatchenkia orientalis* cell or an *Escherichia coli* cell.

8. The recombinant host according to claim 1, wherein the ability of the host to produce geranylgeranyl diphosphate (GGPP) is upregulated.

9. The recombinant host according to claim 1, which further comprises a nucleic acid sequence encoding one or more of:
   a polypeptide having hydroxymethylglutaryl-CoA reductase activity; or
   a polypeptide having farnesyl-pyrophosphate synthetase activity.

* * * * *